US012734322B2

(12) United States Patent
Scheirlinck et al.

(10) Patent No.: US 12,734,322 B2
(45) **Date of Patent: *Sep. 15, 2026**

(54) CUSTOMIZABLE RESPIRATORY MASK

(71) Applicant: Fisher & Paykel Healthcare Limited, Auckland (NZ)

(72) Inventors: Erik Robertus Scheirlinck, Auckland (NZ); Daniel John Smith, Auckland (NZ)

(73) Assignee: Fisher & Paykel Healthcare Limited, Auckland (NZ)

(*) Notice: Subject to any disclaimer, the term of this patent is extended or adjusted under 35 U.S.C. 154(b) by 395 days.

This patent is subject to a terminal disclaimer.

(21) Appl. No.: 18/149,434

(22) Filed: Jan. 3, 2023

(65) Prior Publication Data

US 2023/0277793 A1 Sep. 7, 2023

Related U.S. Application Data

(63) Continuation of application No. 17/039,521, filed on Sep. 30, 2020, now Pat. No. 11,565,066, which is a (Continued)

(51) Int. Cl.
*A61M 16/06* (2006.01)
*A61M 16/20* (2006.01)

(52) U.S. Cl.
CPC ........ *A61M 16/0622* (2014.02); *A61M 16/06* (2013.01); *A61M 16/0627* (2014.02); (Continued)

(58) Field of Classification Search
CPC .......... A61M 16/0622; A61M 16/0627; A61M 16/06; A61M 16/0683; A61M 16/208; (Continued)

(56) References Cited

U.S. PATENT DOCUMENTS 35,257 A * 5/1862 Porter .................. A61M 16/18 128/204.13
746,089 A * 12/1903 Jessup ...................... B07B 1/10 209/384

(Continued)

FOREIGN PATENT DOCUMENTS

EP 1555039 A2 * 7/2005 ............ A61M 16/06
FR 2635454 2/1990

(Continued)

OTHER PUBLICATIONS

English translation for EP 1555039, machined translated by espacenet.com, translated on Jan. 23, 2025.*

(Continued)

*Primary Examiner* — Tu A Vo
(74) *Attorney, Agent, or Firm* — VIA LLP

(57) ABSTRACT

A customizable mask, and methods of forming such a mask, including a conforming seal is configured to utilize the physical process of granular jamming to enable it to adapt to a wide range of facial geometries. The mask may include a frame having a perimeter and a conduit connection, a conforming seal positioned along the perimeter of the frame; the conforming seal may include a sealing surface and a connecting surface, the connecting surface configured to mate with the perimeter of the frame, and the sealing surface configured to conform to a users' face. The conforming seal may further include an outer casing, granular material contained within the outer casing, and a vacuum connection. The mask may also include a similarly configured conforming frame.

21 Claims, 38 Drawing Sheets

Related U.S. Application Data continuation of application No. 15/309,768, filed as application No. PCT/NZ2015/050051 on May 8, 2015, now Pat. No. 10,828,450.

(60) Provisional application No. 62/117,370, filed on Feb. 17, 2015, provisional application No. 61/991,373, filed on May 9, 2014.

(52) U.S. Cl.
CPC ...... *A61M 16/0683* (2013.01); *A61M 16/208* (2013.01); *A61M 2016/0661* (2013.01); *A61M 2205/02* (2013.01); *A61M 2205/0216* (2013.01)

(58) Field of Classification Search
CPC ...... A61M 2016/0661; A61M 2205/02; A61M 2205/0216; A62B 18/084; A41D 13/1161
See application file for complete search history.

(56) References Cited

U.S. PATENT DOCUMENTS

| | | | | |
|---|---|---|---|---|
| 2,144,479 | A * | 1/1939 | Bloomheart | A62B 19/00 128/205.12 |
| 2,749,910 | A * | 6/1956 | Faulconer, Jr. | A61H 31/02 601/44 |
| 2,877,764 | A | 3/1959 | Galleher | |
| 4,022,200 | A | 5/1977 | Jonson | |
| 4,657,003 | A | 4/1987 | Wirtz | |
| 4,971,051 | A | 11/1990 | Toffolon | |
| 5,222,478 | A | 6/1993 | Scarberry et al. | |
| 5,243,971 | A * | 9/1993 | Sullivan | A61M 16/06 128/207.18 |
| 5,429,683 | A * | 7/1995 | Le Mitouard | A61M 16/0605 128/206.26 |
| 5,518,126 | A * | 5/1996 | Davis | A47L 15/505 248/499 |
| 6,418,929 | B1 | 7/2002 | Norfleet | |
| 6,494,206 | B1 * | 12/2002 | Bergamaschi | A61M 16/0605 128/206.24 |
| 6,834,650 | B1 | 12/2004 | Fini et al. | |
| 7,717,114 | B1 | 5/2010 | Laghi | |
| 7,971,590 | B2 | 7/2011 | Frater et al. | |
| 10,828,450 | B2 * | 11/2020 | Scheirlinck | A61M 16/0683 |
| 11,565,006 | B2 | 1/2023 | Scheirlinck et al. | |
| 2002/0185134 | A1 * | 12/2002 | Bishop | A61M 16/0688 128/206.25 |
| 2005/0284477 | A1 * | 12/2005 | Schrader | A61M 16/0616 128/205.25 |
| 2005/0284478 | A1 | 12/2005 | Meyer | |
| 2006/0185675 | A1 | 8/2006 | Colin | |
| 2006/0283461 | A1 | 12/2006 | Lubke et al. | |
| 2007/0107733 | A1 | 5/2007 | Ho et al. | |
| 2007/0163594 | A1 | 7/2007 | Ho et al. | |
| 2008/0289633 | A1 * | 11/2008 | Kwok | A61M 16/0825 128/206.24 |
| 2010/0000543 | A1 * | 1/2010 | Berthon-Jones | A61M 16/0605 128/206.26 |
| 2010/0319700 | A1 | 12/2010 | Ng et al. | |
| 2011/0088699 | A1 | 4/2011 | Skipper et al. | |
| 2011/0220114 | A1 | 9/2011 | Lithgow | |
| 2011/0247625 | A1 * | 10/2011 | Boussignac | A61M 16/0447 128/207.18 |
| 2012/0080035 | A1 * | 4/2012 | Guney | A61M 16/0616 128/205.25 |
| 2012/0132208 | A1 * | 5/2012 | Judson | A61M 16/0622 128/206.26 |
| 2012/0280421 | A1 | 11/2012 | Judson et al. | |
| 2013/0213400 | A1 | 8/2013 | Barlow et al. | |
| 2014/0216463 | A1 | 8/2014 | Cowell et al. | |
| 2014/0261440 | A1 | 9/2014 | Chodkowsk | |
| 2014/0283832 | A1 * | 9/2014 | Stegman | A61M 16/0003 128/205.25 |
| 2014/0283841 | A1 | 9/2014 | Chodkowski et al. | |
| 2014/0305439 | A1 * | 10/2014 | Chodkowski | A61M 16/0605 128/207.11 |
| 2015/0083124 | A1 | 3/2015 | Chodkowski et al. | |
| 2015/0283348 | A1 | 10/2015 | Harp et al. | |

FOREIGN PATENT DOCUMENTS

| | | | | |
|---|---|---|---|---|
| GB | 1439720 | | 6/1976 | |
| GB | 1439720 | A * | 6/1976 | A61M 16/06 |
| WO | 1993000125 | A1 | 1/1993 | |
| WO | 2009065368 | A1 | 5/2009 | |
| WO | WO 13/050911 | | 4/2013 | |
| WO | WO 13/076624 | | 5/2013 | |
| WO | WO 13/144753 | | 10/2013 | |

OTHER PUBLICATIONS

Brown et al., Nov. 2, 2010, Universal robotic gripper based on the jamming of granular materials, PHAS, 107(4):18809-18814.

Ciszewska et al., “Heterogeneous electrorheological fluids with liquid crystalline matrices”, 2009.

* cited by examiner

Outer Surface
144
112
122
140
102
100
130
Face 108
104
102
114
L
M
S
112,
130
S
M
L
122
100

122L
122M
122S
S
L
M 504
544
572
532
Inside
570a
576
Outside 504
572
544
512
Inside
532
530
574
Skin
576
570
Outside 100
102
V
104
2010
2014
2012
2008
S
H 2002
2006
2004
2000

CUSTOMIZABLE RESPIRATORY MASK

INCORPORATION BY REFERENCE TO ANY PRIORITY APPLICATIONS

Any and all applications for which a foreign or domestic priority claim is made are hereby incorporated by reference and made a part of the present disclosure.

BACKGROUND

Technical Field

The present embodiments relate to respiratory masks, including, for example, customizable respiratory masks.

Description of the Related Art

Respiratory masks are used for a variety of different therapies, including but not limited to non-invasive ventilation (NIV), oxygen therapy and continuous positive airway pressure (CPAP), for the treatment of various respiratory conditions. Many of these respiratory therapies require that a substantially airtight seal is achieved between a mask and a user. Due to the range of differing facial geometries in the population, it can be difficult to achieve a desired seal as a result of the mask geometry not matching the geometry of a user's face. It is common to apply substantial forces to a mask and user's face in an attempt to overcome any differences in geometry, and achieve a seal. The application of forces to a mask and thus a user's face can cause discomfort as well as injuries to the user and not always successful at attaining satisfactory leak rates.

For example, FIGS. 1 and 2 illustrate skin sores caused by existing respiratory masks. For a respiratory mask to be used in the provision of respiratory therapies such as NIV or CPAP the patient must be breathing spontaneously. In some cases, the patient is not lucid and thus not able to indicate discomfort or pain that may precede such injuries.

BRIEF SUMMARY

An aspect of at least one of the embodiments disclosed herein includes the realization that patient comfort can be improved and patient injuries caused by masks can be reduced by configuring a mask for adjustment of mask contours for accommodating faces that have different shapes and retaining the adjusted shape. For example, in some embodiments, a respiratory mask can include a jamming-enabled portion in at least one of a facial seal portion and/or a frame portion thereof. Such a mask, in some embodiments, can reduce the number of leaks and/or the leak rate to acceptable magnitudes or eliminate leaks altogether, and can also reduce forces on the user's skin ("skin pressure"), in particular areas of the face where the skin is thin such as the nasal bridge, for example.

Designing such masks presents several challenges, including accommodating differently sized and shaped faces, as well as minimizing the force of contact between the seal and the corresponding portions of each different user's face. Ideally, a mask will not leak with very low skin pressure. Leaks will occur, however, where the skin pressure is insufficient to counter the gaseous pressure differential between the inside and outside of the mask. Thus, when unacceptable leaking is found using a typical mask, the force on the entire mask (e.g., by way of a strap) is typically increased until leaks are reduced to an acceptable level or eliminated. However, such additional force also increases the force of contact between the seal and the user's face (skin pressure) at locations where no leaking occurred, thereby generating unnecessarily higher forces at some locations, which can cause discomfort and/or injury.

FIGS. 1 and 2 illustrate facial skin injuries suffered by patients who wore respiratory masks while receiving medical care. FIG. 1 illustrates a more generalized, inverted U-shaped injury 10 extending from the patient's cheeks and up and over the bridge of the nose. As shown in FIG. 1, the injury 10 includes larger regions 12, 14 lower down on the user's face and another larger portion 16 on the bridge of the patient's nose. Additionally, there are thinner, smaller regions 18, 20 lower down on the user's face, between the nose bridge injury area 16 and the lower larger portions 12, 14. As such, it appears that the mask causing this injury generated uneven forces around the patient's cheeks and nose bridge.

FIG. 2 illustrates a very localized injury 22 appearing only on the bridge of the nose of the patient. More severe injuries, such as that illustrated in FIG. 2, are more common in areas of the face where the skin is thin, i.e. where bone is close to skin i.e. the nasal bridge. These are the areas of the face that can experience the highest loads due to over tightening the headgear straps of the mask system. Excessive skin pressure can restrict blood flow, thereby starving the skin tissue of oxygen and nutrients and accelerating breakdown of the skin tissue.

With reference to FIGS. 2*a*-2*c*, the creation of leaks, discomfort, and/or disadvantages noted above can result from a sequence of events described below. For example, with reference to FIG. 2*a*, a mask 30 can include a frame 32 and a seal 34. The frame 32 and seal 34 can be attached to a user's face with straps 31, 33, adjusted to achieve a balance of comfort and leak rate, for example, the minimum forces required to achieve either no leaks or an acceptable leak rate.

During such a process, after a first attempt to fit the mask 30 on the patient's face, a leak can form anywhere along the seal 34, for example, in an area adjacent to the user's nose 36 and in the vicinity of a user's eye 38. Such a leak, for example, can allow air 42 from within the mask 30 to pass through a space between seal 34 and the patient's face, thereby directing the air 42 towards the patient's face, and sometimes towards the user's eye 38. Additionally, it is possible that air 42 leaking as such, can occur on only one side of the mask 30, for example, only on the patient's left side, as illustrated in FIG. 2*a*.

FIG. 2*b* illustrates a recessed contour 46 on the patient's face which can be considered the cause of the leak of the air 42. For example, the recess 46 can be a crease, fold, or line on the patient's face and thus, in this example, forms an open "leak zone."

In the sectional view of FIG. 2*c*, the leak zone 46 appears as a gap between the outer surface of the seal 34 and the patient's face 40, where air 42 from the inside of the mask 30 leaks through the leak zone 46, and outwardly from the mask 30.

In some circumstances, when such a leak occurs, a patient or healthcare worker may attempt to tighten the upper 31 and lower 33 straps on the left side of the patient, to thereby generate additional forces to reduce the size or eliminate the leak zone 46. Such asymmetric tightening may successfully reduce or eliminate such leaking, but may also cause unintended consequences.

For example, such asymmetrical tightening can result in unnecessary forces applied to the entire left hand side of the patient's face in order to fix one small region of a leak. Such asymmetric tightening can also unbalance the seal between the seal 34 of the mask and the patient's face, for example, between the left and right sides of the patient's face, such that it induces a leak in another area altogether. Such can be the beginning of a series of asymmetric tightenings to overcome leaks. Further, such repeated retightening of a mask can eventually lead to discomfort for the user and/or injury, such as those described above with reference to FIGS. 1 and 2.

An aspect of at least one of the embodiments disclosed herein includes the realization that such injuries are sometimes caused by tightening of a mask with the strap force, for example, on associated head straps, to form an effective seal between a patient's face and a mask which does not well-match the contours of the patient's face. Due to the variability of shapes and sizes of patient's faces, uneven skin pressure points can be generated, thereby causing skin sores and injuries of different shapes and sizes. Additionally, patients who are semi lucid and require respiratory assistance, such as with non-invasive ventilation (NIV) using a respiratory mask, cannot provide feedback on discomfort or pain during the mask fitting process. A nurse or clinician who is fitting a respiratory mask to such a patient, is unable to tell how tight the fit is.

An aspect of at least one of the embodiments disclosed herein includes the realization that by providing a respiratory mask with adjustability in at least one of an orientation of a sealing face and a frame portion, as well as the structure and functionality for retaining the frame and/or sealing face in an adjusted, state can help reduce patient discomfort and/or injury and reduce leak to an acceptable level.

By contrast, some known mask designs, in order to be fitted onto the face of a patient, are sometimes pressed or squeezed so as to achieve the desired seal along a user's cheek. For example, patients with larger nose bridges and longer or "pointy" faces, may require a mask to be pinched transverse to a vertical axis (e.g., the sides of the mask are rotated about a vertical axis), to cause the sides of the mask to better follow the patient's cheeks. This movement can be referred to as "clam-shelling." However, some known masks are made from resilient materials. Thus, when a mask is pinched in the "clam shelling" movement, the frame of the mask itself acts like a spring, storing elastic energy. In order to retain the mask in such a shape, head straps are used to resist the force of the spring forces generated by the mask frame. Similarly, mask seals are often made in a resilient structure, which also store some energy like a spring. Thus, the straps for retaining such known masks also must resist these forces as well.

An aspect of at least one of the embodiments disclosed herein includes the realization that providing for a structural and/or contour adjustability of a mask frame and/or seal can reduce or eliminate the requirement that head straps resist the stored spring energy in the mask or seal, and thereby reduce the overall required tension of head straps for holding a mask properly in sealing engagement with the face of a patient.

Thus in some embodiments, a customizable mask can include a mask frame and seal assembly configured to extend around a respiratory orifice of a patient, such as a nose and/or mouth. The frame can include a perimeter with a seal portion extending along the perimeter of the frame. The frame can also include a conduit connection which can be configured for connection to a respiratory apparatus, such as apparatuses for ventilation, oxygen therapy, and/or continuous positive airway pressure (CPAP). The seal portion can include a connecting surface and a sealing face, the connecting surface being configured to mate with the perimeter of the frame. The sealing face can be configured to form a seal with skin of a patient's face. At least one of the frame and seal portions can be fixable in a plurality of different configurations.

In some embodiments, at least one of the frame and seal portions includes a granular jamming portion which is configured to transition between a neutral flexible state and a "jammed" state (i.e., a substantially more rigid state as compared to the neutral flexible state). As such, at least one of the frame and seal portions can be manipulated so as to change its shape and then the jamming enabled portion can be transitioned to a jammed state so as to retain the frame or seal portion in the adjusted shape.

Thus, in some embodiments, a respiratory mask includes a frame portion and a seal portion. The frame portion can include a perimeter and a conduit connector for connecting to a gas source. The perimeter can be connected to the seal portion. The seal portion can include a sealing face configured to seal against the face of a patient. Additionally, at least one of the frame portion and the seal portion can include a variable stiffness device configured to transition between a lower stiffness state and a higher stiffness state, wherein the variable stiffness device included in the seal portion is configured to allow and retain an orientation of the sealing face of the seal portion.

In some embodiments, a customizable mask can include a conforming seal configured to utilize the physical process of granular jamming to enable it to adapt to a wide range of facial geometries. The mask can include a frame having a perimeter and a conduit connection, a conforming seal positioned along the perimeter of the frame; the conforming seal may include a sealing surface and a connecting surface, the connecting surface configured to mate with the perimeter of the frame, and the sealing surface configured to conform to a users' face. The conforming seal can further include an outer casing, granular material contained within the outer casing, and a vacuum connection. The mask may also include a similarly configured conforming frame. Further disclosed are methods of forming the mask.

Another aspect of at least one of the embodiments disclosed herein includes the realization that a clam shell-like behavior in a mask can be desirable as it can allow such a mask to be customized to a wider range of facial geometries. For example, a clam-shell configured mask can be more easily varied to match both flat and wide facial geometries (such as Asian faces), and deep and narrow facial geometries (European faces). The profile of the mask seal conforms to the depth of the nasal bridge and other facial features and becomes narrower or wider in response to this conformance.

Another aspect of at least one of the embodiments disclosed herein includes the realization that other configurations can also be used to achieve one or more of the above-described benefits as well as other optional benefits. For example, in some embodiments, a mask can include a seal portion which combines a relatively stiffer, plastically deformable portion and an inflatable portion disposed between the stiffer portion and the patient. The inflatable portion can provide optional additional benefits for improving seal performance.

In some configurations, a respiratory mask can be configured to fit a plurality of differently-shaped human faces. The mask can comprise a frame portion comprising a perimeter portion and a conduit connection portion. A seal portion can be connected to the perimeter portion of the frame, the seal comprising a sealing surface and a connecting surface, the connecting surface being connected to the perimeter portion, the sealing surface configured to form a seal with a portion of a human face. At least one of the frame portion and the seal portion can comprise a variable stiffness portion configured to selectively transition between a decreased stiffness state and an increased stiffness state.

In some configurations, wherein the frame portion is configured to extend over a respiratory orifice area of a plurality of differently-shaped human faces.

In some configurations, the variable stiffness portion comprises a density-dependent, variable viscosity material contained in a compressible chamber.

In some configurations, the variable viscosity material is a granular material.

In some configurations, the compressible chamber is an air-tight bladder configured to maintain a vacuum therein and so as to collapse against the granular material, increase the density thereof and thereby increase the viscosity of the granular material therein and transition the variable stiffness portion to the increased stiffness state.

In some configurations, a releasable one-way valve can be mounted to the air-tight bladder.

In some configurations, the variable stiffness portion is included in the seal portion and comprises an oblong cross section, a major axis of the oblong cross section extending along the width direction of the seal portion.

In some configurations, the variable stiffness portion is included in the seal portion and comprises an oblong cross section, a major axis of the oblong cross section extending along the thickness direction of the seal portion.

In some configurations, the variable stiffness portion is included in the seal portion, the variable stiffness portion defining at least about 60% of the seal portion.

In some configurations, the variable stiffness portion is included in the seal portion, and the variable stiffness portion extends across at least about substantially the entire width of the seal portion.

In some configurations, the variable stiffness portion is included in the seal portion and defines a layer of the seal portion.

In some configurations, the variable stiffness portion is included in the seal portion and comprises a plurality of variable stiffness layers.

In some configurations, the plurality of variable stiffness layers comprises at least first and second granular jamming chambers.

In some configurations, the first granular jamming chamber comprises first granules and the second granular jamming chamber comprise second granules, the first granules being different from the second granules.

In some configurations, the first and second granular jamming chambers are fluidically connected.

In some configurations, the variable stiffness portion is disposed in the seal portion between the perimeter portion of the frame and the sealing surface of the seal portion, the mask additionally comprising a cushion portion disposed between the variable stiffness portion and the sealing surface.

In some configurations, the variable stiffness portion comprises a granular jamming chamber.

In some configurations, the cushion portion comprises a gel.

In some configurations, the cushion portion comprises a flap connected to an outer surface of the seal portion and extending inwardly toward an interior of the mask.

In some configurations, the cushion portion comprises a lip connected to an outer surface of the seal portion and extending inwardly toward an interior of the mask.

In some configurations, the seal portion comprises at least one reinforcement strand extending along at least a portion of a length of the seal portion.

In some configurations, the at least one reinforcement strand extends along the entire length of the seal portion, forming a loop.

In some configurations, the frame comprises a seal support portion connected to the seal portion and is configured to be deformable through a clam-shelling movement.

In some configurations, the frame comprises at least first and second frame portions and at least a first flexible portion connecting the first and second frame portions and configured to allow the first and second frame portions to be moved relative to one another in the clam-shelling movement, wherein the first flexible portion comprises a variable stiffness portion, wherein the variable stiffness portion is configured to be selectively transitionable between a first more flexible state and a second less flexible state, wherein the variable stiffness portion comprises a granular jamming chamber.

In some configurations, the first and second frame portions are stiffer than the seal portion and wherein the first and second frame portions define at least a portion of the seal support portion.

In some configurations, the seal portion comprises an inflatable bladder disposed between the sealing surface and the connecting surface.

In some embodiments, a respiratory mask can be configured to fit a plurality of differently-shaped human faces. The mask can comprise a seal portion comprising a sealing surface and a connecting surface, the sealing surface configured to form to a seal with a portion of a human face disposed around a respiratory orifice of the human. A frame can comprise a conduit connection portion and a seal support portion connected to the connecting surface of the seal portion, the frame configured to be deformable through a clam-shelling movement.

In some configurations, the frame comprises at least a first and second frame portions and at least a first flexible portion connecting the first and second frame portions and configured to allow the first and second frame portions to be moved relative to one another in the clam-shelling movement.

In some configurations, the first flexible portion comprises a variable stiffness portion.

In some configurations, the variable stiffness portion is configured to be selectively transitionable between a first more flexible state and a second less flexible state.

In some configurations, the variable stiffness portion comprises a granular jamming chamber.

In some configurations, the granular jamming portion comprises granular jamming material, the frame being configured to be foldable through the clam-shelling movement, between a folded configuration and an unfolded configuration, the granular jamming material locking the frame in the folded position when the variable stiffness portion is transitioned to the second less flexible state.

In some configurations, the first and second frame portions are stiffer than the seal portion.

In some configurations, the first and second frame portions define at least a portion of the seal support portion.

In some configurations, frame comprises a first hinge.

In some configurations, the first hinge extends across a central portion of the frame.

In some configurations, the first hinge comprises a fabric material.

In some configurations, the frame further comprises a second hinge.

In some configurations, the seal portion comprises a variable stiffness seal portion.

In some configurations, the variable stiffness seal portion is configured to selectively transition between a decreased stiffness state and an increased stiffness state.

In some configurations, the frame comprises first and second frame portions connected so as to be moveable relative to one another in the clam shelling movement, the variable stiffness seal portion being connected to both the first and second frame portions.

In some configurations, the first and second frame portions are connected with a flexible frame portion, the variable stiffness seal portion extending across the flexible frame portion.

In some configurations, the first and second frame portions are connected with a flexible frame portion, the variable stiffness seal portion extending across the flexible frame portion.

In some configurations, the frame is configured to be deformable into a plurality of different orientations through the clam shelling movement, the variable stiffness seal portion being configured to retain the frame in the plurality of different orientations.

In some configurations, the seal portion comprises at least one reinforcement strand extending along at least a portion of a length of the seal portion.

In some configurations, the at least one reinforcement strand extends along the entire length of the seal portion, forming a loop.

In some embodiments, a respiratory mask can be configured to fit a plurality of differently-shaped human faces. The mask can comprise a frame portion comprising a perimeter portion and a conduit connection portion. A seal portion connected to the perimeter portion of the frame, the seal comprising a sealing surface and a connecting surface, the connecting surface being connected to the perimeter portion, the sealing surface configured to form a seal with a portion of a human face, the seal portion comprising a layer of granular material and an inflatable bladder, the layer of granular material being disposed between the frame and the inflatable bladder.

In some configurations, the frame portion is configured to extend over a respiratory orifice area of a plurality of differently-shaped human faces.

In some configurations, the layer of granular material comprises a density-dependent, variable viscosity material contained in a compressible chamber.

In some configurations, the compressible chamber is an air-tight bladder configured to maintain a vacuum therein and so as to collapse against the granular material, increase the density thereof and thereby increase the viscosity of the granular material therein and transition the variable stiffness portion to the increased stiffness state.

In some configurations, a releasable one-way valve can be mounted to the air-tight bladder.

In some embodiments, a respiratory mask can be configured to fit a plurality of differently-shaped human faces. The mask can comprise a frame portion comprising a perimeter portion and a conduit connection portion. A seal portion can be connected to the perimeter portion of the frame, the seal comprising a sealing surface and a connecting surface, the connecting surface being connected to the perimeter portion, the sealing surface configured to form a seal with a portion of a human face. At least one of the frame portion and the seal portion can comprise a granular chamber comprising a plurality of granules.

In some configurations, the frame portion is configured to extend over a respiratory orifice area of a plurality of differently-shaped human faces.

In some configurations, the plurality of granules comprise density-dependent, variable viscosity material contained in the granular chamber which comprises a compressed chamber.

In some configurations, the granular chamber is an air-tight bladder with an internal pressure below atmospheric pressure, squeezing walls of the granular chamber against the plurality of granules.

In some configurations, the granular chamber defines at least about 60% of the seal portion.

In some configurations, the granular chamber is included in the seal portion, and extends across at least about substantially the entire width of the seal portion.

In some configurations, the variable stiffness portion is included in the seal portion and defines a layer of the seal portion.

The term "comprising" is used in the specification and claims, means "consisting at least in part of". When interpreting a statement in this specification and claims that includes "comprising", features other than that or those prefaced by the term may also be present. Related terms such as "comprise" and "comprises" are to be interpreted in the same manner.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

DETAILED DESCRIPTION OF THE PREFERRED EMBODIMENT

The embodiments described below are described in the context of therapeutic fluid delivery devices which include seals designed to form seals with areas of patients encircling a target treatment area. However, the inventions disclosed herein can be applied to other devices designed for uses in other environments, including devices for non-medical uses, and uses on non-humans, and/or inanimate objects.

Figure 3:
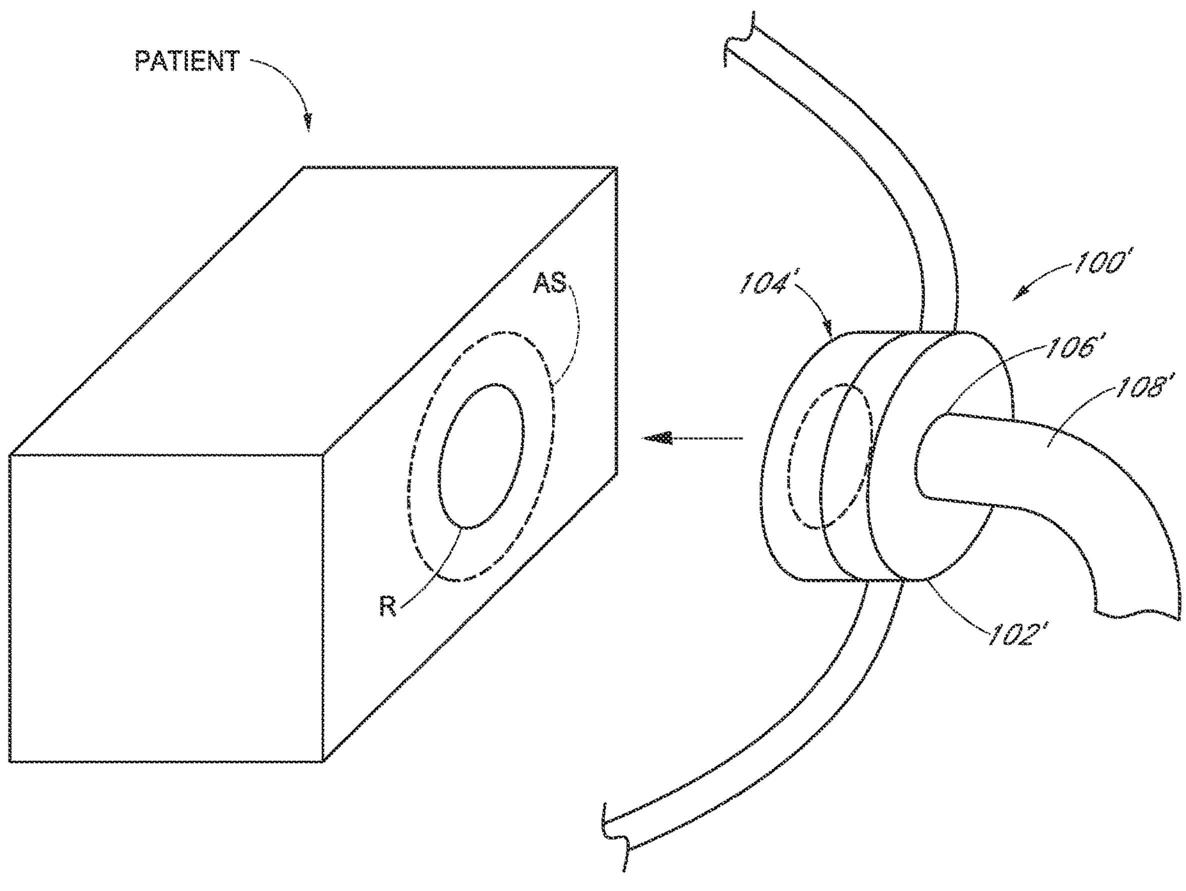
FIG. 3 is a schematic perspective and exploded view of a patient and a mask in accordance with an embodiment.

FIG. 3 schematically illustrates an embodiment of a mask 100' including a variable stiffness portion which provides improved compatibility with differently-shaped contours of a user or patient. The mask 100' includes a frame portion 102', a seal portion 104' and a conduit connection 106'. The frame portion 102' is configured to extend over a target portion R of a patient to be treated with the mask 100'. For example, but without limitation, the target area R can be an area of the patient's body, such as the patient's skin with an undesirable characteristic, such as disease, an incision, a wound or at least one respiratory orifice of a patient, which can be, for example but without limitation, the nostrils, nose, and/or mouth of a patient. The conduit connection 106' can be in the form of a connection for receiving or discharging fluids or solids. For example, the conduit connection 106' can be in the form of a respiratory conduit connection, which can optionally be incorporated into an aperture of the frame 102' to provide connection to a respiratory air conduit. The air conduit 108' can be of the type for supplying a flow of pressurized breathable gases to the mask 100'.

The mask 100', as noted above, can be configured for providing a sealing arrangement with respect to a target portion R of the patient's body, such as the skin, or one or any combination of a patient's respiratory orifices, such as one or both nostrils (e.g., nasal masks), the mouth (oral masks), tracheotomy incisions, as well as other types of wounds, incisions, orifices, or areas to be treated with the mask 100'. As such, the seal 104' can be configured to generate a seal with an area or portion of the patient AS surrounding any one or any combination of the target portions R noted above. The portion AS can be in the form of skin, hair, with or without or other structures intended to be left in place during use of the mask 100, such as a nasogastric tube. Additionally, in any of the above noted configurations, the mask 100' can also include one or any combination of the various features disclosed herein, including granular jamming, clam shelling, and other concepts described in greater detail below. For example, but without limitation, in embodiments where the mask 100' is in the form of a pillow-type nasal mask, the seal 104' can be in the form of a bulbous member configured to generate seals around the nares of a patient's nose. In such embodiments, the patient's nares corresponds to the respiratory orifice R of FIG. 3 and the skin tissue surrounding the patient's nares corresponds to the area AS of FIG. 3. Known nasal-type masks are commercially available in various forms, including the Pilairo Q and Opus 360 masks available from Fisher & Paykel Healthcare.

In some embodiments, the mask 100' can include at least one variable stiffness portion. Such a variable stiffness portion can be in the form of a granular jamming chamber configured to transition between different states of stiffness. For example, such a granular jamming chamber (not shown) can be incorporated into portions of the seal 104' positioned at or proximate to the portions of the seal 104' which contact the area AS. The use and transitioning of the granular jamming chamber of such embodiments can be the same or similar to the descriptions set forth below with regard to granular jamming of the other embodiments of the mask 100'.

Figures 4A, 4B, 4C:
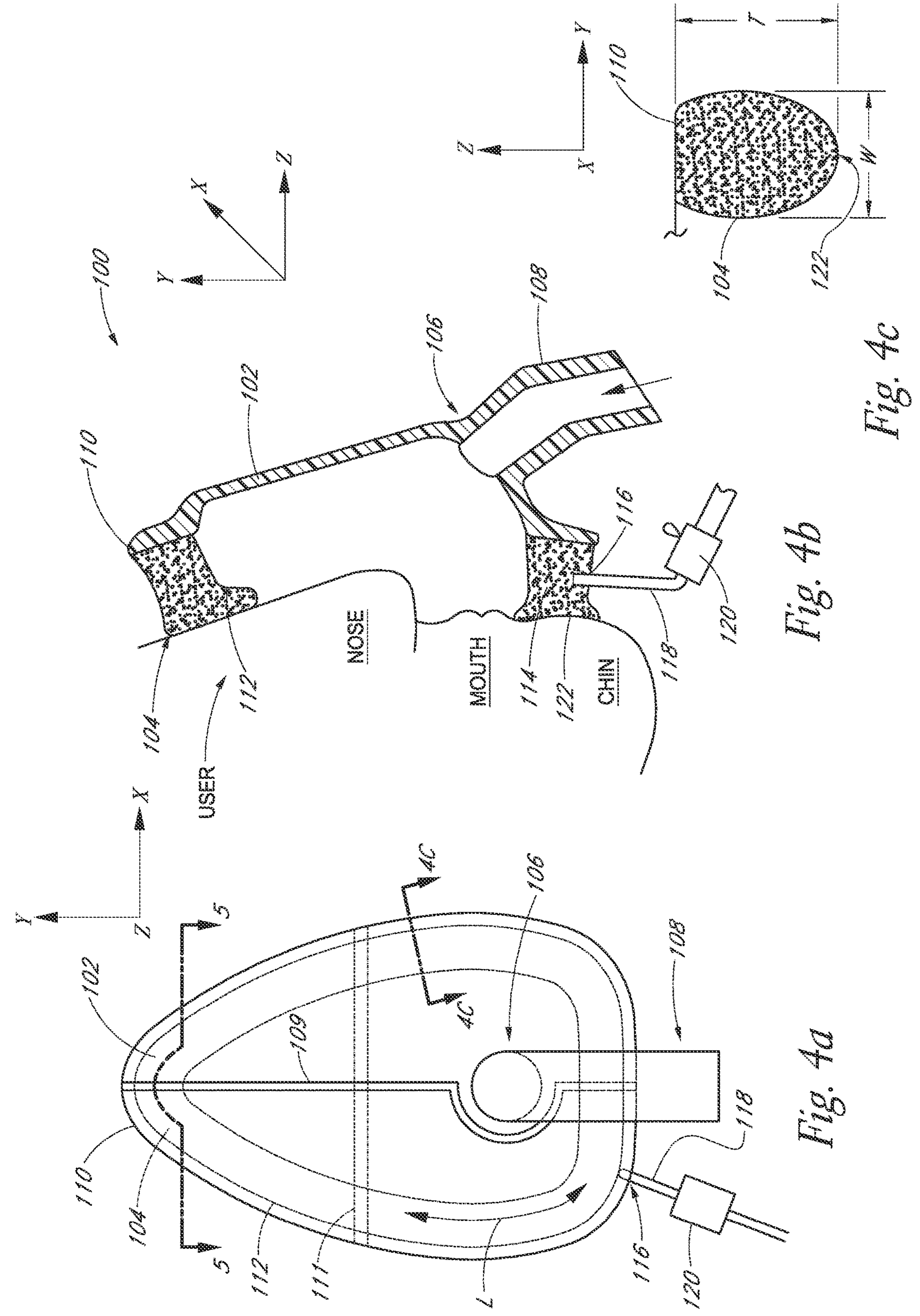
FIG. 4*a* is a schematic front elevational view of an embodiment of the mask of FIG. 3.
FIG. 4*b* is a partial side elevational and cross sectional view of the mask of FIG. 4*a* applied to a user.
FIG. 4*c* is an enlarged schematic cross section view of a portion of the mask illustrated in FIG. 4*a* taken along line 4*c*-4*c*.

FIGS. 4*a*, 4*b*, and 4*c*, illustrate a further embodiment of the mask 100', identified by the reference numeral 100. Parts, components and features of the mask 100 which are similar or the same as corresponding parts or features of the mask 100' are identified by the same reference numeral except that the "'" has been omitted.

The mask 100 is configured to extend over and form a seal with the skin surrounding a patient's nose and mouth. However, other configurations can also be used. The frame 102 also includes a perimeter portion 110. The perimeter portion is configured for connection to the seal portion 104.

The frame portion 102 can be substantially rigid. Thus, the seal portion 104 provides more flexibility for following the contours of the user's face so as to provide the desired seal during use. More particularly, the seal portion 104 is configured to form a substantially airtight connection with both the perimeter portion 110 of the frame as well as the skin surrounding the patient's nose and mouth. The connection between the perimeter portion 110 of the frame 102 and the seal portion 104 can be permanent or detachable.

In accordance with at least one of the embodiments disclosed herein, the seal portion 104 includes at least one variable stiffness portion therein. For example, the seal portion 104 of the mask 100 can be formed nearly entirely with materials or mechanisms that can be transitioned between different states of stiffness. In some embodiments, the entire seal portion 104 can be made from a single chamber and filled with particulate or granular materials, liquids, solutions, non-newtonian fluids or other materials. In some embodiments, the materials used are of the type that can be used in conjunction with a technique known as "granular jamming" in which the material transitions from a state of lower stiffness or lower viscosity (e.g., flowable, flexible, conformable) to a state of increased stiffness or increased viscosity (stiffer, hardened, rigid). Such granules can be small or large, can be circular or polygon or could have random or varied shapes. However, other techniques and materials can also be used.

As used herein, the term "width of the sealing surface 122" is intended to refer to the width measured in direction "W" as illustrated in FIG. 4*c*. In some areas along the length "L" (FIG. 4*a*) of the seal portion 104, the width W of the sealing surface 122 can lie generally in the X-Y plane identified in FIG. 4*c*, for example, when the seal portion 104 is a neutral state. However, other portions of the sealing surface 122 can extend into the Z-axis and when the sealing portion 104 is adjusted or conformed to a user's face, the orientation of the sealing surface 122 can be changed such that it extends along the Z-axis as well.

The term "thickness of the seal portion" is intended to refer to the dimension labeled as "T" in FIG. 4*c*. The thickness T of the seal portion 104 extends in the Z-dimension identified in FIG. 4*b*.

The term "length of the seal portion" is intended to refer to the length L of the seal portion 104 as measured around the periphery of the mask 100. The length L of the seal portion 104 does not normally extend only along a single plane and thus would normally extend along a "3-Dimensional" path around the periphery 110 of the mask 100.

The sealing surface 122 or "face" of the sealing portion 104 is the portion of the sealing portion 104 that is most proximal to the face of the patient, in the Z-axis direction. Portions of the sealing face 122 might approximately lie in the X-Y plane when in a neutral or relaxed state. However, one of the benefits of the designs disclosed herein is that the orientation of the sealing face 122, relative to the X-Y plane, can be adjusted and better stabilized in an adjusted shape with one or more of the embodiments disclosed herein, described in greater detail below with reference to FIGS. 5*c* and 5*d*.

Using these dimensional labels for reference, in some embodiments, the at least one variable stiffness portion of the seal portion 104 can extend along only a portion of the longitudinal length L of the seal portion 104 or along the entire length L of the seal portion 104.

Additionally, at least one variable stiffness portion of the seal portion 104 can include a part of the seal portion extending along substantially the entire width W of the seal portion 104. As used herein, the phrase "substantially an entire width of the seal portion" is intended to mean at least approximately 75% to 80% of the width W of the seal portion 104. Additionally, in some embodiments, at least one variable stiffness portion of the seal portion 104 can be in the form of one or more layers within the seal portion 104.

With continued reference to FIGS. 4*a* and 4 *b*, in some embodiments, the seal portion 104 includes an outer casing 112. The outer casing 112 can be made from various different materials. In some embodiments, the outer casing 112 can form a variable stiffness chamber, for example, forming a granular jamming variable stiffness device of the mask 100. For example, the outer casing 112 can be in the form of an airtight chamber filled with granular jamming material 114. As such, the outer casing 112 can include an actuation port 116 configured to allow air or gas or another fluid or liquid to be withdrawn from the interior of the outer casing 112, to thereby increase the density of the granular jamming material 114 and thus increase the stiffness of the seal portion 104.

For example, the mask 100 can further include a vacuum connection conduit 118 and a valve 120 through which suction can be applied, for example, to create a vacuum within the outer casing 112, to thereby reduce the fluid pressure within the outer casing 112 to a pressure below that of atmospheric, thereby allowing atmospheric air to squeeze the outer casing 112 and thereby increase the density of the granular jamming material 114 and thereby increase the stiffness of the seal portion 104. Optionally, the valve 120 can be in the form of a one-way check valve. Further, in some embodiments, the valve 120 can include a release mechanism, for example, a button, for "releasing" the vacuum, i.e., allowing air to flow back into the outer casing 112. Other techniques can also be used.

Optionally, in some embodiments, the frame 102 can include a more flexible portion 109, for example, in the form of a hinge or other device or connection that allows for deflection. As shown in FIG. 4*a*, the hinge 109 can extend along a vertical centerline of the frame 102. Other configurations can also be used, for example, multiple hinges 109 in various locations of the mask 100 can be used. Additionally, one or more hinges 109 can be made from various materials and can be provided with various optional functionalities. For example, one or more hinges 109 can be made from fabric or other flexible materials. Optionally, one or more hinges can be entirely or have one or more portions configured to be provide variable stiffness, described below. As such, the frame 102 can be more easily deflected or folded, at least partially, about an axis that is approximately along the vertical centerline of the frame 102. Such a flexible portion 109 can more easily accommodate a clam-shelling movement, described in greater detail below with reference to FIGS. 23 and 24. FIG. 4*a* shows an optional configuration in which the lower end of the flexible portion 109 extends around one side of the conduit connection 106. Other orientations and configurations of the flexible portion 109 can also be used. For example, FIG. 4*a* illustrates an optional orientation of a flexible portion 111 as extending generally horizontally. Other orientations and configurations can also be used.

Additionally, the variable stiffness functionality of the seal portion 104 described above can also function for securing or fixing the relative orientations of portions of the frame 102 disposed on opposite sides of the any of the flexible portions 109, 111. Additionally, as described in greater detail below with reference to FIG. 12, the frame 102 or the flexible portions 109, 111 can include or comprise variable stiffness devices and/or functionality, for example, in the form of granular jamming-enabled portions of the frame.

Figure 5B:
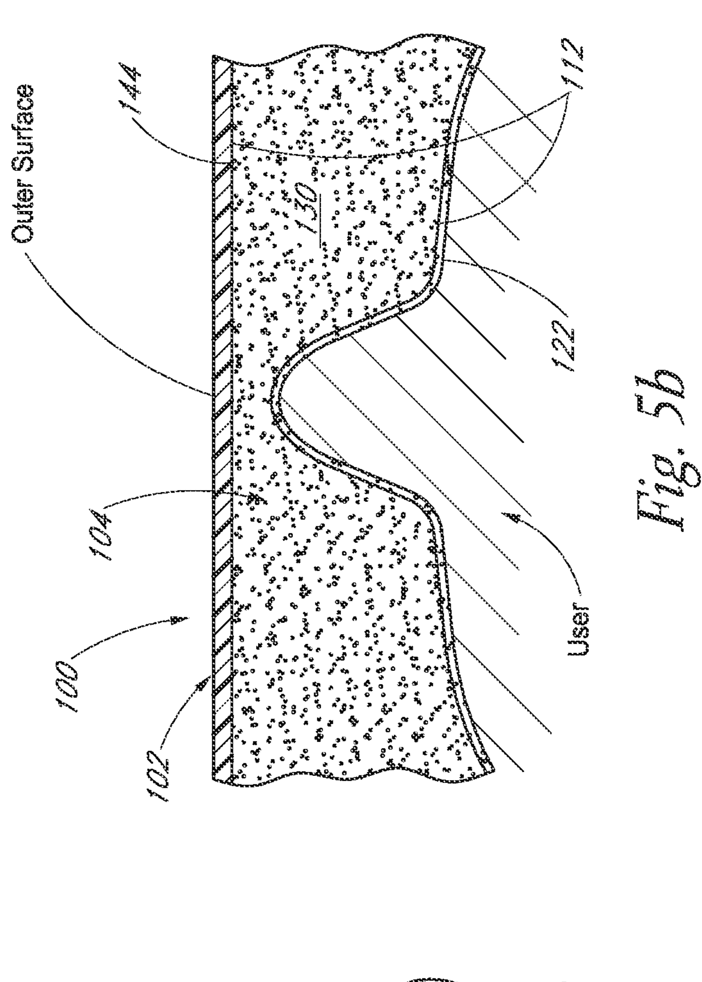
FIGS. 5*a* and 5*b* are schematic cross-sectional diagrams taken along line 5-5 of FIG. 4*a*, illustrating the mask applied to a face of a user having a flatter face and a user with a larger nose bridge and a more deeply contoured face.
Figure 5A:
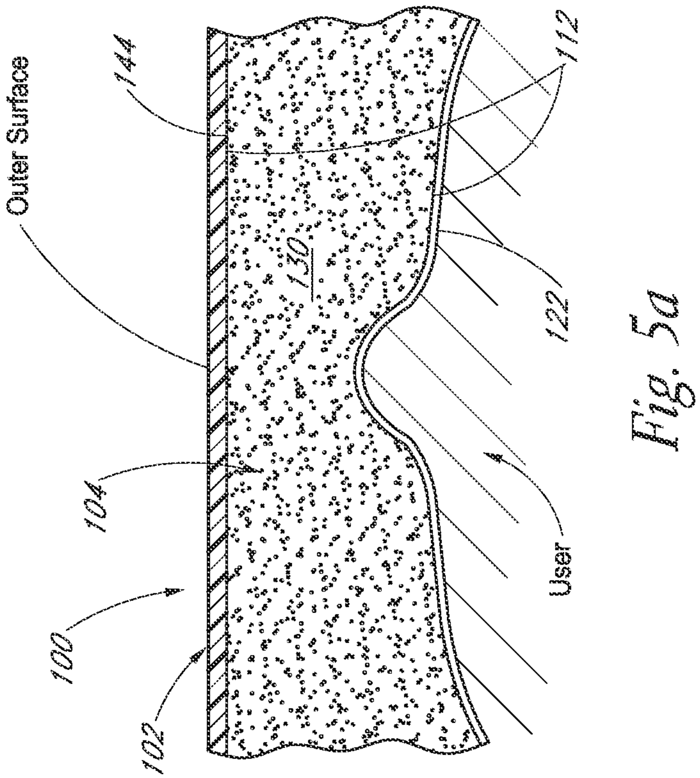
Figure 5D:
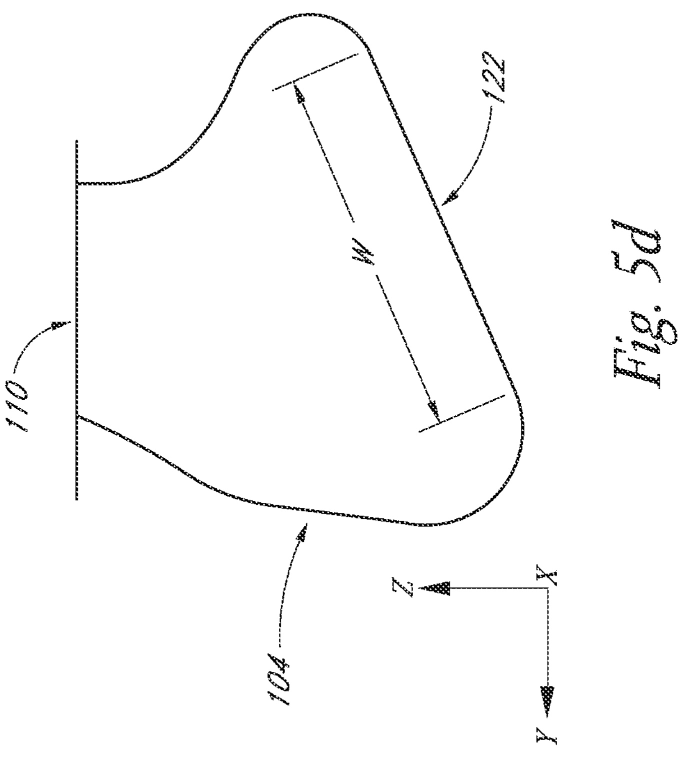
FIGS. 5*c* and 5*d* are schematic cross sectional views of a sealing portion of the masks of FIGS. 3-5, illustrating the adjustment of the orientation of the sealing surface of the seal portion.
Figure 5C:
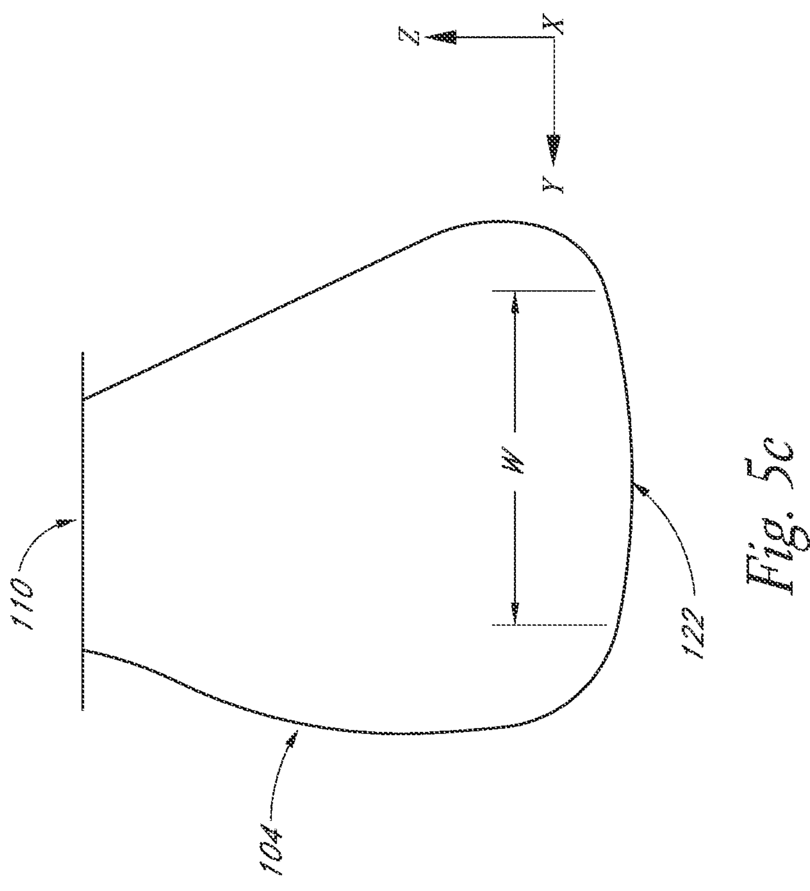

FIGS. 5*a* and 5*b* generally illustrate the concept of using a variable stiffness portion within the seal portion 104 to provide conformance with different shapes of patient faces. More specifically, FIGS. 5*a* and 5*b* generally correspond to the cross-section identified by the line 5-5 in FIG. 4*a*, showing a partial cross section through an area of the seal portion 104 and mask frame 102 extending over a bridge of a user's nose and across and onto portions of the patient's cheek adjacent to the nose bridge. The cross-section of FIGS. 5*a* and 5*b* are intended to pass through the sealing surface 122 between the seal portion 104 and skin of the user's face.

FIG. 5*a* illustrates the application of the mask 100 to a user having a flatter face with a shallower nose bridge which can also be referred to as a "flatter" facial geometry.

By contrast, FIG. 5*b* illustrates the application of the mask 100 to a patient having a much larger nose and more pointed face. By including at least one variable stiffness portion in the mask 100, the mask 100 can better conform to such different facial geometries.

In some embodiments, in the process of conforming to the contours of a user's face, the sealing surface 122 can be moved from a neutral state (FIG. 5*c*), in which in the illustrated example the sealing surface 122 extends generally along the X-Y plane, to a conformed state in which the sealing surface 122 is distorted out of the X-Y plane. The variable stiffness portion of the sealing portion 104, can then be transitioned into the jammed state, so as to preserve the adjusted/distorted orientation of the sealing surface 122 to better conform to a particular user's facial contours. Similarly, adjustments and distortions in the X-Z plane can also be made and preserved. In some embodiments, such enhanced conformability can be achieved by forming the entire seal portion 104 with a variable stiffness functionality, forming at least about 60%-80% of the seal portion 104 with a variable stiffness functionality. The proportion of the variable stiffness portion to the overall size of the seal 104 can depend on various factors including the type of devices used to form the variable stiffness portion. Here granular jamming is used, such factors can include the material used whether fluids or solids, the size of the particulates or granules, the shapes of those materials, the coefficient of friction between pieces of those materials, and other factors. In some embodiments, the seal 104 can include at least one or more layers having variable stiffness functionality. Optionally, the seal 104 can include a variable stiffness portion that extends across at least about 75-80% of the width of the sealing surface 122, or with other structures, devices, or functionalities.

For example as noted above, the at least one variable stiffness portion of the mask 100 can operate on the principle known as "granular jamming" to better enable the mask to adapt to a wider range of facial geometries. "Jamming" is a process where materials can have an initial fluid characteristic in a neutral state, in which the material can flow, move, or deform relatively freely, then pass through a transition phase to become more rigid or stiffer, caused by an increase in density of the material. The transition of the material between a neutral and rigid state can be referred to as the "jamming transition."

The jamming transition can be described as a type of phase transition, with similarities to a glass transition but different from the formation of crystalline solids. For example, while a glass transition occurs when the liquid state is cooled, the jamming transition happens when the density of the material is increased. As the density of the material increases, the constituent particles, which can be in the form of particulates, granules or other materials which may or may not be suspended in a gaseous or liquid fluid, crowd together which prevents them from exploring phase space, making the aggregate material become stiffer, less flexible, less deformable and thus behave more as a solid. FIG. 6*d* includes a jamming phase diagram relating jamming transition to inverse density, stress and temperature.

The density at which systems jam is determined by many factors, including the shape of their components, the deformability of the particles, frictional inter-particle forces, and the degree of dispersity of the system. For example, a static sand pile can be considered as being "jammed" under the force of gravity while no energy is being dissipated. Systems which are consuming energy are also sometimes described as being "jammed". An example is traffic jams, where due to jamming the average velocity of cars on a road may drop sharply. Here the cars on a road may be thought of as like a granular material or a non-newtonian fluid that is being pumped through a tube. Under certain conditions, such as increased pressure causing increased density, the effective viscosity of the non-newtonian fluid may rapidly increase, dramatically increasing the granular material or fluid's resistance to flowing and so causing the velocity to drop or even come to a complete stop. In the traffic jam analogy, the cars are like the grains in a granular material and if they are dense enough (i.e., closely enough spaced along the road) then interactions between the cars (as they must avoid each other to avoid crashing) cause jamming. A simple model of this behavior is the Nagel-Schreckenberg model.

There are several factors that can contribute to when granular material reaches a jammed phase or rigid state. These include but are not limited to, the size and shape of the granules of the material. The jamming transition can be induced by reducing the volume of fluid pressure of the volume within which the granular material is contained, thereby increasing the density.

Figure 6C:
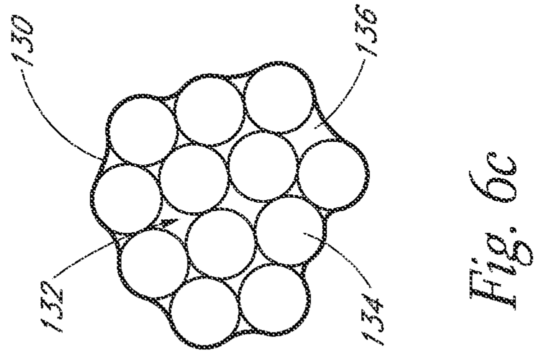
FIGS. 6*a*, 6*b* and 6*c* are schematic views illustrating a variable stiffness device transitioning from a state of lower stiffness to higher stiffness.
Figure 6B:
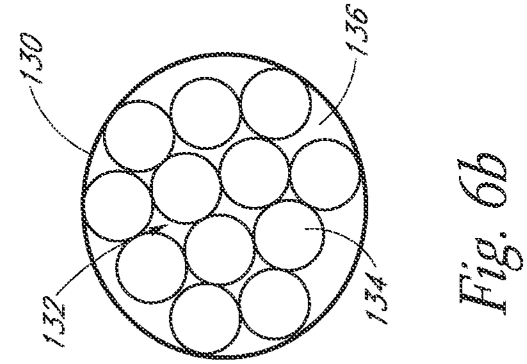
Figure 6A:
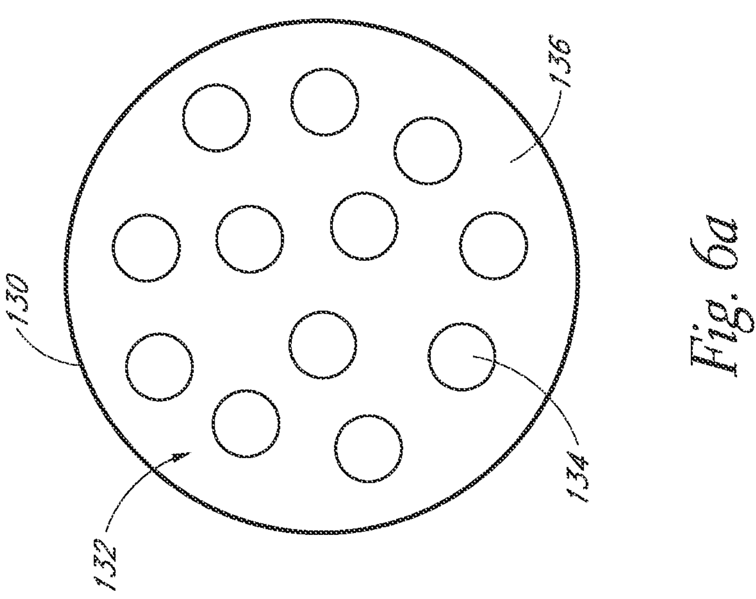
Figure 6D:
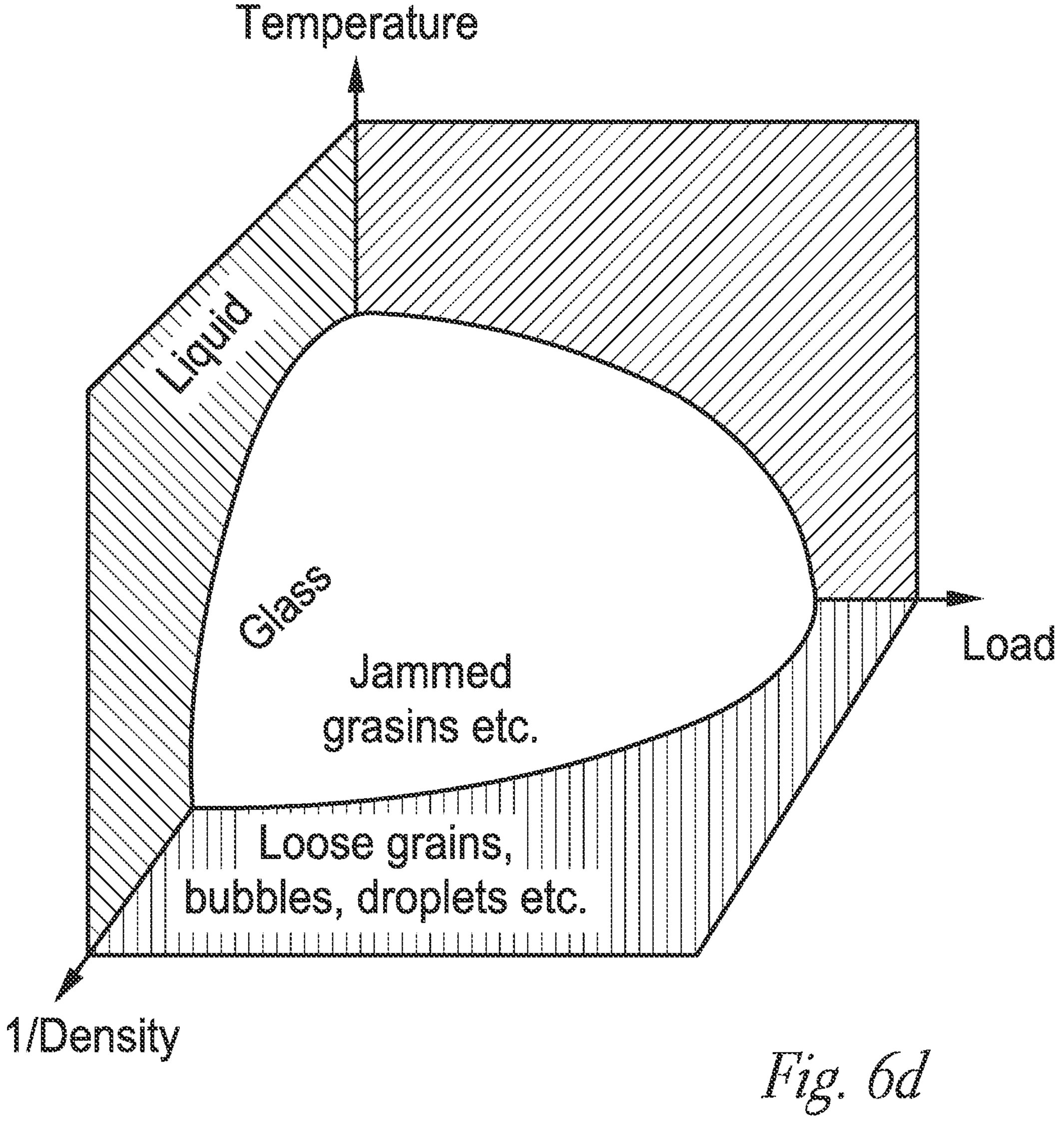
FIG. 6*d* is a phase diagram relating jamming transition to inverse density, stress and temperature.

FIGS. 6*a*-6*c* are schematic views illustrating how a granular jamming process can occur. In all three FIGS. 6*a*, 6*b*, and 6*c*, a granular material 132 including a fixed number of granules 134, are confined within a container 130 along with a fluid 136, such as air or another gas. In FIG. 6*a*, the container 130 forms a chamber with an initial or "neutral" volume that allows for relatively free movement of the granules 134 of the granular material 132. Because there is some excess volume within the container 130, the granules 134 are more free to move, in a fluid-like neutral state.

FIG. 6*b* illustrates a state in which some of the fluid 136 has been removed, for example, by application of a vacuum. The reduced volume of the chamber 130 forces the granules 134 into more contact with each other such that they may begin to "jam" together as a result of the reduced shape or volume of the chamber 130 and frictional forces between the granules 134.

With continued reference to FIG. 6*b*, with the reduced volume of the chamber 130, the granules 134 may achieve a semi-rigid state during the transition into the jamming phase. With further removal of fluid 136 from the chamber 130, the granules 134 can be pressed together into an even greater density state until they achieve a rigid state or significantly increased viscosity.

FIG. 6*c* can be considered as illustrating a "jammed" state wherein the granular material 132 is substantially rigid. Depending on the arrangement of the granules 134 when the volume of the chamber 130 is reduced, a nearly infinite array of different configurations is possible. Further, with the use of some types of granules 134 and the use of more flexible materials for forming the chamber 130, even in the state illustrated in FIG. 6*c*, the chamber 130 can remain somewhat flexible or elastic. For example, the granules can be in the form of talcum powder, sands, materials commercially available under the trade name Sands Alive!™, or other solids/granular material. Thus, depending on the materials chosen, it can be possible to change the overall shape of the chamber 134 when in a jammed state, by applying a force great enough to overcome the frictional forces between the granules 134.

Using such a structure as schematically illustrated in FIGS. 6*a*-6*c*, including a collapsible chamber 130 and granular material 132, in at least a portion of a frame 102 or a seal portion 104 of a mask 100, the mask 100 can be made to better conform to a variety of different facial geometries of patients, such as human faces. Thus, the mask 100 can be applied or pressed against a face of a user when in a neutral state, (the state illustrated in FIG. 6*a*. Pressing the mask as such against a patient's face, can deform the chamber 130, re-arrange the sealing surface 122, as well as other corresponding flexible portions of a mask such as the mask frame 102. With portions of the mask 100 deformed as such, the chamber 130 can be collapsed so as to transition the granular material 132 into a partially or fully jammed state. As such, the mask 100 would then be in a deformed state having contours that more closely match the contours of the patient's face, however, the mask 100 would be in a more neutral state in that additional external forces are not necessary to maintain the mask 100 in the deformed state. Rather, the variable stiffness portion, which may operate under the principle of granular jamming described above, maintains the mask 100 in the deformed state. With the mask 100 deformed as such, the mask can then be applied to a user's face, for example, with typical head straps, to provide a more continuous and even pressured seal around one or more respiratory orifices of a patient, i.e., the nose and/or mouth of a patient. As such the mask 100 can provide the following, or other, benefits:

Alleviation of pressure points by allowing mask retention forces to be spread evenly over the mask, also the seal may be less likely to collapse and allow the mask frame to bottom-out on the user's face, Reduced skin pressure and leaks during use, Reduced occurrences of shear force being applied to the face, since the seal is unlikely to deform in use, Improved seal, as a result of the mask being less likely to deform when the user moves or when an external force, such as hose drag, is applied, and Improved patient compliance.

Improved conformance to components such as nasogastric tubes.

The above-described jamming transition can be induced with any of the above-described variable stiffness portions of the mask 100, such as the seal portion 104 or any other portion of the mask 100, by removing a fluid such as air, or any other suitable fluid, from the spaces between the granules 134 so as to reduce the internal volume of the associated chamber 130. As such, the overall density of the granules 134 within the chamber 130 is increased. This can be achieved through the application of a negative pressure or vacuum to the chamber 130, or other mask element.

As used herein, the term "negative pressure" shall mean any pressure below atmospheric pressure. "Positive pressure" is intended to mean any pressure above atmospheric pressure.

The chamber 130 can be made of any flexible and/or elastic material such as, but not limited to, silicone rubber or thermoplastic elastomers, enabling it to conform readily to the facial geometry of a user and additionally to reduce in volume when a negative pressure is applied. Forming the chamber 130 with a flexible elastic outer casing can help such a variable stiffness portion or device achieve a more complete jammed state because the material forming the chamber 130 can expand and contract and conform to the surfaces of the granules 134 which it contacts. This can provide the additional optional benefit of achieving a more rigid state that better maintains a conformed shape. Additionally, the granular material 132 within the chamber 130 can freely move and conform to a user's facial geometry when in a substantially fluid, neutral state. Thus, the selection of fine granular material 132 can enable the conforming seal to more closely match the facial geometry of a user.

In some embodiments, the chamber 130 can be formed of a flexible but inelastic or substantially inelastic material. Use of such a material can result in the chamber 130 reaching an even more rigid state when in a fully jammed condition, however, may form creases in the outer surface of the chamber 130.

With continued reference to FIGS. 6*a*-6*c*, the granules 134 can be rounded. Rounded granules can slide more freely past one another and result in a less rigid seal when in a jammed state. When rounded granules 134 are in a neutral (un-jammed) state they have greater freedom of movement which allows them to conform more readily to the facial geometry of a user. Additionally, rounded granules 134 can also induce a pinching (clamshell) movement in the sides of the seal. Clam-shell movements are described in greater detail below with reference to FIGS. 23 and 24.

In some embodiments, the granules 134 forming the granular material 132 can have different hardnesses. Optionally, the granules can have different hardnesses in different regions of the seal portion 104.

Some of the granules 134 can comprise a soft and compressible material that is capable of undergoing elastic deformation. In some embodiments, sections of the seal portion 104 can have granules 134 with more elastic properties which can provide additional benefits. Optionally, all of the granules 134 can be soft or can comprise a mix of harder and softer granules. Although the softer granules included in the granules 134 generate greater resistance against sliding and flowing over one another in the jammed state, they can individually and collectively deform elastically, and thereby partially and elastically absorb some movements of a user's face, such as when the user moves their jaw, and better minimize leaks during and after such movements, elastically returning to the original shaped determined by the jamming process. Additionally, when under vacuum pressure, the softer granules 134 can conform to the geometry of the users face, but not as closely as the incompressible granular material.

For example, when some configurations of a seal portion 104 including only harder incompressible granules have been shaped to a user's face and subject to a vacuum to transition completely or partially to a jammed state, necking can occur in the seal portion 104 when the seal portion 104 is deformed, for example, when a user moves their jaw. The necking can result from the movement by the user (moving their jaw) overcoming the friction between the granules 134 and forcing some of the granules 134 to move from their conformed position to a different position, thereby changing the shape and/or configuration of the sealing surface 122. Such necking can occur due to tension on the seal 104 (for example, in the direction of the length L identified in FIG. 4*a*) as the patient moves their jaw. This can happen during fitting or other conditions when there is a tension. This necking can also occur in shear, e.g. while fitting with the skin, there can be a shear force introduced with the skin and cushion. As such, the conformed shape of the sealing surface 122 can be compromised because the harder granules 134 can inhibit or reduce the ability of the seal 104 to return to the pre-necking shape.

By contrast, using at least some softer granules 134 or including regions with at least some softer granules 134 in the seal portion 104, such forces (e.g., caused by movement of a user's jaw) can result in some necking in these regions and the granules 134 at least partially stretching elastically and thus better able to return entirely or substantially to the previously conformed shape, after the user stops moving their jaw. This allows the user to move their jaw (such as during yawning) whilst wearing the mask, without their movement being restricted and the seal being compromised. In some embodiments, the incompressible material and the compressible material can be separated within the seal so that they do not intermingle. In some embodiments, the different regions of differing granule hardnesses can be separated into layers. Additionally, the different regions can be separated into segments extending longitudinally along the seal portion.

Figures 7A, 7B, 7C, 7D:
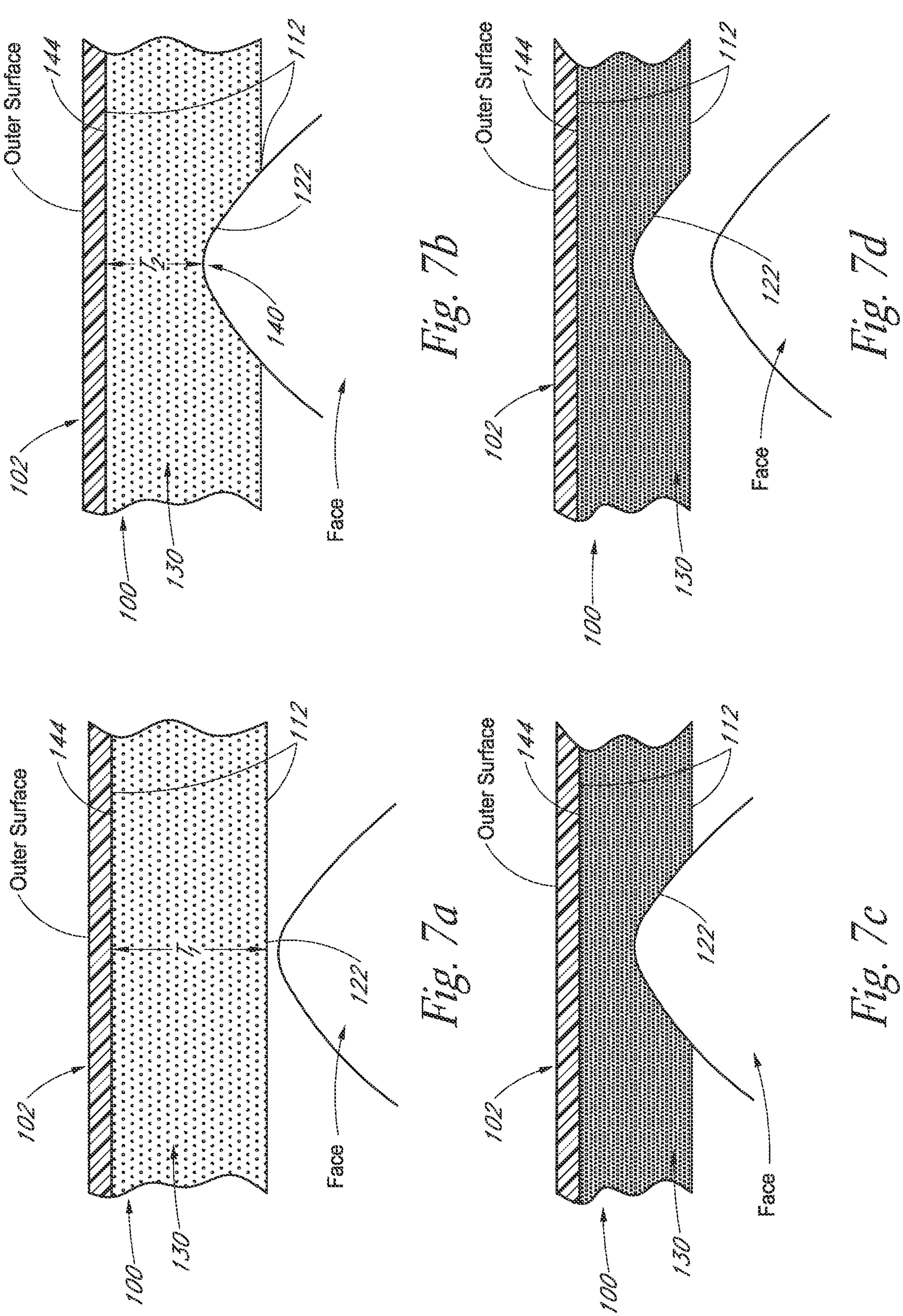
FIGS. 7*a*-7*d* are schematic cross-sectional views of a mask illustrating the process of adapting a mask to the shape of a particular user and transitioning the variable stiffness device from a state of lower stiffness to higher stiffness.

FIGS. 7*a*, 7*b*, 7*c* and 7*d* are a series of figures illustrating a method which can be used to conform a mask 100 to a patient's face, under varying conditions. Firstly, FIG. 7*a* shows the mask 100 in a neutral state as it could be prior to application to a user's face. At this point, the chamber 130 has a thickness Ti.

FIG. 7*b* shows the mask 100 having been pressed against a user's face, thereby deforming the chamber 130 so as to have a reduced thickness Ta. Because the chamber 130 and the granular material therein are in a neutral state, the compression of the chamber 130 as illustrated in FIG. 7*b* does not apply a substantially greater force against the user's face at the apex 140 of the illustrated contour of the patient's face, the point at which the thickness of the chamber 130 has been reduced to thickness Ta.

FIG. 7*c* illustrates a state of the mask 100 after a vacuum has been applied to the chamber 130. More specifically, a vacuum had been applied to the chamber 130 so as to remove excess air from within the chamber 130, thus causing the granular material 132 within the chamber 130 to achieve a jammed state.

FIG. 7*d* illustrates how the chamber 130 maintains the deformed shape achieved during the jamming state described above with reference to FIG. 7*c*, even after having been removed from the user's face. Thus, generally, a method for conforming the seal portion 104 of the mask 100 to a patient's face can include the following steps:

1. Appling the mask 100 to a user's face, with the mask 100 in a neutral state.

2. Conforming the granular material within the chamber 130 and the mask to a user's facial geometry, while in a neutral state.
3. Applying a negative pressure to the chamber 130, thus reducing the volume of the chamber 130 and increasing the density of the granular material 132 within the chamber 130. As such, the vacuum causes the chamber 130 to shrink and thus causes the seal portion 104 to shrink onto the user's face, with the chamber 130 becoming substantially rigid and retaining the shape of the user's face.

In some embodiments, a mask constructed as such can include a mechanism for releasing the vacuum, i.e., allowing atmospheric air to flow back into the chamber 130, thereby allowing the chamber 130 to return to a neutral state. Thus, a mask 100 that includes such a feature can be reconfigured many times to suit different users or different situations. The granular jamming process, in other words, can be reversed to allow the mask 100 to transition from the jammed state back to a neutral state, in which the mask is again flexible. The reversal of the jamming process can be achieved by releasing the applied vacuum and allowing the pressure within the chamber 130 to return to a level at which the granular material achieves a neutral state, or by providing a positive flow of air into the chamber 130 to speed the process of transitioning back to the neutral state.

Figures 8, 9:
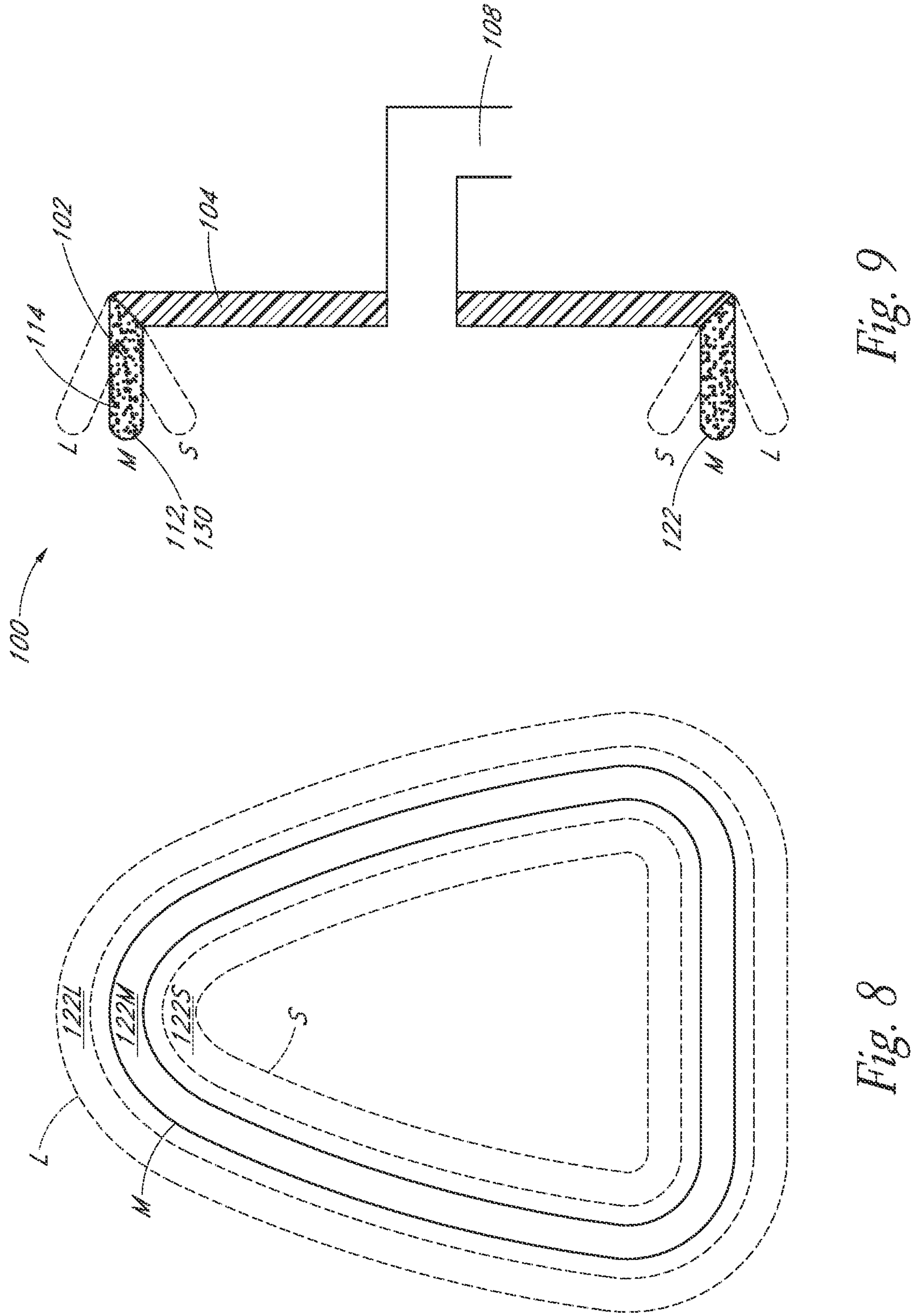
FIG. 8 is a schematic rear elevational view of the mask with different configurations illustrated in phantom line.
FIG. 9 is a schematic side elevational and partial cross sectional view of the mask in the three different orientations of FIG. 8.

With reference to FIGS. 8 and 9, in embodiments where seal portion 104 forms the chamber 130 and is made from an elastic material, the seal portion 104 can be enlarged and contracted in such a way such that the sealing surface 122 of the seal portion 104 can be made larger or smaller, for example, in a plurality of different sizes that can be described as concentric relative to one another. For example, as shown in FIGS. 8 and 9, the seal portion 104 can be designed to remain in a neutral state in the shape identified with the letter M, corresponding to a "medium" size. Thus, where the outer casing 112, which in this embodiment, can form the chamber 130, is made from an elastic material, the seal portion 104 can be enlarged into the shape identified by the letter L corresponding to a "large" size. Similarly, the seal portion 104 can be contracted into a smaller shape, corresponding to the shape identified as S corresponding to a "small" size. As such, the sealing surface 122 changes size and shape, illustrated as 122L for the large size, 122M for the medium size, and 122S for the small size.

Enlarged or contracted as such, and applied to a user's face, a vacuum can be applied to the chamber 130, thereby transitioning the chamber to a jammed state such that seal portion 104 can maintain the shape corresponding to one of the three sizes illustrated small, medium, large, or any size there between.

The ability to modify the size of the mask 100 can also be used to provide different sealing arrangements. For example, in full-face mask embodiments, where the seal portion 104 is configured to fit around a user's nose and mouth, it may be beneficial to be able to change the arrangement of the seal portion 104 to sit above or below the chin of the user. This can improve user comfort and compliance.

Figures 10A, 10B:
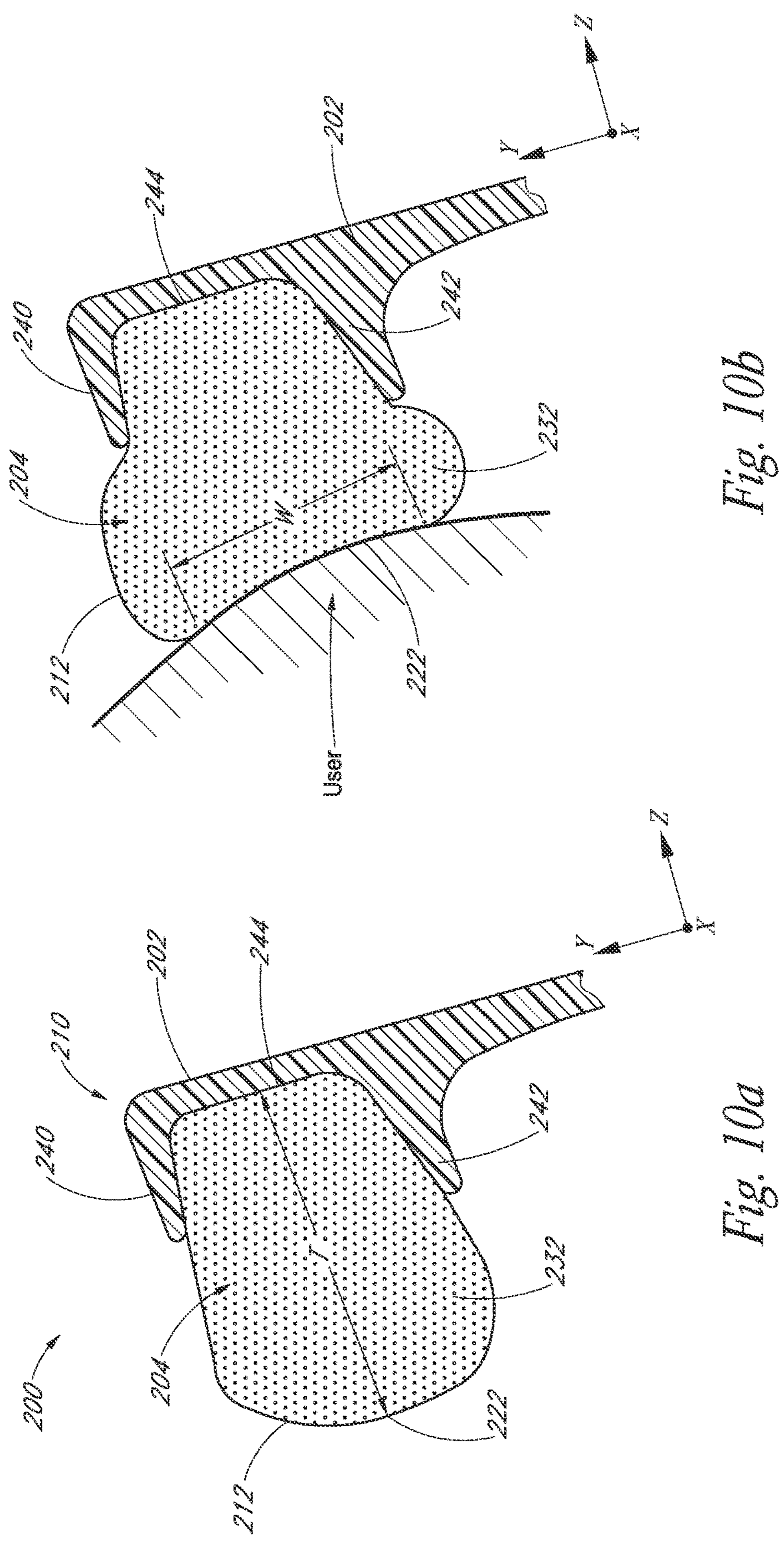
FIGS. 10*a* and 10*b* are cross-sectional views of a further embodiment of the mask including support walls, FIG. 10*a* illustrating the mask in a neutral state and FIG. 10*b* illustrating the mask applied to a user's face.

FIGS. 10*a* and 10*b* illustrate a modification of the mask 100 and is identified generally by the reference numeral 200. Parts, components and features of the mask 200 which are similar or the same as corresponding parts or features of the mask 100 are identified by the same reference numeral except that a value of 100 has been added thereto.

With reference to FIG. 10*a*, the mask 200 can include a modified frame 202, and in particular, a modified perimeter 210 relative to the perimeter 110 of the mask 100. More specifically, the perimeter portion 210 of the mask 200 includes outer support wall 240 and inner support wall 242. The outer and inner support walls 240, 242 can extend around the entirety or only a portion of the perimeter 210 of the frame 202. The outer and inner support walls 240, 242 can be made from the same material as the frame 202. Additionally, the outer and inner support walls 240, 242 can extend generally parallel to one another and thus form a channel around the perimeter 210 of the frame 202. Disposed between the outer and inner support walls 240, 242, the frame can include a connecting surface 244.

The connecting surface 244 can be used with or without the inwardly facing surfaces of the outer support wall and inner support wall 240, 242 to form a connection to the seal portion 204. In the illustrated configuration, the outer and inner support walls 240, 242 extend generally along the thickness T of the seal portion 204. As such, the outer and inner support walls 240, 242 can aid in providing an additional optional benefit of limiting the deformation of the seal portion 204 when the seal portion 204 is in a neutral conforming state.

For example, the outer and inner support walls 240, 242 can reduce or eliminate the likelihood that the seal portion can become completely "bottomed out" or in other words deformed to the point where the thickness T could be reduced to zero or near zero, with virtually little or no granular material 232 between the sealing surface 222 and the connecting surface 244. If such a bottoming out occurs, the stiffness of the associated portion of the seal portion 204 would not be significantly raised by the jamming process. This is because without the granular material located in such a pinched portion of the seal portion 204, the frictional forces between the granules 234 would not be present to provide the stiffening associated with a granular jamming principle of operation.

Additionally, the outer and inner support walls 240, 242 can help concentrate the "z axis" deformation of the seal portion 204. In other words, the outer and inner walls 240, 242 can resist the widening of the seal portion 204 disposed between the outer and inner walls 240, 242 thereby concentrating more of the expansion of the seal portion 204 and thus the width W of the sealing surface 222, as illustrated in FIG. 10*b*. As such, the portion of the sealing surface 222 in contact with the skin of the user grows, thereby creating a larger contact patch between the seal portion 204 and the skin of the user. FIGS. 10*a* and 10*b* also illustrate how the sealing surface 222 in the neutral state (FIG. 10*a*) is reshaped and oriented to follow a curved shape along an arc (FIG. 10*b*) that is distorted out of the X-Y plane, into the Z-axis. Additionally, FIGS. 10*a* and 10*b* illustrate that the sealing surface 222, when in a neural state (FIG. 10*a*) can have a convex shape and when in a conformed and jammed state (FIG. 10*b*) can have a concave shape, thereby providing enhanced conformability.

Further, along the lines discussed above with the manner in which the seal portion 204 enlarged as noted above with regard to FIG. 10*b*, the enlargement of the sealing surface 222 and the other surrounding portion of the seal portion 204 proximal to the user's face can also help prevent any part of the frame 202 from contacting the user's face and causing associated discomfort.

With continued reference to FIGS. 10*a* and 10*b*, the outer and inner support walls 240, 242 can be configured to be a semi-rigid or substantially rigid extension of the frame 202. For example, the connecting surface of the seal portion 204 is disposed between the outer and inner walls 240, 242 and thus can act as a retention for the seal portion 204.

FIG. 10*b* shows the seal portion 204 being deformed from a neutral state, as being pressed against a user's face. As such, the deformation generally occurs outside of the support walls 240, 242. During a jamming transition, the seal portion 204 can shrink while maintaining a substantially similar geometry to that shown in FIG. 10*b*.

Figures 11A, 11B:
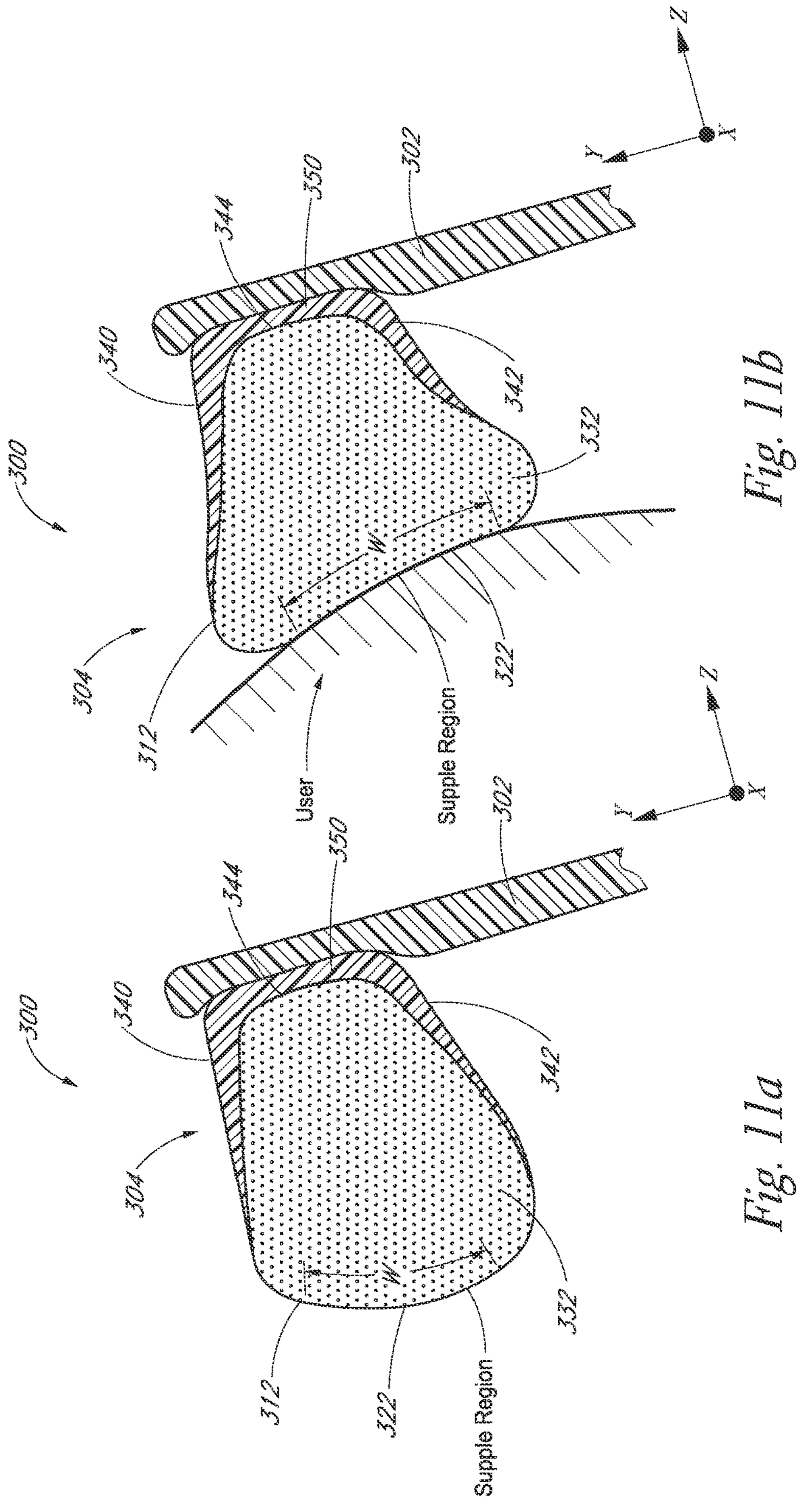
FIGS. 11*a* and 11*b* are cross-sectional views of yet another embodiment of the mask, FIG. 11*a* showing the mask in a neutral state and FIG. 11*b* showing the mask applied to a user's face.

FIGS. 11*a* and 11*b* illustrate a modification of the mask 200 which is identified generally by the reference numeral 300. Parts, components, and features of the mask 300 that are similar or the same as corresponding parts, components, or features of the mask 200 are identified with the same reference numerals, except that a value of 100 has been added to the reference numerals used to identify corresponding parts of the mask 200.

As shown in FIGS. 11*a* and 11*b*, the mask 300 can include outer and inner support walls 340, 342 which are made integral with the material forming the outer casing 312, which as in the previous embodiments, also forms the chamber 330.

As described above with reference to the outer casing 112 and 212, the outer casing 312 can be made from a flexible and/or elastic material. In the illustrated embodiment, the outer casing 312 includes a thickened area 350 which is generally in the shape of a channel portion including the outer and inner support walls 340, 342. Although the thickened portion 350 is made from a flexible material, such as silicone, rubber or other materials, the additional thickness relative to the other portions of the outer casing 112 provides the thickened region with a different and greater stiffness. In other words, the thickened region 350 can have a higher spring constant than the other portions of the outer casing 312. In other words, more force is required to deform the thickened region, than the remaining parts of the outer casing 312. As such, the deformation of the seal portion 304 can be similar to the deformation of the seal portion 204 described above with reference to FIGS. 10*a* and 10*b*.

Additionally, forming the outer and inner support walls 340, 342 integrally with the outer casing 312 can provide the additional benefit of a smoother, softer transition between the more flexible portion of the outer casing 312 and the thickened region 350, thereby further preventing user discomfort.

Optionally, the thickened region 350, including the outer and inner support walls 340, 342 can gradually taper into thinner supple regions of the outer casing 312.

As shown in FIG. 11*b*, when the seal portion 204 is deformed against the user's face, the support walls 340, 342 can at least partially splay apart as the seal portion 304 is compressed. Such a structure can provide for a more controlled deformation of the seal portion 304. The tapered thicknesses of the support walls 340, 342 can better control where and how deformation occurs, for example, allowing greater deformation of the seal portion 204 in regions proximal to the user's face as compared to the regions proximal to the frame 302.

In some embodiments of any of the masks 100, 200, 300, and the other masks described below, any of the masks can be constructed with only a portion of the seal 304 having a variable stiffness, such as through the use of granular jamming ability. For example, the granular jamming ability of the seal portion 304 can be limited to regions of the mask 300 that are proximate to those portions a user's face which are typically more challenging for achieving an airtight seal, for example, in the area around the bridge of the nose and the transitions to the adjacent cheek areas.

Figure 1:
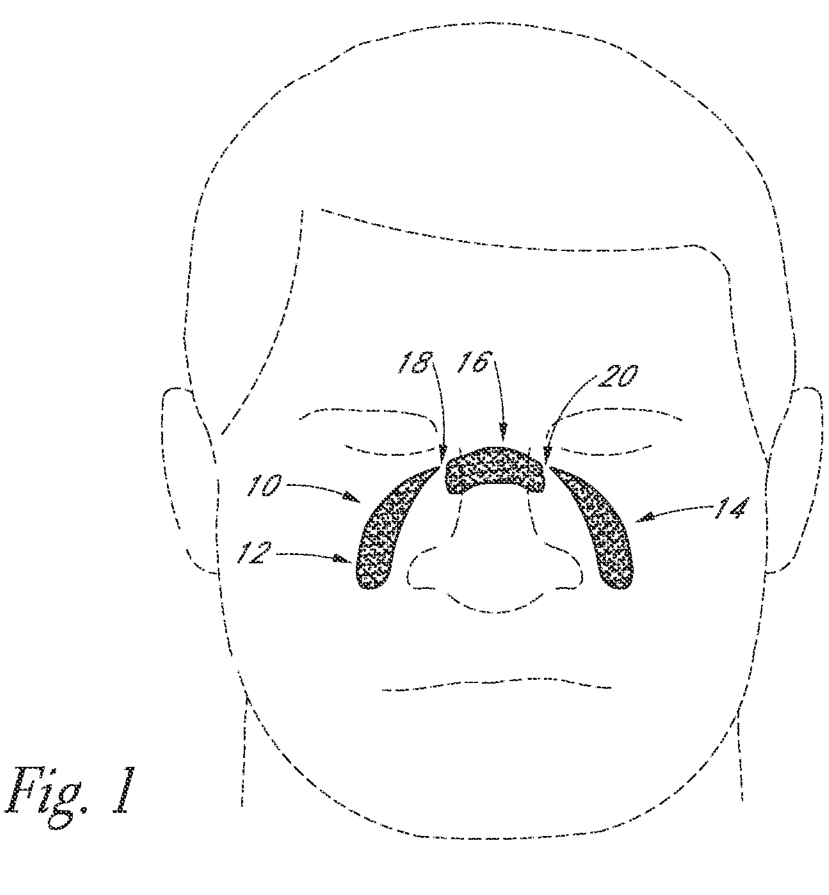
FIGS. 1 and 2 are schematic front elevational views of patient faces showing injuries caused by known masks.
Figure 2:
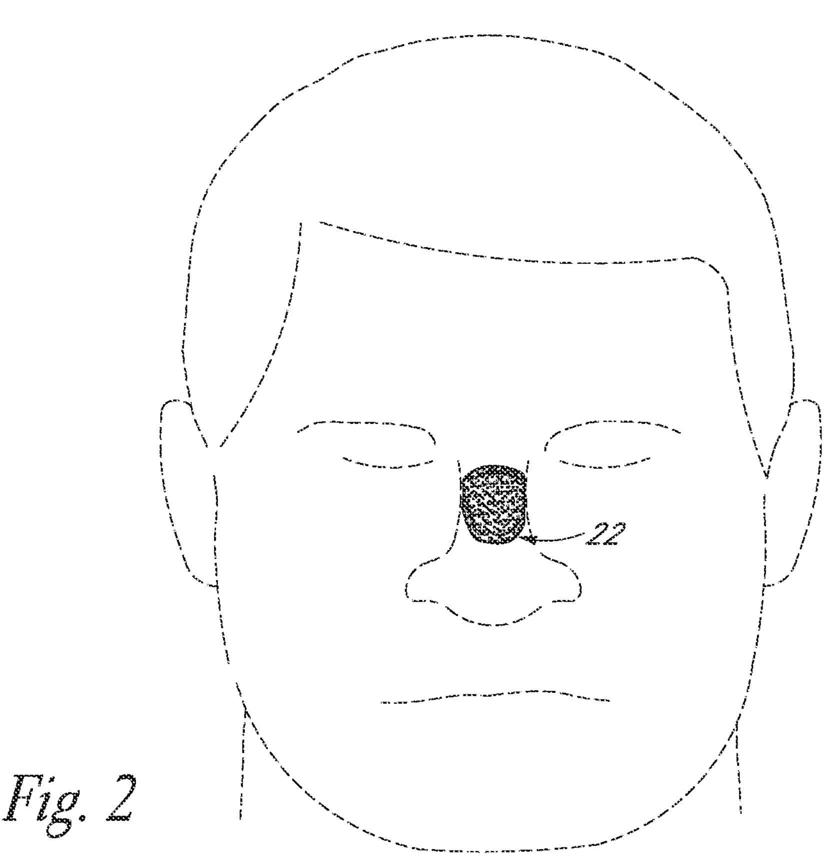
Figure 2A:
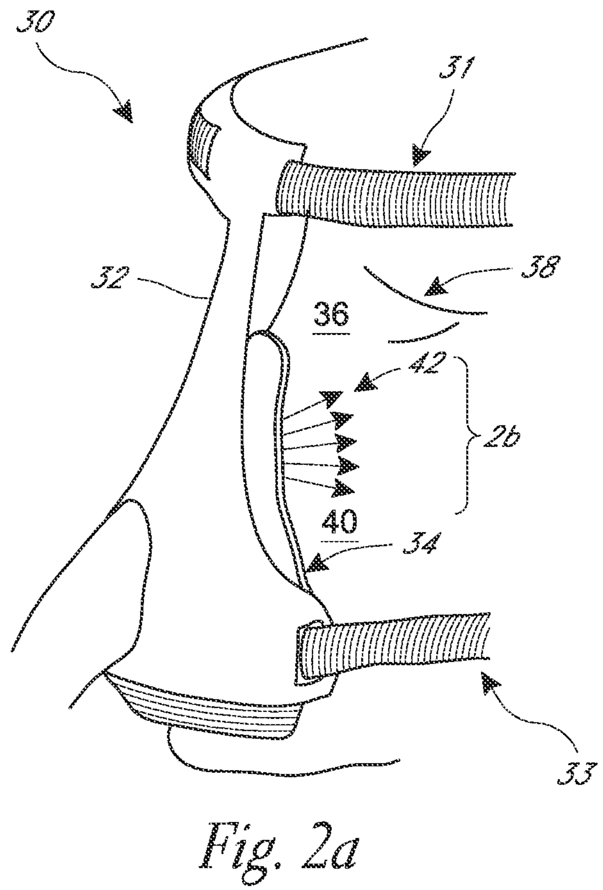
FIG. 2*a* is a perspective view of a mask secured to a patient's face and illustrating a leak of air flowing towards a patient's eye.

Additionally, variable stiffness functionality can also be used in areas that are susceptible to pressure related skin damage resulting from excessive application forces, for example, as discussed above with reference to FIGS. 1 and 2. The variable stiffness abilities, including the granular jamming principle of operation described above, can be more effective at deforming to match complicated geometries in an around the nose bridge, thus reducing leaks and dispersing application forces more evenly. Traditional seal designs can be used in other regions of the mask. Such a mask can help reduce the weight of the mask because the components necessary for providing the granular jamming functionality can weigh more than conventional mask components.

Figure 12:
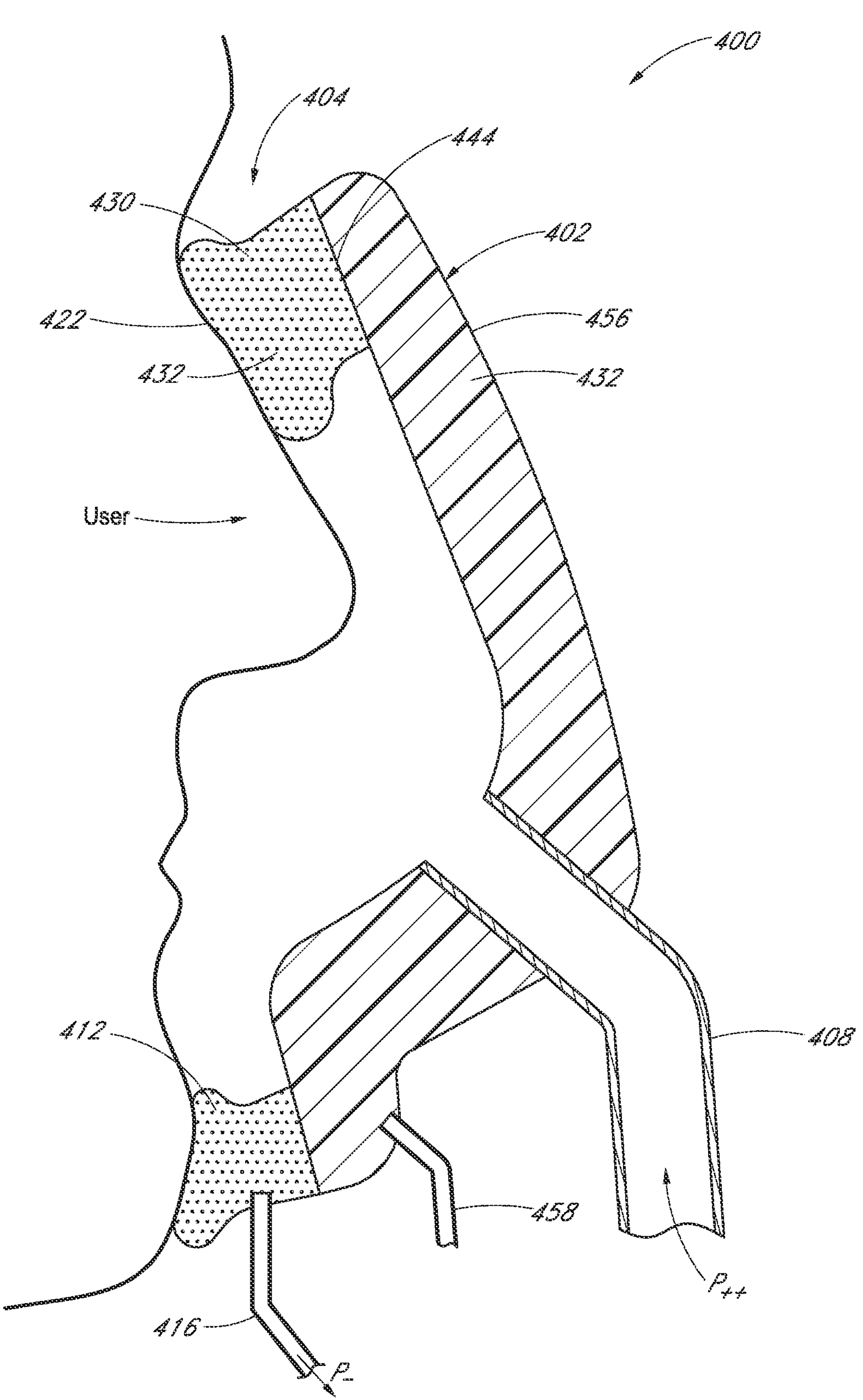
FIG. 12 is a side elevational and a partial sectional view of yet another embodiment of the mask.

FIG. 12 illustrates yet another modification of the mask 100, and is generally identified by the reference numeral 400. Parts, components, and features of the mask 400 which are similar or the same to any of the above-described masks are identified with the same reference numerals, except that a value of 100 has been added to the reference numerals used for describing the mask 300. In the illustrated embodiment, the mask 400 includes a frame 402, at least a portion of which (e.g., flexible regions) includes a structure configured for providing variable stiffness, for example, operating in accordance with the granular jamming principle of operation. The flexible regions allow for three dimensional deformation of the mask frame. In some embodiments the geometry of the flexible region may bias deformation to certain directions. In some embodiments, some portions of the frame 402 comprise flexible regions and other parts of the frame 402 substantially rigid portions. In other words, the frame can comprise one or more less rigid portions and one or more, more rigid portions. For example, as described above with reference to FIGS. 4*a*-4*c*, the frame 402 can comprise one or more flexible portions 109, 111 (FIG. 4*a*), which can serve as hinges and, optionally, can be in the form of granular jamming-enabled portions of the frame 402.

In some embodiments, such flexible portions can be in the form of pockets, for example, made with elastic material and filled with granular jamming materials 432. Additionally, the pocket can include a vacuum connection so that the pocket can be transitioned to a jammed state. In some embodiments, the flexible pockets can be formed with the frame by over-molding, however, other techniques can also be used. Additionally, in some embodiments, the flexible pockets can be made from different materials than the more rigid portions of the frame 402.

For example, one or more portions of or the entire the frame 402 can include one a substantially flexible and/or elastic frame casing 456, configured to contain a granular material 432. As such, the casing 456 forms a granular jamming chamber. Additionally, the mask 400 can include an additional vacuum connection 458 configured to allow the application of a vacuum to the interior of the chamber 456 for moving fluid from the chamber 456 and achieving a transition from neutral to jammed states, in the manner described above with reference to the seal portion. A conduit connection 408 can extend through the chamber 456 for providing a passage for breathable and optionally pressurized gasses.

Additionally, although not shown, the vacuum connection 458 can also include a one-way valve for maintaining a vacuum applied to the chamber 456, so as to maintain the chamber 456 in a conformed jammed state.

Similarly, the seal portion 404 can be made entirely of a granular jamming chamber, can include only a portion in the form of a granular jamming chamber, or can be made entirely out of a conventional sealing arrangement without any granular jamming.

With regard to the frame 402, the chamber 456, being made from a flexible and/or elastic material, can be configured to contain the granular material 432 which is also used within the seal portion 404. However, the chambers 430 and 456 can use different granular materials 432. The chamber 456 and the seal portion 404, in embodiments where both include at least a portion having a variable stiffness functionality, can be configured to adapt to a user's face in a similar manner as the seal portions described above of the previously described embodiments. For example, granular jamming can be utilized to shape the chamber 456 and/or the seal portion 404 to more closely match a user's facial geometry than traditional masks. For example, in some embodiments of methods of use thereof, the following steps can be employed:

1. Apply the frame 402, which includes the chamber 456, to a user's face while in a neutral state, and with the seal portion 404 detached.
2. Allow the granular material 432 in the chamber 456 to conform to the user's facial geometry, while in a neutral state.
3. Apply a vacuum to the chamber 456, for example, through the vacuum connection 458, to thereby increase the density of the granular material 432 in the chamber 456. The vacuum can cause the chamber 456 to shrink onto the user's face, for example, becoming an effective rigid casting of the user's face.
4. Remove the frame 402 from the user's face with it in a jammed state.
5. Attach the seal portion 404 to the frame 402, with the seal portion 404 in a neutral state and the frame 402 in a jammed state.
6. Apply the assembled mask 400 to the user's face, allowing the granular material 432 in the seal portion 404 to conform to the user's facial geometry.
7. Apply a vacuum to the seal portion 404 via the vacuum connection 416 thereby reducing the volume of the chamber 430, causing the chamber 430 to shrink onto the user's face, and becoming a substantially rigid casting of the user's face.

In the method set forth above, the customization of the mask 400 can be conducted in a two phase process, first customizing the shape of the frame 402, then customizing the shape of the seal portion 404. As such, the mask frame 402 itself can better follow the contours of the patient's face and thus require less deformation of the seal portion 404 thus better reducing dead-space and the associated rebreathing of air within the mask. The seal portion 404 acts as a spacer between the frame 402 and the user's face. Having a small amount of space between the frame 402 and the user's face may allow for the user to move their face or change position more easily than if the frame 402 were positioned closer or even in direct contact with the user's face, thus improving comfort and compliance.

Figure 13:
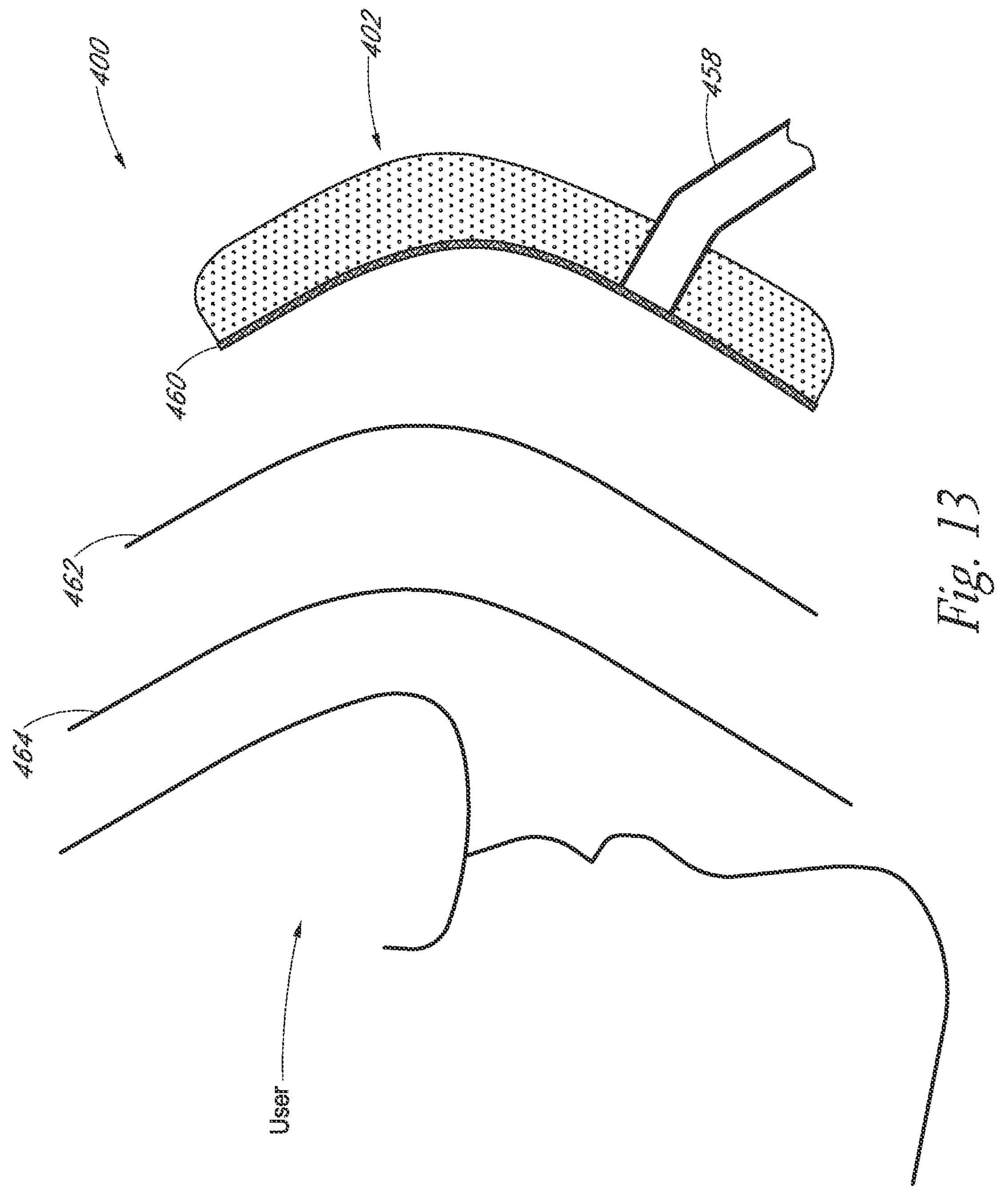
FIG. 13 is a side elevational and exploded view of the mask of FIG. 12 and three optional conforming guides.

With reference to FIG. 13, optionally, the mask 400 can benefit from the use of templates or forming guides to assist in the process of conforming the frame 402 to a user's face. For example, in some non-limiting embodiments, as shown in FIG. 13, small, medium and large conforming guides 460, 462, 464 can be in the form of substantially rigid shells designed to approximate three different sizes of facial geometries of a range of users. The sizes of the forming guides 460, 462, 464 can be predetermined to fit a range of facial geometry shapes and sizes. For example, the forming guides 460, 462, 464 may be available in small, medium, and large sizes and/or variants that cater for wide, narrow, or normal width faces. Other embodiments of the conforming guides 460, 462, 464 can cater to flatter or more pronounced facial profiles.

In a method of use, one of the conforming guides 460, 462, 464 can be chosen based on which is the best match for the geometry of a particular patient's face. The chosen conforming guide can thus be used to mold and shape the frame 402, for example, when the chamber 456 is in a neutral state. For example, the frame 402, with the chamber 456 in a neutral state, can be placed over and shaped to match the chosen of the three conforming guides 460, 462, 464. With the frame 402 applied to the chosen conforming guide as such, a vacuum can then be applied to the frame vacuum connection 468 to thereby shrink the chamber 456 and increase the stiffness of the frame 402, for example, by subjecting the chamber 456 to a sufficient vacuum so as to transition the chamber 456 into a jammed state. After such transition, the frame 402 can then be combined with the seal portion 404 and the above-described method of conforming the mask 400 to a user's face can continue as described above.

The advantage of using a conforming guide, such as one of the conforming guides 460, 462, 464 is that a conforming guide can be made from materials that are substantially more rigid than a patient's face. Thus, when a vacuum is applied to the chamber 456, and shrinks to some degree, the frame 402 can be pressed with a greater force against the conforming guide so as to retain the desired shape, a process that might be uncomfortable for a patient. Additionally, in some embodiments where only a portion of the seal and/or frame includes the granular jamming functionality, the shrinking and associated compressive force may be beneficial in increasing the sealing forces between the mask and the user's face. This may improve the ability of the mask to form a substantially airtight seal with the user's face.

In additional variations of the mask 400, a frame 402 can be used in combination with a traditional, non-variable stiffness seal portion. Such a traditional seal can comprise a silicone cushion as is commonly used presently in the mask arts, or any suitable alternative, wherein the seal is flexible but less conformable than the previously described granular jamming enabled seals.

Figure 14:
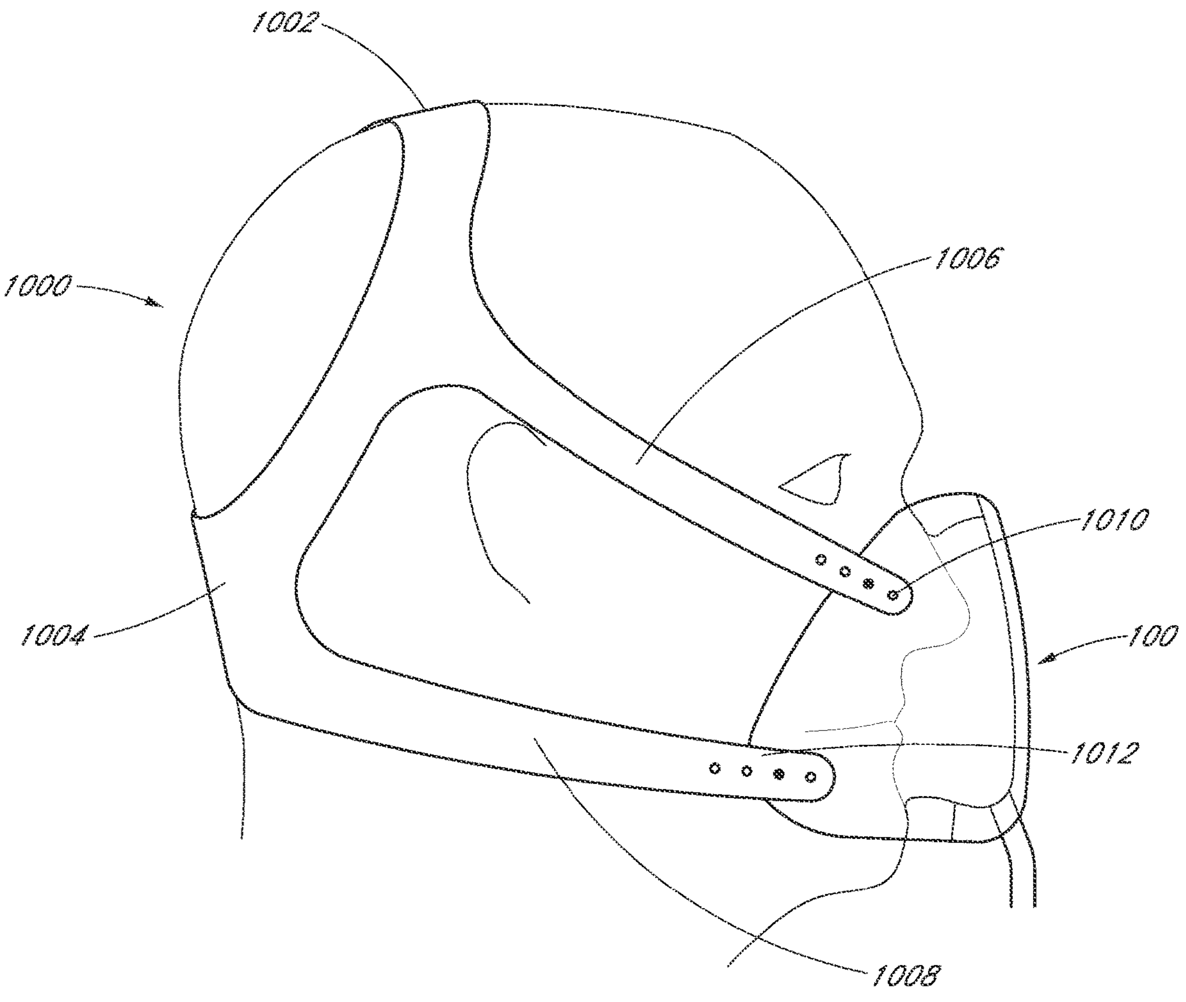
FIG. 14 is a schematic side elevational view of an embodiment of headgear that can be used in conjunction with any of the masks disclosed herein.

With reference to FIG. 14, variable stiffness, for example by way of the granular jamming principle of operation, can optionally be incorporated into a headgear arrangement for retaining a mask, such as any of the masks 100, 200, 300, 400 described above, or any of the masks described below.

For example, FIG. 14 illustrates a non-limiting exemplary embodiment of a headgear arrangement for the mask 100. The headgear 1000 can include a crown strap 1002, a rear portion 1004, an upper strap 1006, a lower strap 1008, an upper connection 1010 and a lower connection 1012. The upper and lower connections 1010, 1012 can be configured to connect the mask 100 to the headgear 1000.

Utilizing the process of granular jamming, the headgear 1000 can be configured to conform to a user's head shape and size, with reduced manual adjustments. For example, airtight chambers and granular material can be incorporated into portions of the headgear 1000 so as to provide a granular jamming functionality. For example, with reference to FIG. 15, one or more portions of the headgear 1000 can include a granular jamming layer 1020. The granular layer 1020 can include a granular layer casing 1022 containing granular material 1024. The granular casing 1022 can be made from a flexible and/or elastic material and can include a vacuum connection and optionally a one-way valve (not shown). As such, the headgear 1000 can be applied to a user's head, and then a vacuum can be applied to the chamber 1022 to thereby compress the granular material 1024 and transition the granular layer 1020 into a jammed state.

A process of using such a headgear 1000 can include applying the headgear 1000 to the head of a user with the granular layer chamber 1022 in a neutral state. The headgear can be conformed to the user's head manually, by pressing the headgear 1000 against the user's head. Then, with the headgear 1000 maintained to the conformed shape, a vacuum can be applied to the chamber 1022 to thereby transition the layer 1020 into a jammed state. As such, the granular layer 1020 can act as a sizing adjustment mechanism.

Optionally, the headgear 1000 can also include a shape sustaining layer 1026. The shape sustaining layer 1026 can be made from a semi-rigid material such that it can provide some structural support to the headgear 1000 when the granular layer 1020 is in a flexible neutral state. The shape sustaining layer 1026 may minimize the likelihood of the headgear tangling when it is not applied to a user's head, by keeping the headgear in a substantially open, three-dimensional shape. It can be advantageous for the headgear 1000 to maintain a substantially open three-dimensional shape as it can help fitting the headgear and mask more quickly and more easily.

In some embodiments, the shape sustaining layer may only be included in one or limited parts of the headgear 1000 which benefit from additional structural support. Additionally, including a discontinuous shape sustaining layer throughout the headgear 1000 may allow for the headgear to conform more readily to the size and shape of different user's heads.

Further, the headgear 1000 can also include a cushioning layer 1028 positioned on the inner side of the granular layer and/or the shape sustaining layer 1026 so as to provide additional comfort for the user. The cushioning layer 1028 can be configured to be in direct contact with the user's head or skin or hair or may be separated from the user's head by a decorative outer layer. The cushioning layer 1028 can be made from any soft material such as, but not limited to, foams, textiles, elastomers, and spacer fabrics. The cushioning layer 1028 can provide comfort to the user by softening any hard or sharp edges that may be formed by other layers within the headgear 1000. In some embodiments this layer 1028 may be elastic. Providing some elasticity in any of the layers of the headgear can provide an additional benefit of a temporary pre-loading feature during fixation of the mask 100 on a patients face. After fitting, the transition to a jammed state reduces or eliminates elastic tension in the headgear, and the jammed state can help lock the mask 100 on a patient's face. In the jammed state, the headgear 1000 holds the mask 100 on the patient and resists blow-off forces that could otherwise tend to push the mask away from the patient's face, for example, when pressurized air is applied. As such, the headgear 1000 can remain more stationary.

Additionally, as noted above, the headgear 1000 can include a decorative outer layer 1030 which can comprise a soft aesthetically pleasing sleeve, configured to cover any functional granularity of the shape of the granular layer 1020. In some embodiments, the decorative outer layer may encase the cushioning layer 1028 as well, or the cushioning layer may form the face contacting portion of the decorative outer layer. The decorative outer layer 1030 can be made from any suitable textile, polymer or other suitable material that is capable of providing a comfortable interface with the user's skin.

Figure 15:
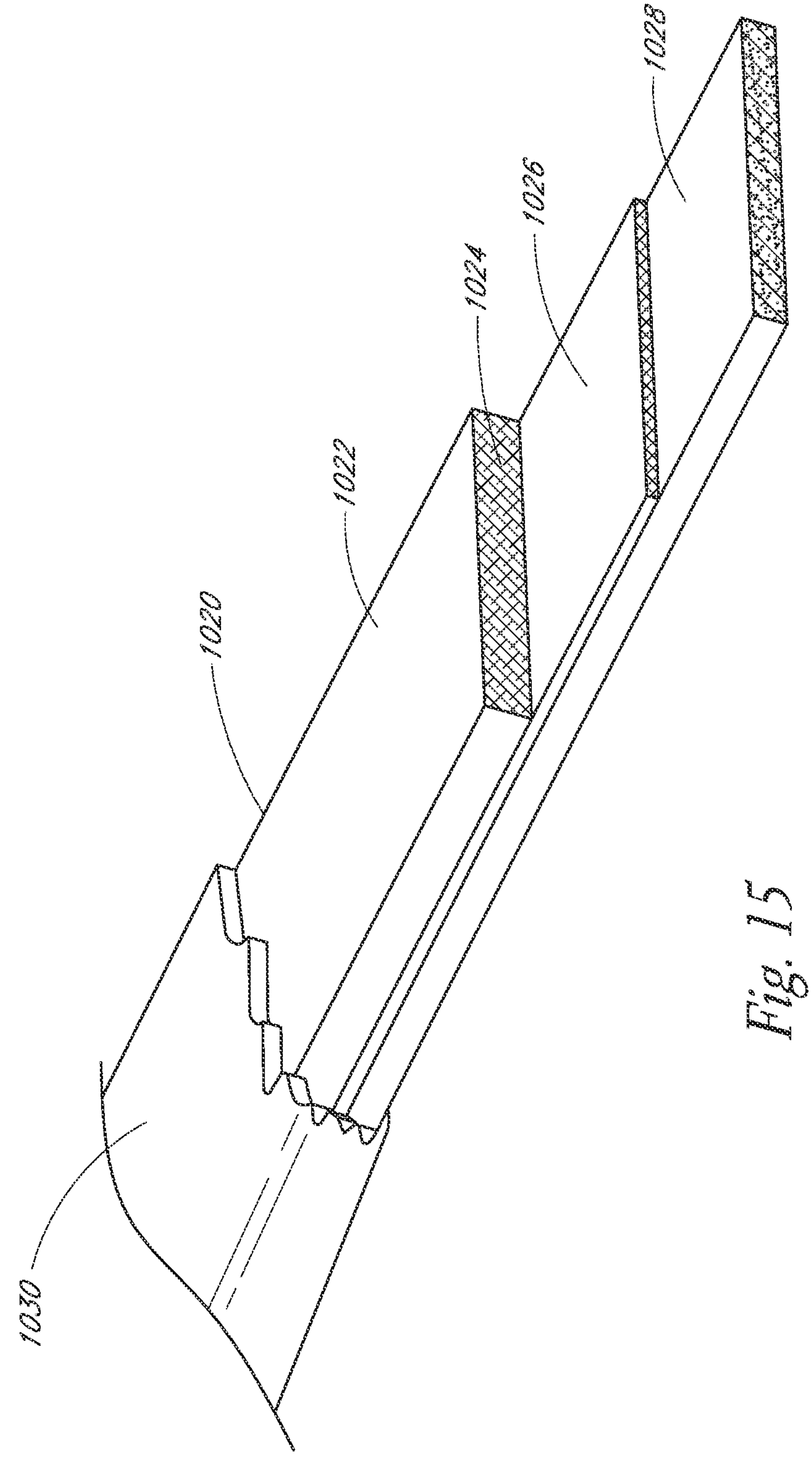
FIG. 15 is a partial cut-away view of a portion of the headgear illustrated in FIG. 14, and illustrating several optional layers that can be included in the headgear.

In some embodiments, the layered configuration of the headgear 1000 illustrated in FIG. 15 can be applied to a headgear of any form, known in the art, which differs from the form shown in FIG. 15. In some examples, the headgear 1000 can comprise a single strap that extends from one side of a user's face to the other, wherein the strap may be bifurcated at the rear of the user's head.

Figures 16A, 16B:
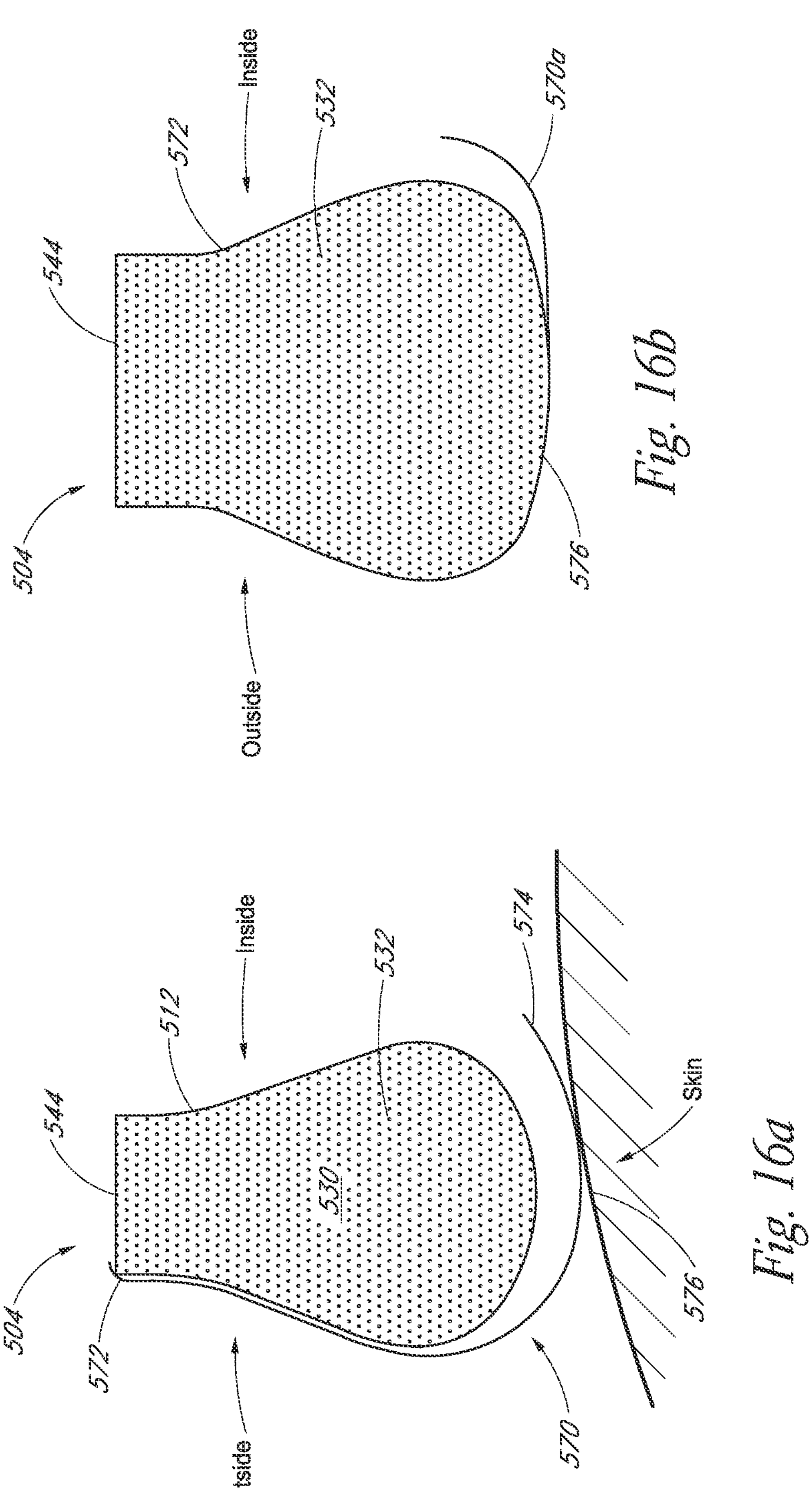
FIGS. 16*a* and 16*b* are schematic cross-sectional views of a further embodiment of the sealing portion of the mask including additional optional sealing membranes.

FIGS. 16*a* and 16*b* illustrate another modification of the seal portion 404 of the mask 100, and is identified generally by the reference numeral 504. Parts, components, and features of the seal portion 504 that are the same or similar to those of the seal portion 404 have been identified with the same reference numerals except that a value of 100 has been added thereto.

The seal portion 504 can be used in conjunction with any of the frame portions and masks described above and below. With continued reference to FIG. 16*a*, the seal portion 504 includes an additional sealing membrane that extends from an outer side of the seal portion 504, to an inner side of the seal portion 504. In the illustrated embodiment, the sealing membrane 570 includes a first connection end 572 connected to the outer side of the outer casing 512 of the seal portion 504 and extends around the lower end of the seal portion 504 to a free end 574. As such, in cross-section, the sealing membrane 570 forms a "C" shape. The free end 574, can be in the form of a flap that extends from the seal portion 504, and is an extra portion of the seal portion 504 that extends outwardly from the seal portion 504.

Optionally, as with some of the embodiments described above, the seal portion 504 can include a frame connection portion 544 configured for providing a removable connection to an associated frame (not shown). The sealing membrane 570 can comprise a thin flexible layer of material, such as, but not limited to, silicone rubber or a thermoplastic elastomer. Additionally, the sealing membrane 570 is configured to provide a sealing surface with the skin of a user's face.

The membrane connection 572 attaches the sealing membrane 570 to the seal portion 504 and/or frame of the associated mask (not shown). The sealing surface 576 of the sealing membrane 570 is configured to sit between the seal portion 504, and specifically, the outer casing 512 which can include a chamber 530 which includes a granular material 532. The sealing surface 576 is configured to sit between the seal portion 504 and the user's face to facilitate a substantially airtight seal between the seal portion 504 and the user's face. The sealing membrane 570 can be configured to extend from the membrane connection 572, around the outside of the seal portion 504 and between the user's face and the seal portion 504, terminating on the inside of the mask seal. In the embodiment of FIG. 16*a*, the sealing membrane 570 has a substantially "C" shaped cross-section, however, other cross-sections are also possible.

With reference to FIG. 16*b*, the seal portion 504 includes an integral sealing membrane 570*a*. The sealing membrane 570*a* can be configured as a thin flexible lip that extends from the sealing surface 576 of the sealing portion 504 towards the inside of the seal portion 504. The internal air pressure within the associated mask, during use, can cause the sealing membrane 570, 570*a* to be pushed against the user's face and thereby enhance a seal there between. Optionally, the free end 574 and the lip 570*a* can made from a more resilient material and/or can be biased into a shape extending away from the frame 502 and towards the patient so as to enhance sealing with the patient's face.

Figures 17A, 17B:
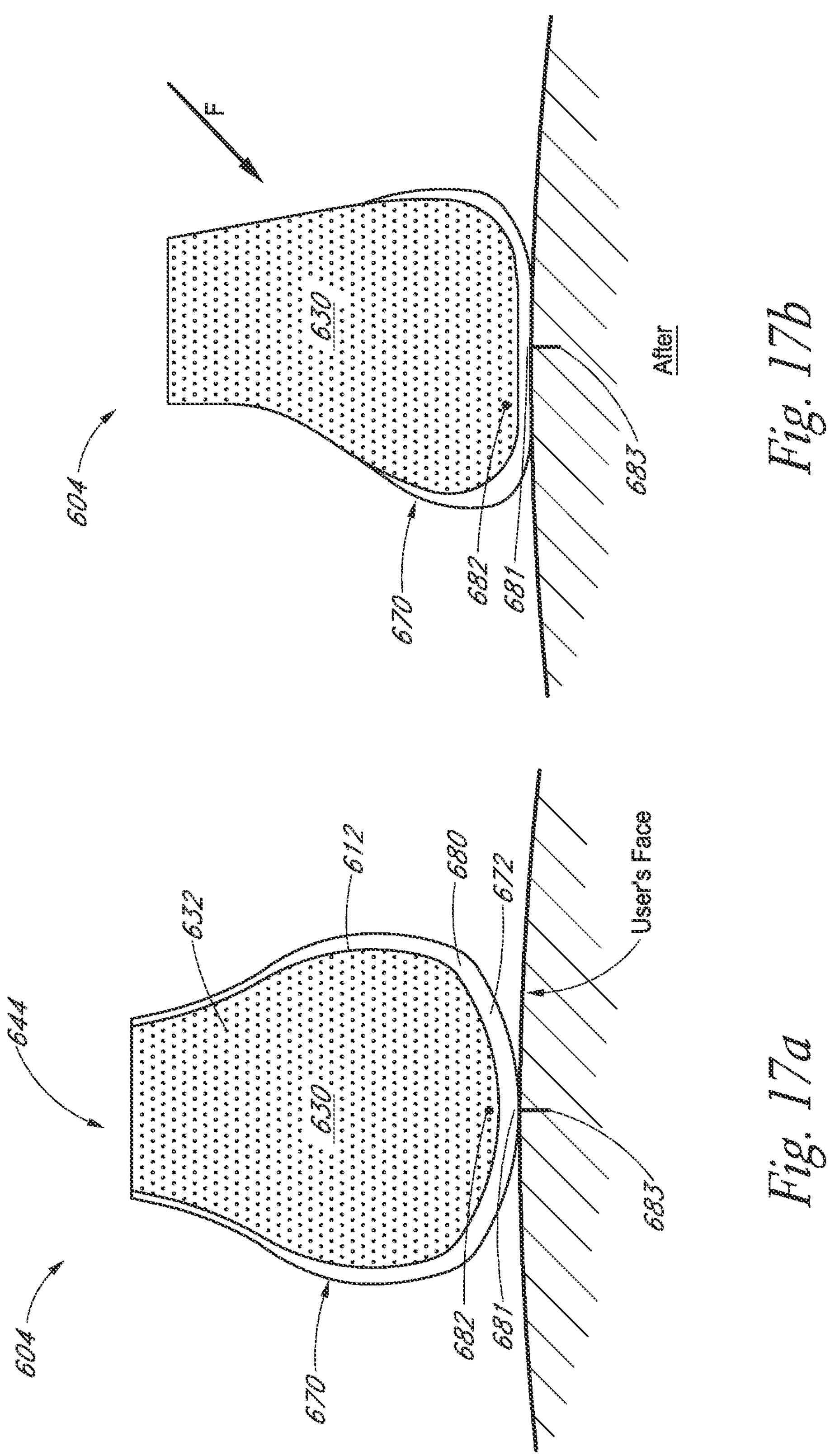
FIGS. 17*a* and 17*b* are cross-sectional views of a seal portion of a mask including an outer membrane before (FIG. 17*a*) and after (FIG. 17*b*) a force is applied.

FIGS. 17*a* and 17*b* illustrate yet another modification of the seal portion 504 and is identified generally by the reference numeral 604. Parts, components, and features of the seal portion 604 that are the same or similar to the seal portion 504 have been identified with the same reference numerals, except that a value of 100 has been added thereto.

In the illustrated embodiment, the seal portion 604, which can be applied to any of the masks and associated frames described above, includes a sealing membrane 670 which is offset from an outer casing 612 of the seal portion 604. For example, an offset between the inner surface of the sealing membrane 670 and the outer surface of the outer casing 612 can be filled with a fluid, such as a gas or a liquid, including lubricants, air, oil, gel, powder, or water to provide a reduced coefficient of friction between the inner surface of the sealing membrane 670 and the outer surface of the outer casing 612. In some embodiments, such fluid can also serve as a comfort layer. In FIG. 17*a*, the offset is identified generally by the reference numeral 680. Thus, with the chamber 630, in use, maintained in a "jammed" state, the sealing membrane can remain in a fixed stationary contact with the user's face while allowing the chamber 630 to make some movements and/or deformations.

For example, shear forces can be generated during use of the seal portions 604 and associated mask. Such shear forces can cause discomfort and skin damage to a user's face. For example, FIG. 17*a* illustrates the seal portion 604 in contact with a user's face, before any substantial forces are applied to it. The sealing membrane 670 and the chamber 630 define a membrane contact point 681 and a seal contact point 682. When the seal portion 604 is in a non-conformed state, the contact points can be aligned with a face contact point 683.

FIG. 17*b* illustrates the seal portion 604 with a force F applied to it. As shown in FIG. 17*b*, the application of the force F causes the seal portion 604 to deform. As a result, the seal portion can move substantially independently of the sealing membrane 670, which is shown via the movement of the seal contact point 682 relative to the membrane contact point 681 and the face contact point 683. This movement is possible due to a higher friction force between the user's face and the sealing membrane 670 than there is between the sealing membrane 670 and the outer surface of the chamber 630.

Figure 18:
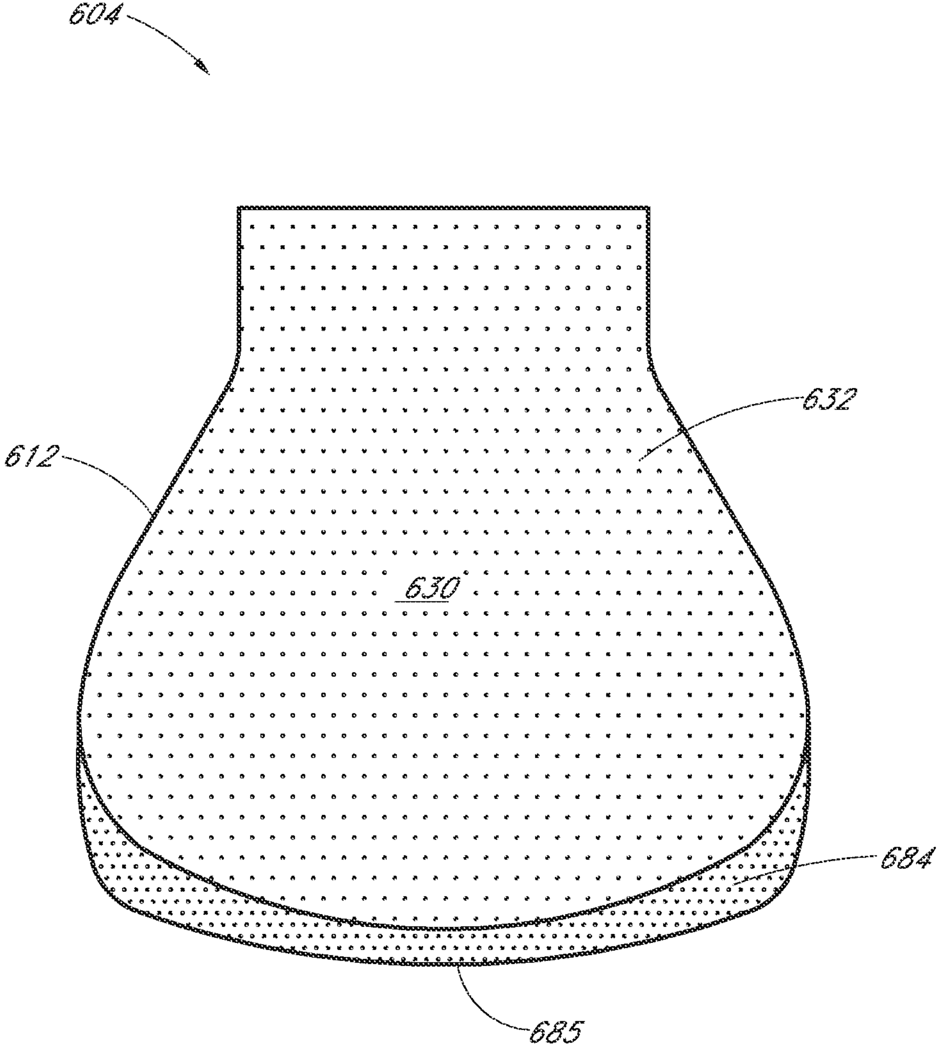
FIG. 18 is a cross-sectional view of another embodiment of the sealing portion of the mask with an optional additional sealing layer.

Optionally, in some embodiments, as shown in FIG. 18, the outer casing 612 of the chamber 630 can include an additional sealing layer 684 configured to form a sealing surface 685. The sealing layer 684 can be made from a soft and compressible material, such as but not limited to, a polymer foam or a textile. The sealing layer 684 can be configured to be softer and/or more compliant than the granular material within the chamber 630 when in a jammed state, thus allowing the sealing layer 684 to fill any gaps that may exist between the outer surface of the chamber 630 and the user's face.

Figure 19:
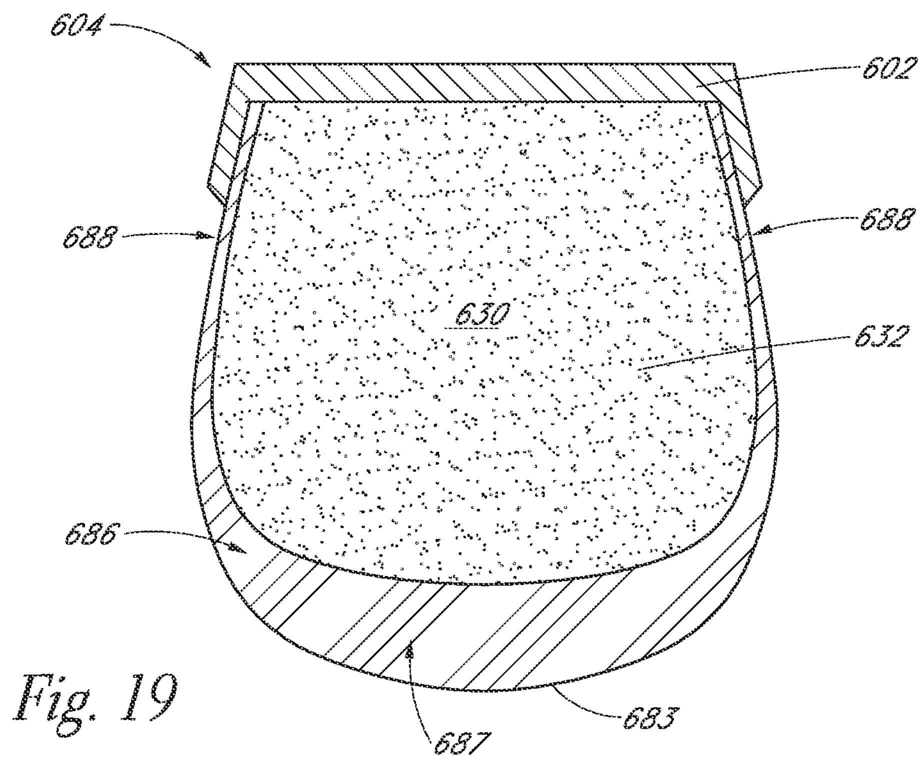
FIG. 19 is a cross-sectional view of another modification of the sealing portion of the mask, including an optional comfort layer.

With reference to FIG. 19, a further variation of the seal portion 604 which includes a variation of the seal membrane 670. In this variation of the seal portion 604, the seal membrane 686 includes a tapering thickness. In other words, the seal membrane 686 includes a thickened portion 687 in the vicinity of the skin contacting region 683 and thinner region 688 extending upwardly along the inner and outer side walls of the seal membrane 686. In the illustrated embodiment, the seal membrane 686 can be made from a very soft and flexible material, such as silicone. Preferably, the material used to form the seal membrane 686 can have a shore hardness in the lower half of the shore 00 scale. A material of this softness can allow the thick region of the seal membrane 687 to form a cushioning pad, capable of improving comfort of the sealing cushion 687 against the user's face (especially when the granular material 632 in the chamber 630 is in a fixed/rigid or "jammed" state). The softness of the material forming the seal membrane 686 can also allow the skin contacting region 683 to conform to a user's facial geometry, despite the thickened nature of the portion 687.

Figure 20:
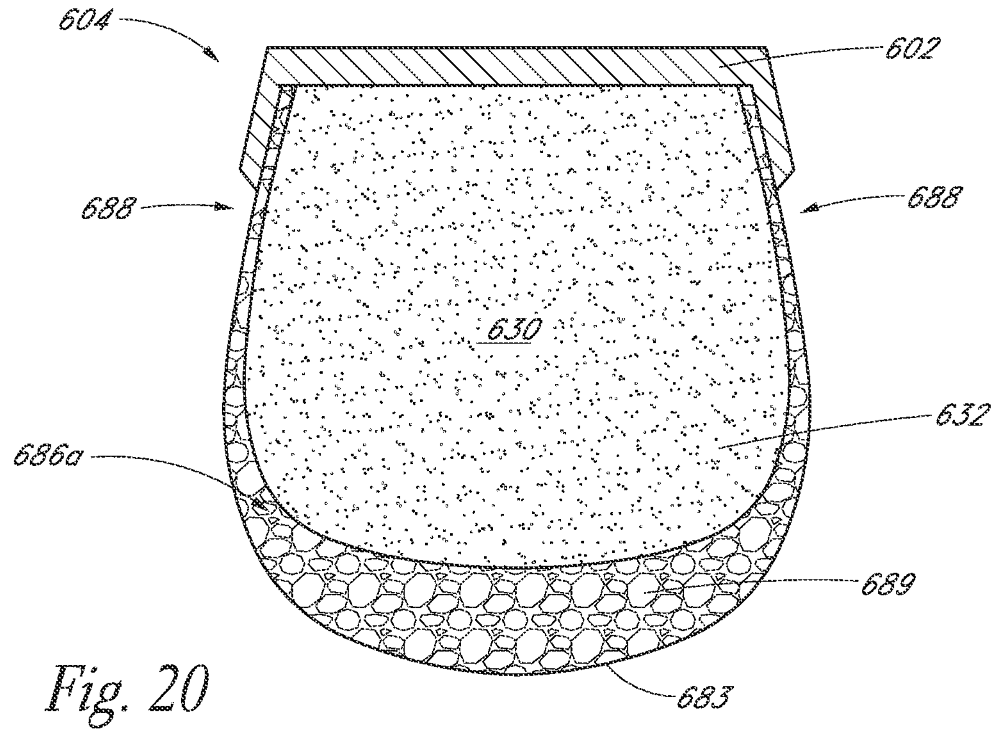
FIG. 20 is a cross-sectional view of another modification of the seal portion of the mask including an optional soft sealing membrane.

FIG. 20 illustrates yet another variation of the sealing portion 604. In this variation of the sealing portion 604, the seal membrane 686 is made with a foamed material 689. For example, the foamed material 689 can be made from silicone having air bubbles entrained therein, and predominantly in the skin contacting region 683. As such, the air bubbles forming the foam structure make the seal membrane 686*a* more compressible and provides a padding function, capable of softening the contact between the sealing member 686*a* and the user's face, particularly when the granular material 632 is in a jammed state. In some embodiments, the seal membrane 686*a* can be manufactured such that there are less air bubbles in the inner and outer wall portions 688. As such, these portions 688 of the seal membrane 686*a* can have a higher strength and provides more stability at the connection between the seal membrane 686*a* and an associated mask frame 602.

Figure 21:
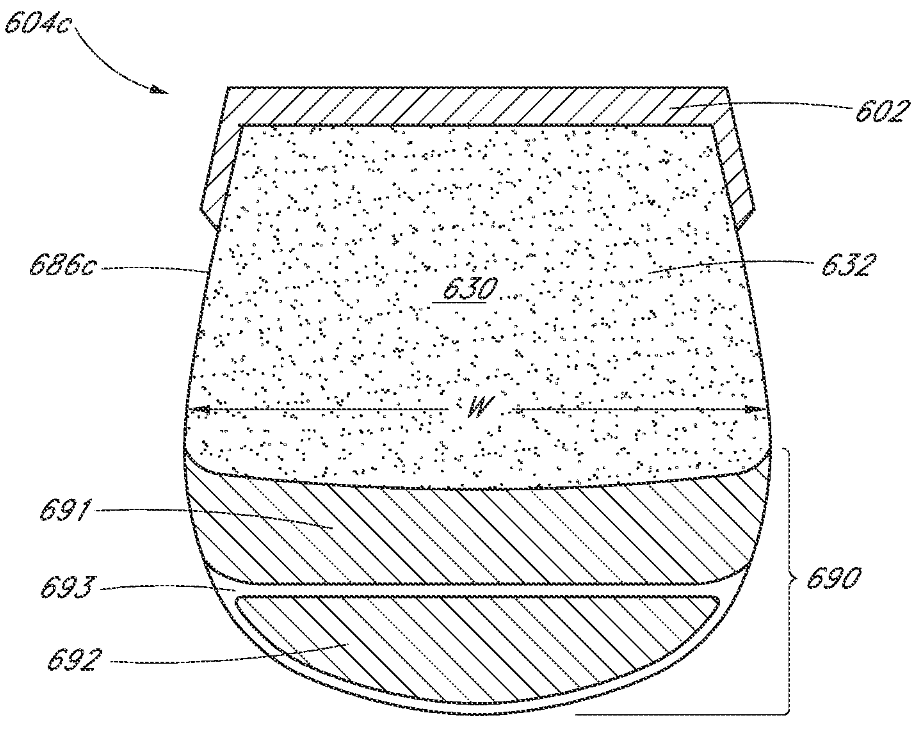
FIG. 21 is a cross-sectional view of yet another embodiment of the seal portion of the mask including an optional soft sealing membrane.

FIG. 21 illustrates yet another variation of the sealing portion 604 identified generally by the reference numeral 604*c*. In this variation of the sealing portion 604*c*, the seal membrane 686*c* includes a multi-layered padding assembly 690. The padding layer assembly 690 can include a first padding layer 691 and a second padding layer 692. Optionally, a slip region 693 can be disposed between the first layer 691 and the second layer 692. As such, the seal membrane 686*c* contains several layers of different materials. Proximal to the mask frame 602 can be a layer of granular material within the chamber 630, and which is capable of undergoing a jamming transition as described above, when a vacuum is applied to the chamber 630. The jamming transition allows the granular material 632 within the chamber 630 to alternate between a conforming and fixed states. When in the conforming or neutral state, the chamber 630 is able to change shape and conform to the facial geometry of the user. When in a fixed state, the chamber 630 retains any geometry that it was adapted to when in the conforming state, and transitions through the substantially rigid state also referred to as "a jammed state."

Users may find the feeling of a jammed chamber 630 to be uncomfortable when pressed against their face. Thus, the padding layer assembly 690 can be configured to provide a softer and more comfortable interface between the chamber 630 and the user's face. As noted above, the padding layer assembly 690 can include a first and second layer 691, 692. In some embodiments, the layers 691 and 692 are filled with gels.

Further, the first gel layer 691 can extend across substantially the entire width W of the sealing portion 604*c*. Additionally, the first layer 691 can be in a separate sealed chamber or compartment, separate from the chamber 630. Additionally, the second layer 692 can also be in a separate chamber separate from the layer 691. In some embodiments, the second layer 692 is not attached to the seal membrane 686*c*. Thus, in some embodiments, the slip region 693 is disposed between the layer 691 and the layer 692. The slip region can be configured to allow the second layer 692 to move somewhat independently of the first layer 691. This configuration can help reduce negative effects of shear forces on the user's skin; by allowing the layer 691, 692 to slide relative to each other. Movement of the second layer 692 can cause the region of the seal membrane 686*c* that is proximal to it, to deform and at least partially isolate the shear forces existing thereat. The slip region 693 can be filled with a lubricant so as to reduce friction and allow the second layer 692 to slide smoothly relative to the first layer 691 and the seal member 686.

FIGS. 22*a*, 22*b*, 22*c*, and 22*d* illustrate a further modification of the sealing portion 604 and is identified generally by the reference numerals 704*a*, 704*b*, 704*c*, and 704*d*. Parts, components, and features of the sealing portion 704*a*, 704*b*, 704*c*, and 704*d* that are the same or similar to the sealing portion 604 described above are identified with the same reference numerals, except that a value of 100 has been added thereto.

The various embodiments of the sealing portion 704*a*, 704*b*, 704*c*, and 704*d* each include structural reinforcements that affect the deformation of the respective sealing portions. Such structural reinforcements can further control how the respective sealing portions to form in use. Controlling the deformation of the sealing portion can be beneficial in providing an improved seal between a mask and a user's face. For example, some variations of the human face can extend along a spectrum of flatter contoured faces and more deeply contoured pointier faces. As such, when applying a mask to a flatter face, a better seal may be obtained with the periphery of the mask frame extending along a path that falls more closely along a plane. However, when applying a mask to a more deeply contoured, pointier face, a particular mask may provide a better seal if the periphery of the frame of the mask is partially folded in what can be referred to as a "clam shell" configuration. The clam shell movement and configuration is described in greater detail below with reference to FIGS. 23 and 24.

A conformable mask can be provided with more controlled deformation, for example, to induce a reactionary clam-shelling movement, or resist or better accommodate other desirable movements by including structures, for example, within the associated frame and/or seal portion. The embodiments of FIGS. 22*a*, 22*b*, 22*c*, and 23 include internal structures that provide for such functionality.

In some embodiments, the internal structures, which can be in the form of strands, are held in a taught position such that deformation in one location translates to movement/deformation in another region. For example, deformation caused by pressing the associated mask against the bridge of the nose and thereby compressing the seal will result in the reinforcement strand pulling the sides of the seal inwards towards the nose. This can also be referred to as a clam-shelling movement.

In some embodiments, the strands can have a 3D structure such as a chain link, a spiral, or other configurations. The surface area provided by such structures allows the granular material 732 to apply forces to the strands that are perpendicular to the length of the strand (i.e., the longitudinal direction of the seal portion 704). This helps to suspend the strand in a central position within the seal portion 704, especially when the granular material 732 is in an unjammed state. The 3D structure also allows the strand to be fixed in place more securely when the granular material 732 is in a jammed state. The length of the strand can be pulled through the granular material when the seal portion 704 is deformed, but the strand should resist coming into contact with the seal membrane 712 or the mask frame 702. These structures, features and functionalities are described in greater detail below with reference to FIGS. 22*a*-22*d*.

Some of these embodiments, generally speaking, include flexible but less elastic structures that extend along the longitudinal length of the associated sealing portions. These structural components generate reaction forces that facilitate and guide the deformation of the associated sealing portions, to greater or lesser degrees. Additionally, these structural reinforcements optionally allow the chamber 730 containing granular material 732 which provides a granular jamming functionality, to be made from a more elastic material that provides for a better more controllable granular jamming transition, a greater degree of conformability, but with additional structural reinforcements to provide some controlled or induced reactionary deformations.

Figure 22B:
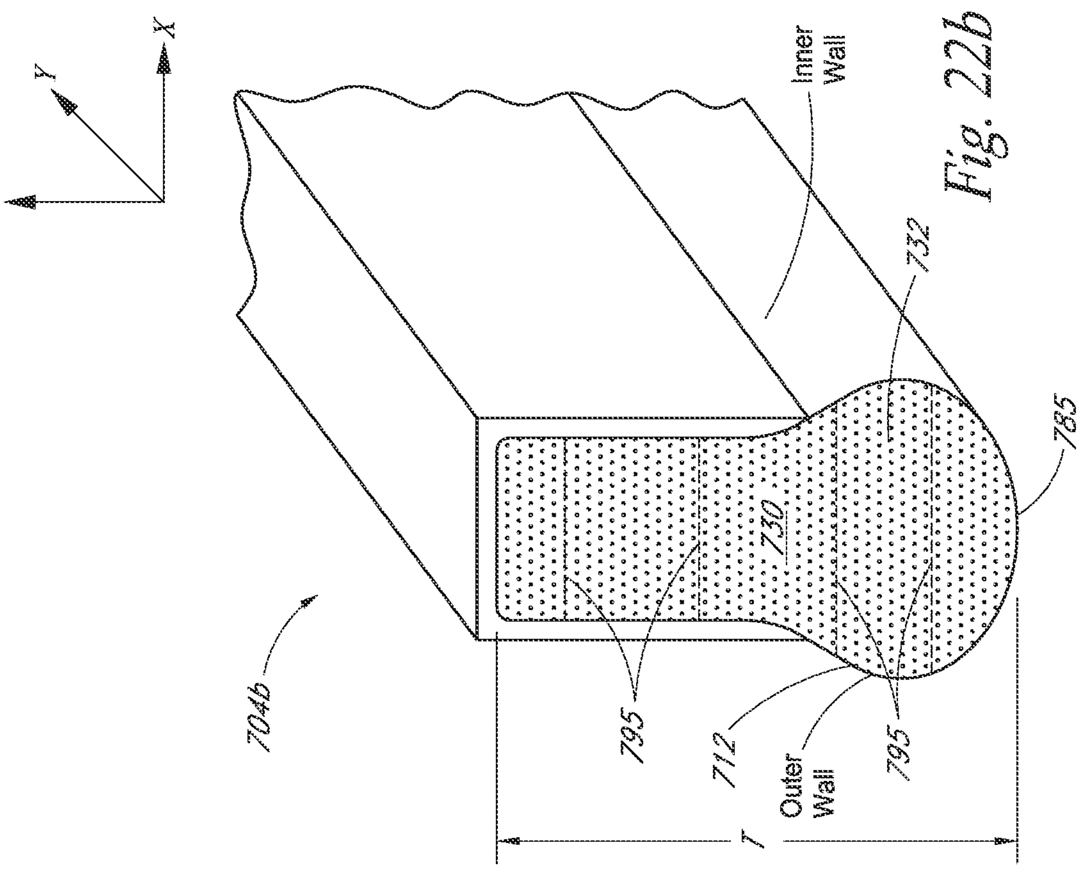
FIG. 22*b* is a partial cross-sectional and perspective view of yet another modification of the seal portion of the mask, including internal tie members.
Figure 22A:
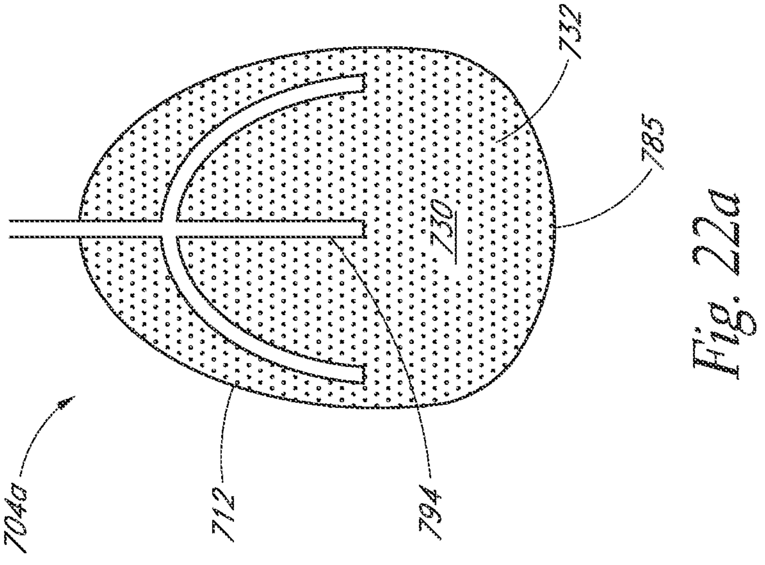
FIG. 22*a* is a cross-sectional view of yet another modification of the seal portion of the mask including an internal skeleton member.

With reference to FIG. 22*a*, the sealing portion 704*a* includes an internal skeleton 794. In the illustrated embodiment, the internal skeleton 794 is generally a pitchfork shape cross-section member that extends longitudinally within the seal portion 704*a*. Optionally, the internal skeleton 794 can extend around the entire periphery of an associated mask frame (not shown) so as to form an annular loop around the entire periphery within the seal portion 704*a*.

The outer casing 712, which in this embodiment, forms the chamber 730 containing the granular material 732, can be connected to the internal skeleton 794 in various locations. Additionally, the internal skeleton 794 is generally open and surrounded by the granular material 732. However, the internal skeleton 794 can constrict movement of the granular material 732 to some extent within the chamber 730.

The internal skeleton 794 can be constructed by material that is at least semi-rigid, such that the internal skeleton 794 has some flexibility but substantially maintains its shape when the mask is in use. Thus, the internal skeleton can guide the seal portion 704*a* in a clam-shelling movement, described in greater detail below.

With reference to FIG. 22*b*, the seal portion 704*b* can include a plurality of internal ties 795 at one or a plurality of different locations along the thickness T of the seal portion 704*b*. In the illustrated embodiment, the seal portion 704*b* includes internal ties 795 at four different levels along the thickness of the seal 704*b*. Additionally, at each level, there are a plurality of internal ties extending from the inner wall to the outer wall of the seal portion 704*b*. The internal ties 794 can be configured to be flexible but relatively inelastic, such that lateral expansion of the seal portion 704*b* is restricted. However, because the internal ties 795 are noncontinuous, the granular material 732 can still move relatively freely within the chamber 730.

Figures 22C, 22D:
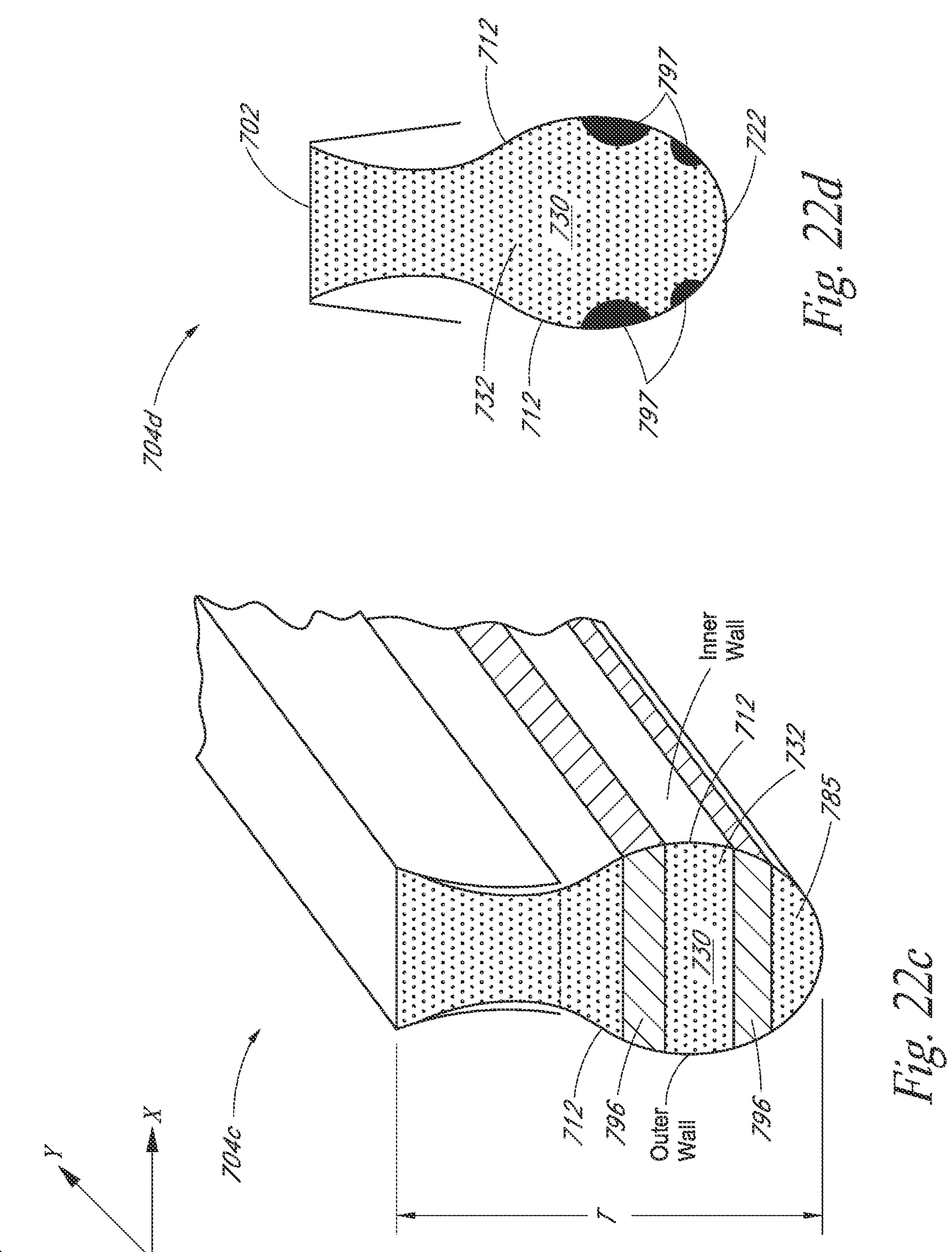
FIG. 22*c* is a cross-sectional and partial perspective view of another modification of the sealing portion of the mask, including an optional plurality of structural layers within the seal portion.
FIG. 22*d* is a cross-sectional view of yet another modification of the seal portion of the mask, including structural beads in the sidewalls of the seal portion.

With reference to FIG. 22*c*, the sealing portion 704*c* can include one or more structural layers 796. The structural layers 796 can extend between the inner and outer walls of the seal portion 704*c*. Additionally, the structural layers 796 can be disposed at different heights along the thickness T of the sealing portion 704*c* and can be spaced from one another with the chamber 730 disposed there between. The structural layers 796 can comprise layers of a material that is generally more rigid than the material forming the chamber 730. As such, the granular material can flow and thus deform along in the chamber 730 to provide an enhanced seal with the user's face. The rigidity provided by the structural layers 796 functions in several ways. For example, the material of the structural layers can be the same as that forming the chamber 730, but thicker than the outer walls thereof. As such, the increased thickness makes the structural layers 796 stiffer. Alternatively, the structural layers 796 can be made from a different material that is more rigid than that forming the outer surfaces of the chamber 730.

With reference to FIG. 22*d*, seal portion 704*d* can include ridges or beads 797 extending along the inner and outer walls of the chamber 730. The structural beads 797 can be configured as thickened wall sections of the outer casing 712 forming the chamber 730. As in the many other embodiments, the outer casing 712 can be made from a flexible material with elastic properties. However, the bead portion 797, being thicker than the other portions of the outer casing 712, can provide a higher stiffness than the other portions of the outer casing 712. As such, the structural beads 797 are less elastic and thus can limit expansion or deformation of the inner and outer walls of the seal portion 704*d*. Optionally, the beads 797 can form a continuous structure or loop around the length of the seal portion 704*b*. Optionally, the beads 797 can be made of thin metal wires or rigid plastics such as polycarbonate or other materials. In some embodiments, the beads 797 can have a diameter of about 0.1-5 mm.

Figures 23, 24:
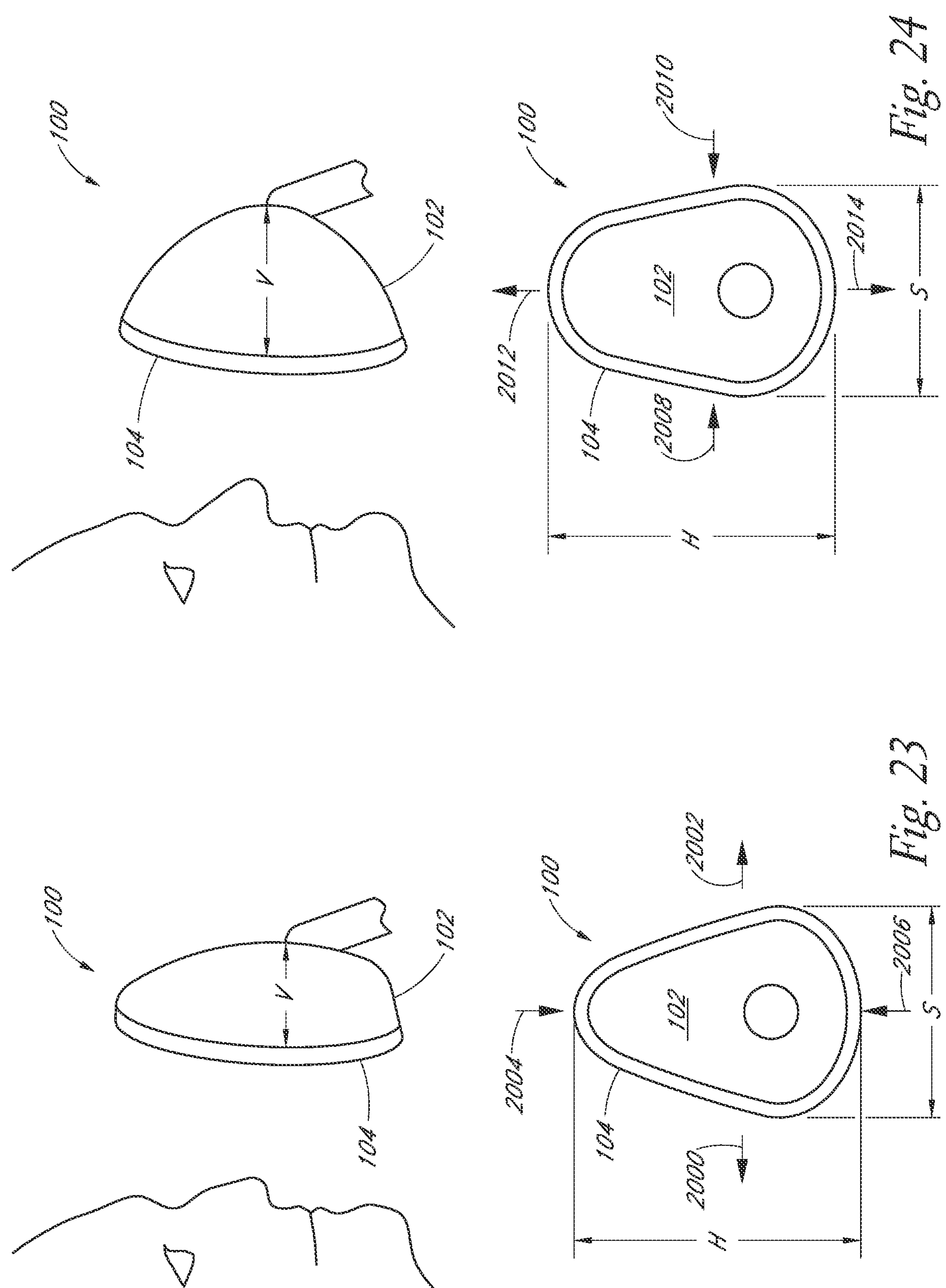
FIGS. 23 and 24 are side elevational and rear elevations views of the mask illustrating a clam-shelling movement.

With reference to FIGS. 23 and 24, the clam-shelling movements referenced above are illustrated therein. With reference to FIG. 23, a mask 100 can be applied to a user face that is generally flatter. Thus, the mask 100 can be deformed by pulling the side walls laterally outwardly, for example, in the direction of arrows 2000 and 2002. As such, the frame 102 becomes wider in the direction of dimension S, and shorter in height along the dimension H. The structural reinforcements described above with regard to the seal portions 704*a*-704*d*, can cause reactionary forces that tend to cause the deformation of the seal 104, in a clam shelling movement, to better follow the deformation of the frame 102, so as to reduce the total height H of the seal 102. For example, the reactionary forces, generated by the structural reinforcements described above, cause reactionary forces in the direction of arrows 2004, 2006 on the seal. Additionally, the structural reinforcements can help prevent the seal portion 704*b* from being "necked" (squeezed into an excessively thin shape) by helping to maintain the desired shape of the seal 104 and optionally the location of the granular material. If excessive necking occurs, the stiffening function of the granular jamming-enabled portions of the seals can be reduced.

By contrast, with reference to FIG. 24, when the mask 100 is applied to a user's face with deeper contours and a more pointy configuration, a user may attempt to squeeze the side walls of the mask 100 inwardly, in the direction of arrows 2008, 2010. This squeezing motion causes reactionary forces, which can be at least partially due to the structural reinforcements described above with reference to seal portions 704*a*-704*d*, in the direction of arrows 2012, 2014 which tend to increase the overall height H of the frame 102 and seal portion 104.

Optionally, as described above with reference to FIGS. 4*a*-4*c*, the mask 100 can include one or more flexible portions 109, 111 which can be configured and/or oriented to enhance the ease of the above-described clam-shelling movement.

An aspect of at least one of the embodiments disclosed herein includes the realization that this clam-shelling movement can assist a user in attempting to fit a mask 100 onto different user faces.

Figures 24A, 24B, 24C:
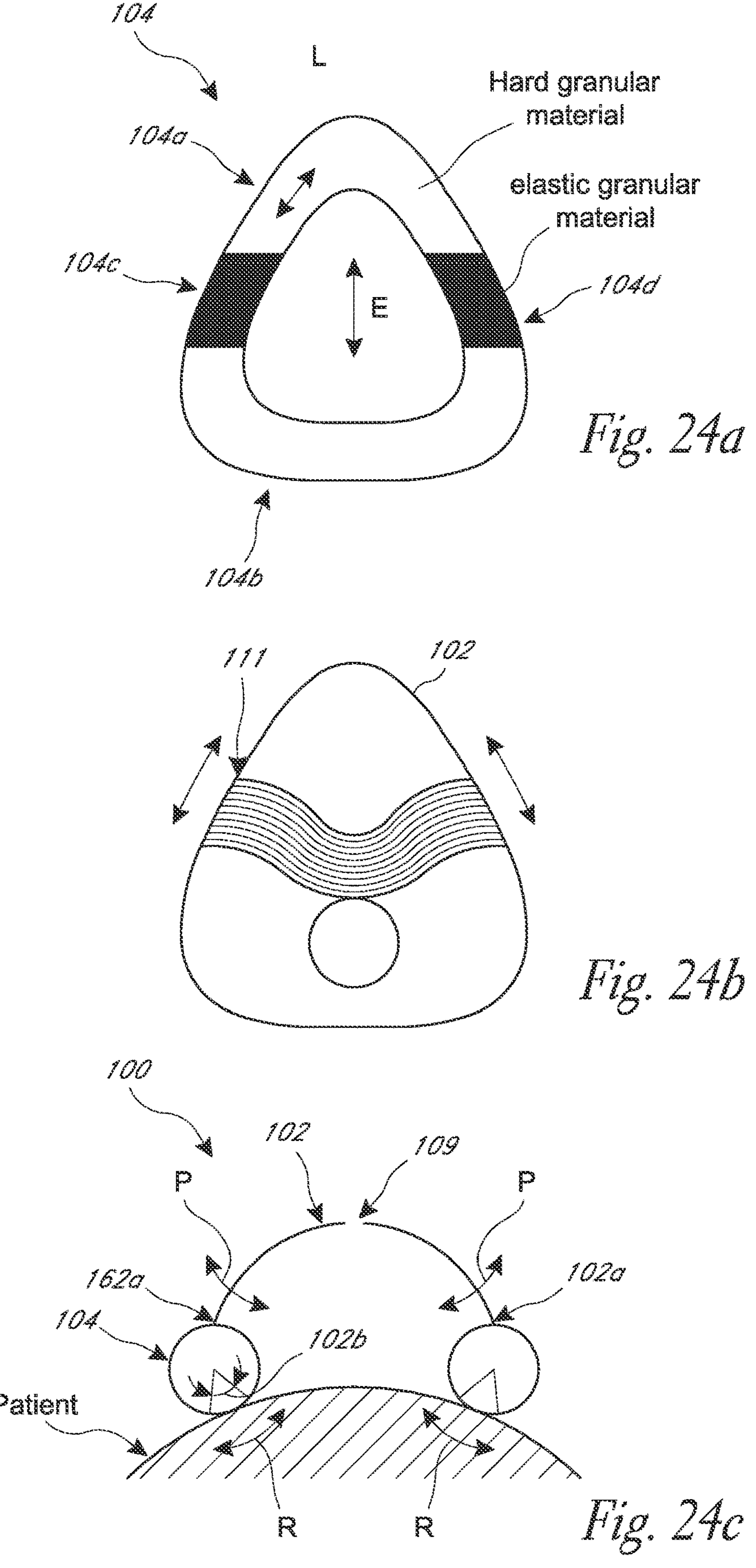
FIG. 24*a* is a schematic rear elevational view of another modification of the mask.
FIG. 24*b* is a schematic front elevational view of the mask of FIG. 24*a*.
FIG. 24*c* is a schematic sectional view of the mask of FIG. 24*a* illustrating a reactionary movement of a seal of the mask of FIG. 24*a*.

With reference to FIGS. 24*a* and 24*b*, the mask 100 can also be provided with optional features configured for better accommodating movements of a patient, including after the mask 100 has been fitted onto their face, and optionally, after a variable stiffness portion of the mask has been transitioned to a stiffer state. For example, with reference to FIG. 24*a*, the seal portion 104 can include a variable stiffness portion that has different characteristics along its peripheral length L.

For example, with reference to FIG. 24*a*, the seal 104 can be considered as including an upper portion 104*a*, a lower portion 104*b*, and intermediary portions 104*c*, 104*d* disposed on the left and right sides of the seal 104 and between the upper and lower portions 104*a*, 104*b*. Optionally, the intermediary portions 104*c*, 104*d* can be configured to have different mechanical characteristics relative to the upper and lower portions 104*a*, 104*b*. For example, such differential mechanical characteristics can be provided by different thicknesses of materials, different material types, and/or different material configurations. In some embodiments, the upper and lower portions 104*a*, 104*b* can include granular jamming chambers including granules made from a harder material. By contrast, the intermediary portions 104*c*, 104*d* can include granular jamming portions including softer granular material, for example, material that is more elastic and less stiff than the granular material in the upper and lower portions 104*a*, 104*b*.

Optionally, the chambers forming the upper portion 104*a*, lower portion 104*b*, and intermediary portions 104*c*, 104*d* can be formed from a single chamber configured for variable stiffness such as operation under the granular jamming principle of operation described above, or other configurations. Optionally, in a single chamber configuration, dividers can be included between the various different portions 104*a*, 104*b*, 104*c*, 104*d* so as to maintain the stiffer and softer granules in the desired locations. Further, optionally, the portions 104*a*, 104*b*, 104*c*, 104*d* can be made from separate chambers positioned proximate or juxtaposed to one another, in the arrangement illustrated in FIG. 24*a*, however, other configurations can also be used.

In any of the above or other configurations, the seal portion 104 can be configured to provide for enhanced flexibility in the areas of the intermediate portions 104*c*, 104*d*, for example, as noted above, with the use of softer, or more elastic granular material in the intermediary portions 104*c*, 104*d*. Optionally, these intermediary portions 104*c*, 104*d* can be configured to be more deformable even when in a state of increases stiffness or a "jammed state." Such additional deformability can allow these regions to be elongated in the direction of the arrow E of FIG. 24*a* so as to better accommodate movement of the jaw of a user. Further, optionally, the intermediary portions 104*c*, 104*d* and/or the upper and lower portions 104*a*, 104*d* can include elastic casings forming the chambers containing the granules.

As such, and optionally in addition to using softer or more elastic granular material in the intermediary portions 104*c*, 104*d*, the seal 104 can allow for stretching in the direction of arrow E and elastic return to the same or substantially the same shape before such stretching in the elongation direction E. During stretching along the direction E, some necking can occur in the granular material in the portions 104*a*, 104*b*, 104*c*, 104*d* as such regions are elongated. Such necking can substantially or completely disappear when the force applied to the seal 104 causing elongation in the direction of arrow E is released. Such elastic return can be accommodated by the softer or more elastic granules included the intermediary portions, 104*c*, 104*d* while maintaining the same arrangement in relation to each other, for example, while in a jammed state. In comparison, if necking occurs in a region, for example, the upper and lower portions 104*a*, 104*b* in which hard granular materials are used, such necking may not return to the original state because such necking can be associated with actual flow or movement of the granules, relative to each other, rather than elastic deformation of the granules.

With reference to FIG. 24*b*, additional beneficial jaw movement accommodation can also be achieved by providing additional flexible portions to the mask 100, such as in the frame portion 102. Optionally, the frame 102 can include a flexible portion, such as the flexible portion 111, described in greater detail above with reference to FIG. 4*a*. Optionally, with continued reference to FIG. 24*b*, the flexible portion 111 can be in the form of bellows, which allow the frame 102 to expand along with the expansion of the seal portion 104, as described above in the elongation direction E. Such bellows can be made from an additional member made from a flexible material, such as silicone, attaching two parts of the frame 102 together. In the form of a hinge or expandable bellows, the flexible portion 111 can allow the frame portion 102 to better accommodate patient movements, such as jaw movements, even after portions of the seal or other portions of the mask have been transitioned to a higher stiffness state, such as under the granular jamming principle of operation, or other techniques.

With reference to FIG. 24*c*, the mask 100 can also include optional features to further accommodate movements of a user's face during use of the mask and/or during fitting of the mask 100. For example, with reference to the cross-sectional view of FIG. 24, when portions of the frame are moving inward or outwardly, for example, in the direction of arrows 2000, 2002, 2008, 2010 of FIGS. 23 and 24, and optionally about flexible portion 109, the seal 104 can move relative to a patient's face. Thus, in some optional embodiments, portions or all of the connection between the frame 102 and the seal 104 can include additional flexibility to allow, enhance, or increase an additional flexibility or movement of the seal 104 relative to the frame 102.

For example, as shown in FIG. 24*c*, movement of portions of the frames along the arrows P, which may be considered as a pivoting direction of movement relative to the flexible portion 109, the seal portion 104 can roll along a surface of the patient, through arcs identified by the arrows R in FIG. 24*c*. Thus, the mask 100 can optionally include one or more flexible connectors 102*a* connecting the frame to the seal 104. The flexible connector 102*a* can be in the form of a flexible portion of the frame 102, a separate flexible device interposed between the frame 102 and the seal 104 and/or by the configuration of the portion of the seal 104 connected to the frame 102, for example, where only a thin or narrow area of the seal 104 is attached directly to the frame 102. Other configurations can also be used. In some embodiments, the flexible connections 102*a* are configured to allow the seal 104 to roll relative to the frame 102 with relatively little force, for example, through a range of rolling angles represented by the angle 102*b* of FIG. 24*c* with very little force, for example, one or a few newtons. However, other stiffnesses could be used which would generate other ranges of movement under different ranges of forces applied.

Figure 25:
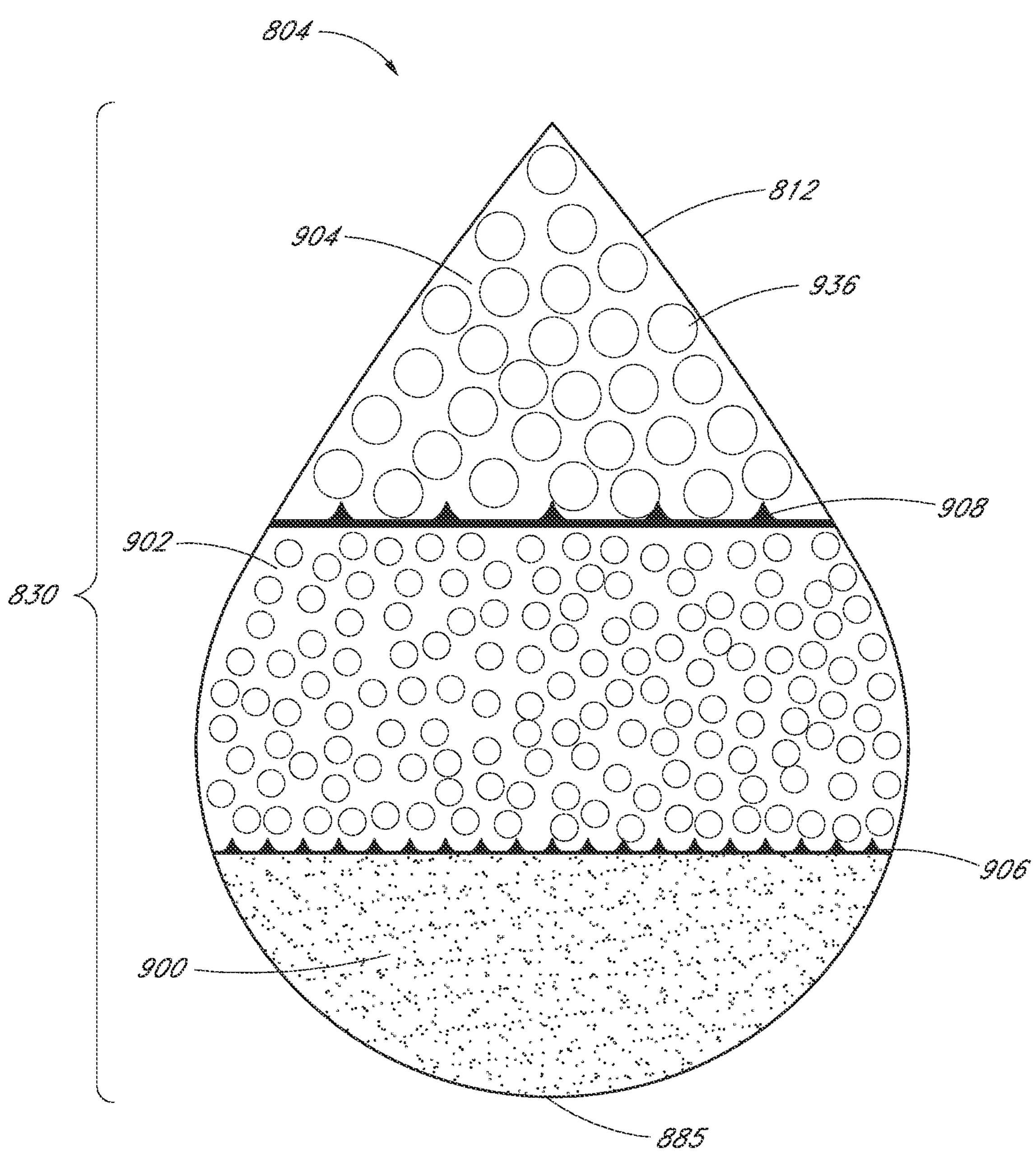
FIG. 25 is a schematic illustration of yet another modification of the mask including layers of different granular materials.

With reference to FIG. 25, another modification of the seal portion 704 is illustrated therein and identified generally by the reference numeral 804. Parts, components, and features of the seal portion 704 are identified with the same reference numerals except that a value of 100 has been added thereto.

The seal portion 804 illustrated in FIG. 25 is configured to contain separated layers of different types of granular material. Generally, the granular material included in the various embodiments disclosed herein can be a suitable biocompatible material. The physical attributes, however, of the granular material can be selected to provide a range of different jamming characteristics and conformance properties. Thus, any of the embodiments disclosed herein can include any granular material, including those described as follows:

- Variable size, wherein the granular material contains a range of granule sizes. This may enable improved jamming between the granules.
- Breathability, wherein the granular material is breathable and allows excess water vapor to escape.
- Spherical geometry, wherein each of the granules is spherical. This may improve user comfort by minimizing contact with sharp edges or corners.
- Polyhedral geometry, wherein each of the granules has a number of flat surfaces and corners. In some materials the corners may be rounded.
- Variable geometry, wherein the granular material contains granules of a variety of geometries.
- Composite material, wherein the granules may be of a variety of differing materials that provide specific physical attributes in combination.
- Compressibility, wherein the granules may be compressible, incompressible, or may be mixed with both compressible and incompressible granules together in the same granular jamming chamber. This may provide a softer and more conformable mask seal. In some embodiments, some or all of the compressible granules may contain air, which may make the mask lighter to wear.
- Thermal conductivity, wherein the granular material can be thermally conductive, thermally non-conductive or a mixture of both thermally conductive and non-conductive granules together in the same granular jamming chamber so as to allow the desired thermoregulation of the user's skin. This may improve user comfort and compliance.

With continued reference to FIG. 25, the seal portion 804 can include a plurality of layers of a plurality of different granular materials. The granular materials can configured to contain different sized granules in each layer or other different characteristics.

As shown in FIG. 25, the seal portion 804 includes a granular jamming chamber 830 divided into three layers; a first layer 900, a second layer 902 and a third layer 904.

The three layers 900, 902, 904 of the chamber 830, in some embodiments, each contain granular materials of different size. For example, the first layer 900 of the chamber 830 can include micro-sized granules. The second layer 902 can comprise granules that are larger than the first granular material. Similarly, the third layer 904 can include granules that are a macro-size and larger than the second granular material. The layers 900, 902, 904 of granular material can be separated by screens. For example, the first and second layers 900, 902 can be separated by screen 906 and the second layer 902 and the third layer 904 can be separated by screen 908. The screens 906, 908 are configured to prevent passage of any of the granular material between the various layers 900, 902, 904, but are also configured to allow a suspension fluid 936, such as air or another gas, to pass there through.

In some embodiments, the first layer 900 containing micro-sized granules is configured to be adjacent to the sealing surface 885. This configuration can be advantageous in providing a more "high-definition" conformance between the seal 885 and the user's face. The micro-sized granules can more closely match facial geometries as a result of there being less space between the granules when in a jammed state. The differing granule size in each layer 900, 902, 904, can provide variable rigidity and structure to the seal portion 804. Additionally, in some embodiments, the screens 906,

908 can provide some structural reinforcement characteristics, similar to those provided in the seal portion 704*a*-704*d* described above.

FIGS. 26*a*-29*b* illustrate four additional modifications of the seals described above, each of which include an inflatable bladder. Additionally, the illustrations of FIGS. 26*a*-29*b* reflect only a partial cross-section of the seal member that can be used with any of the masks described above or masks or portions of masks described below, for example, the masks including a frame such as that partially illustrated in FIGS. 30-35 below.

Figure 26A:
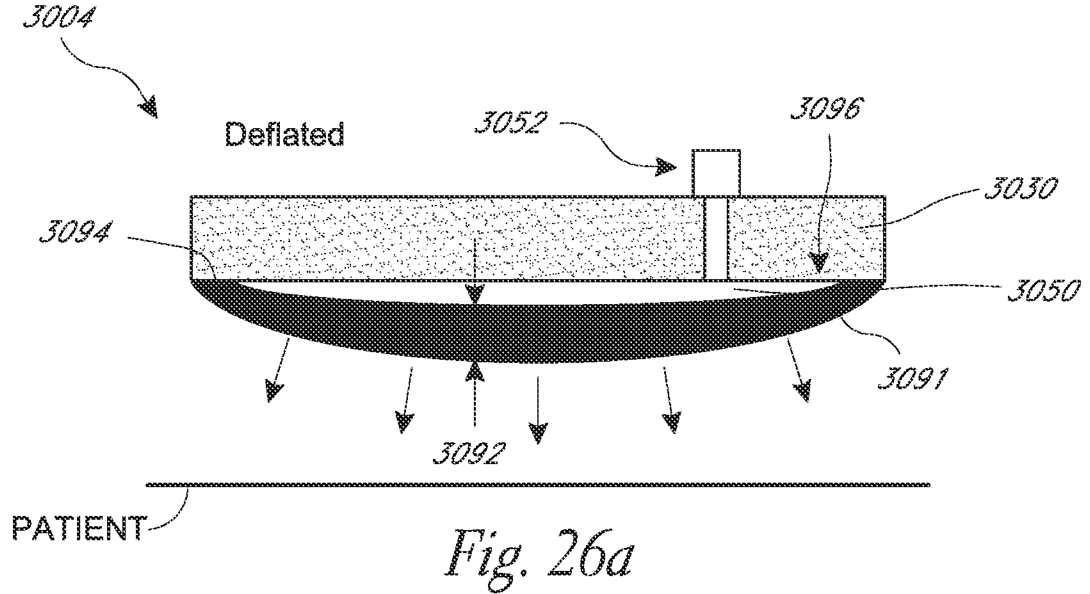
FIG. 26*a* is a schematic sectional view of a modification of a seal portion including an inflatable bladder, in a deflated state.
Figure 26B:
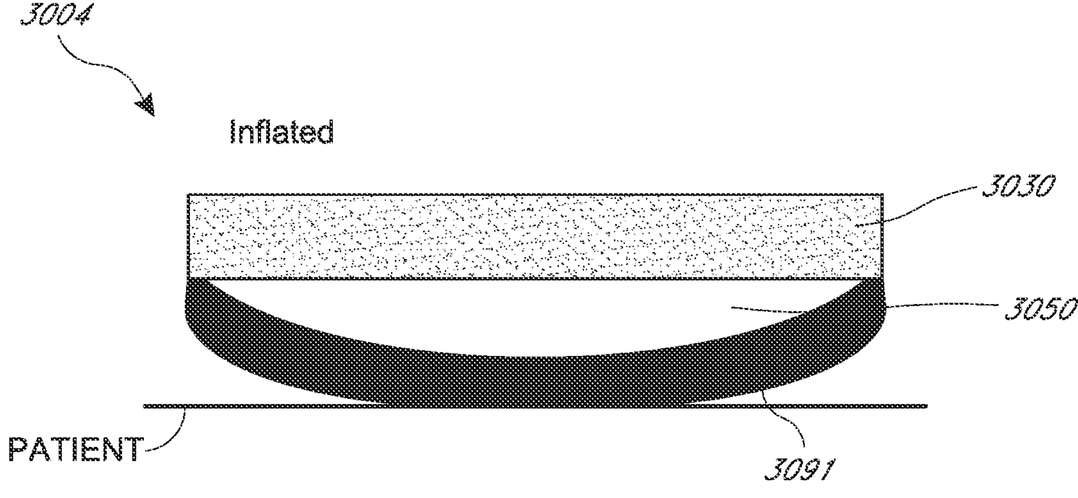
FIG. 26*b* is a schematic sectional view of the seal of FIG. 26*a* in an inflated state.

With reference to FIGS. 26*a*, 26*b*, a seal 3004 can compromise a multi-layered design including a variable stiffness portion, which can be in the form of granular jamming chamber 3030, a comfort layer 3091, which can comprise any type of more compressible comfortable materials or configurations such as silicone, foam, gel material or other materials. Additionally, the seal 3004 can include an inflatable portion 3050 disposed between the variable stiffness portion 3030 and the comfort layer 3091.

The variable stiffness portion 3030 can be in the form of any of the variations of granular jamming enabled seal portions described above, including multi-layers, variable sizes and hardnesses of granular material, stiffening components, etc. The variable stiffness portion 3030, the inflatable bladder 3050, and the comfort layer 3091, can be individually encased in material forming three independent chambers, however, they can also share common walls. In some embodiments, the walls of these portions 3030, 3050, 3091 can be made from thin, soft, elastic or nonelastic materials as desired, including silicone, and other materials described above.

FIG. 26*a* illustrates the seal 3004 in a deflated state. As shown in FIG. 26*a*, the comfort layer 3091 has a thickness 3092 in its relaxed state and when the seal inflatable portion 3050 is deflated. Additionally, the comfort layer 3091 includes end walls 3094, 3096 at the inner and outer edges of the seal 3004. The inner and outer ends of the comfort layer 3092 are attached to the remaining portions of the seal 3004, for example, the variable stiffness portion 3030, at relatively small contact areas.

With reference to FIG. 26*b*, when the inflatable portion 3050 is inflated, for example, when the variable stiffness portion 3030 is optionally in a state of higher stiffness, fluid added into the inflatable portion 3050, such as a liquid or a gas, causes the comfort layer 3091 to deflect away from the variable stiffness portion 3030 which can provide the additional optional benefit of changing the characteristic and potentially increasing the amount of surface contact between the comfort layer 3091 and a patient. In some embodiments, the seal 3004 can include a valve 3052 for inflating and deflating the inflatable portion 3050. Such a change in shape of the comfort layer 3091 relative to the relatively stiffer portion 3030, caused by inflation of the inflatable portion 3050, can thus help reduce or eliminate leaks.

The shape of the comfort layer 3091 and the manner in which it is connected to the relatively stiffer portion 3030 can affect the way the comfort layer 3091 expands as the inflatable portion 3050 is inflated. For example, if the comfort layer 3091 is a substantially uniform thickness along and/or around the inflatable bladder, the inflatable portion 3050 and the comfort layer 3091 can expand in a direction that is substantially perpendicular to the stiffer portion 3030. As shown in FIGS. 26*a* and 26*b*, the inflatable portion 3050 has a substantially flat cross-section. Thus, when inflated, the inflatable portion 3050 and the comfort layer 3091 also tend to have a generally flat profile, which can enhance or provide increased contact area with the patient, such as with the patient's face.

Figure 27A:
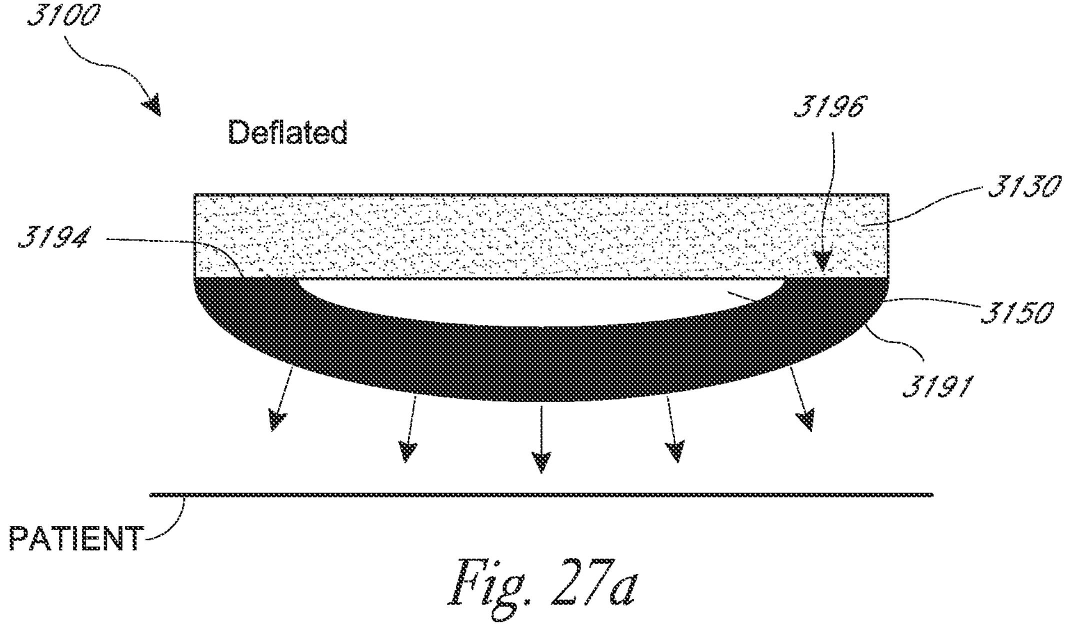
FIG. 27*a* is a schematic sectional view of yet another modification of the seal, in a deflated state.
Figure 27B:
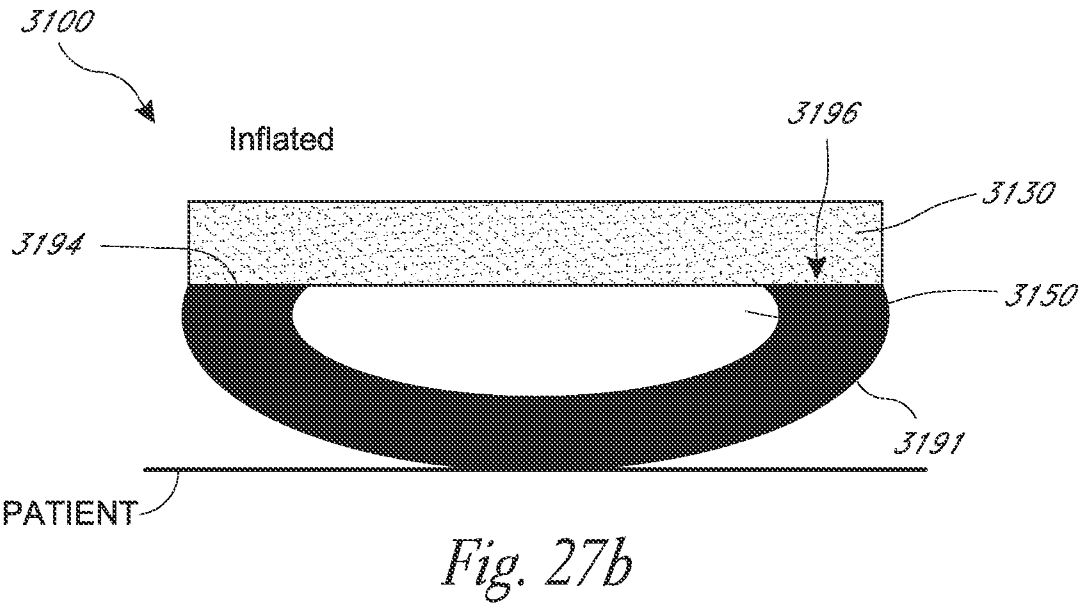
FIG. 27*b* is a schematic sectional view of the seal of FIG. 27*a*, in an inflated state.

With reference to FIGS. 27*a* and 27*b*, a seal 3100 can include a more rounded comfort layer 3191 when the seal 3100 is in a relaxed state, as shown by comparison of FIG. 27*a* and FIG. 26*a*. For example, with continued reference to FIG. 27*a*, the comfort layer 3191 can have its ends 3194, 3196 connected to a lower surface of the relatively stiffer portion 3130. This provides the comfort layer 3191 with a generally more rounded configuration.

Thus, with continued reference to FIG. 27*b*, when the inflatable portion 3150 is inflated, the inflatable portion 3150 becomes more rounded as well as the outer surface of the comfort layer 3191, which can provide a different sealing characteristic when the inflatable portion 3150 is inflated, for example, providing a more rounded outer sealing surface of the seal 3100 which may provide less contact with certain portions of a user's face or more contact with different portions of a user's face.

Figure 28A:
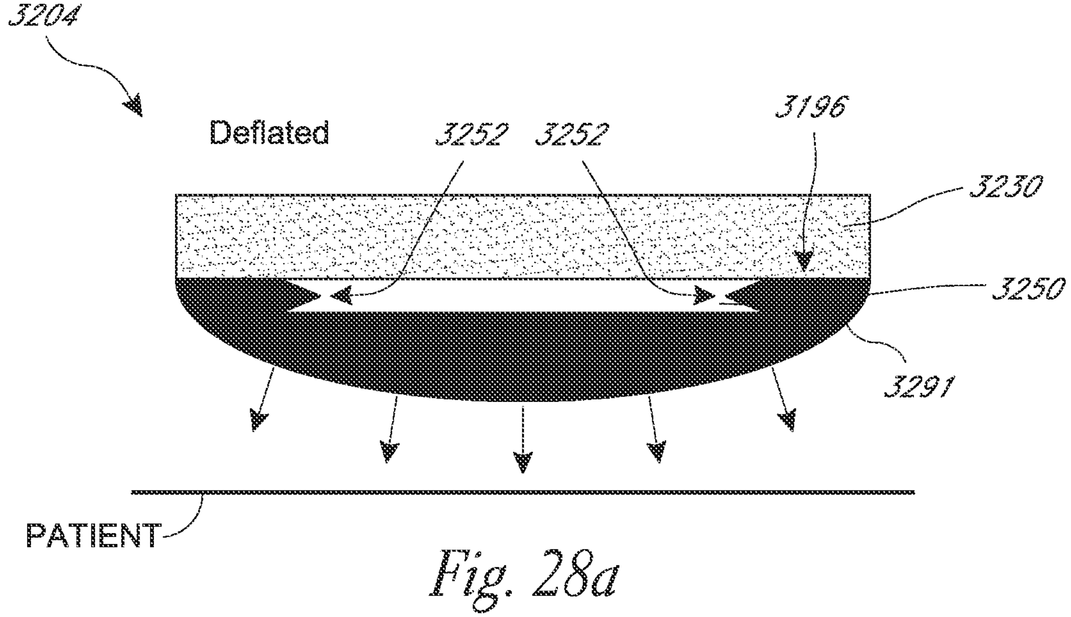
FIG. 28*a* is a sectional view of yet another modification of the seal, in a deflated state.
Figure 28B:
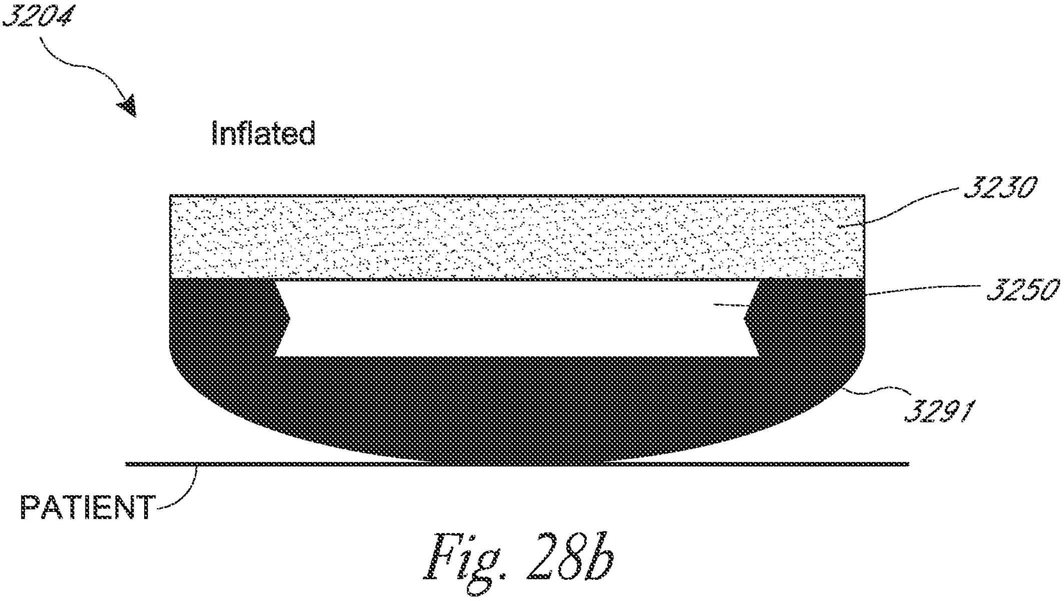
FIG. 28*b* is a schematic sectional view of the seal of FIG. 28*a*, in an inflated state.

FIGS. 28*a* and 28*b* illustrate yet another modification of the seal 3004, identified generally by the reference numeral 3204. As illustrated in FIGS. 28*a*, 28*b*, the seal 3204 includes bellows 3252 disposed in side walls of the inflatable portion 3250 to provide a different manner in which the inflatable portion 3250 inflates and thus deforms during inflation. For example, the bellows 3252 can be made from a substantially inelastic material, in a folded position when the inflatable portion 3250 is deflated and thus unfold and allow expansion of the side walls in a more linear direction during inflation of the inflatable portion 3250. Such use of bellows or other devices can result in a more unidirectional expansion of the inflatable portion 3250 and the comfort layer 3291. As such, the comfort layer 3291 can expand towards a patient and generate a larger contact area with the patient and/or increased sealing pressure against a patient.

Figure 29A:
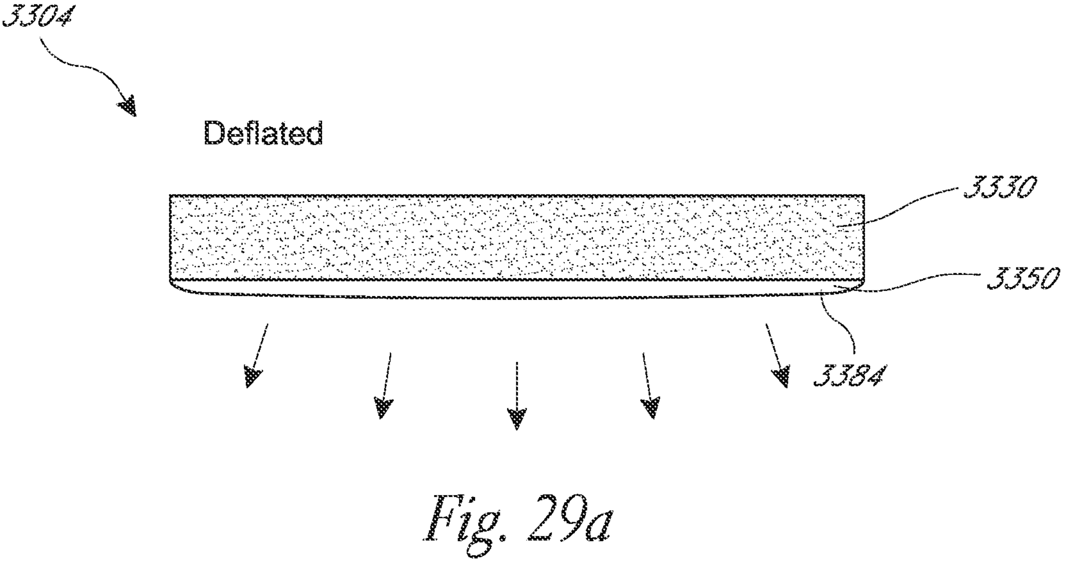
FIG. 29*a* is a schematic sectional view of yet another modification of the seal, in a deflated state.
Figure 29B:
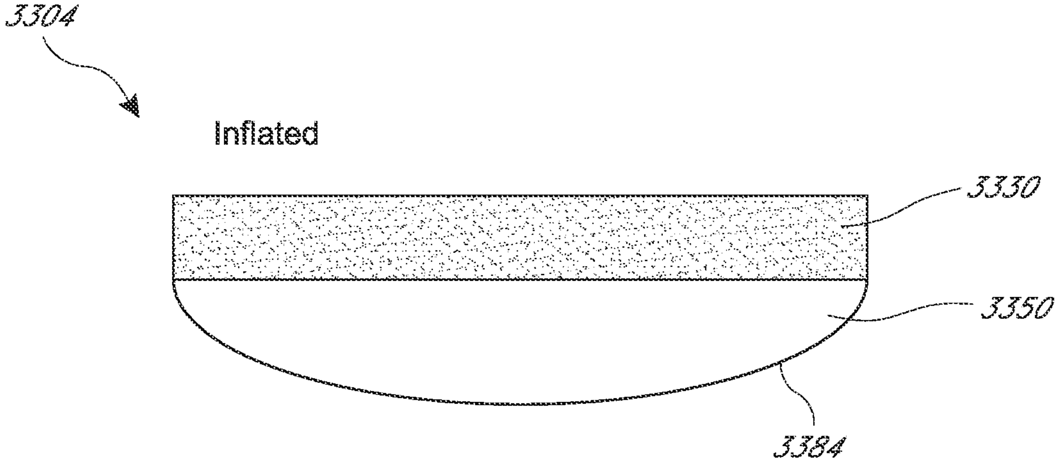
FIG. 29*b* is a schematic sectional view of the seal of FIG. 29*a*, in an inflated state.

With reference to FIGS. 29*a* and 29*b*, yet another modification of the seal 3004, identified generally by the reference numeral 3304. In such a configuration, the seal 3304 includes an inflatable portion 3350 but with no additional thickened comfort layer. Rather, the inflatable portion 3350 can be formed of a thin sheet material, such as silicone or other materials, and can be inflated on demand, for example, using a valve such as the valve 3052 noted above. As such, the inflatable portion 3350 can be inflated after the generally stiffer portion 3330 is configured into the desired shape. Then, upon inflation, the inflatable portion 3350 can provide enhanced contact with the patient's face, and due to the configuration of the outer wall 3384, can more readily adapt to finer features of a patient, such as creases, recesses, or folds in a patient's skin so as to provide a better seal with less contact pressure.

In some embodiments, a mask can be provided with the seal 3304 and the inflatable portion 3350 in a permanently inflated state. As such, such a mask is further simplified, easier to use, and potentially with lower manufacturing costs. Using a sufficiently elastic outer wall 3384, the bladder 3350 can remain inflated during the process of reshaping the relatively stiffer portion 3330. Then after shaping the relatively stiffer portion 3330 into the desired shape, the inflatable portion 3350 would elastically reshape itself, under the force of the fluid contained therein and the elastic behavior or elastic characteristic of the outer wall 3384 and can thus enhance a seal between the relatively stiffer portion 3330 and a patient.

FIGS. 30-35 illustrate an optional process for using a mask with the seal 3004, although the description of FIGS. 30-35 would also apply to the use of any of the other seals described above.

Figures 30, 31:
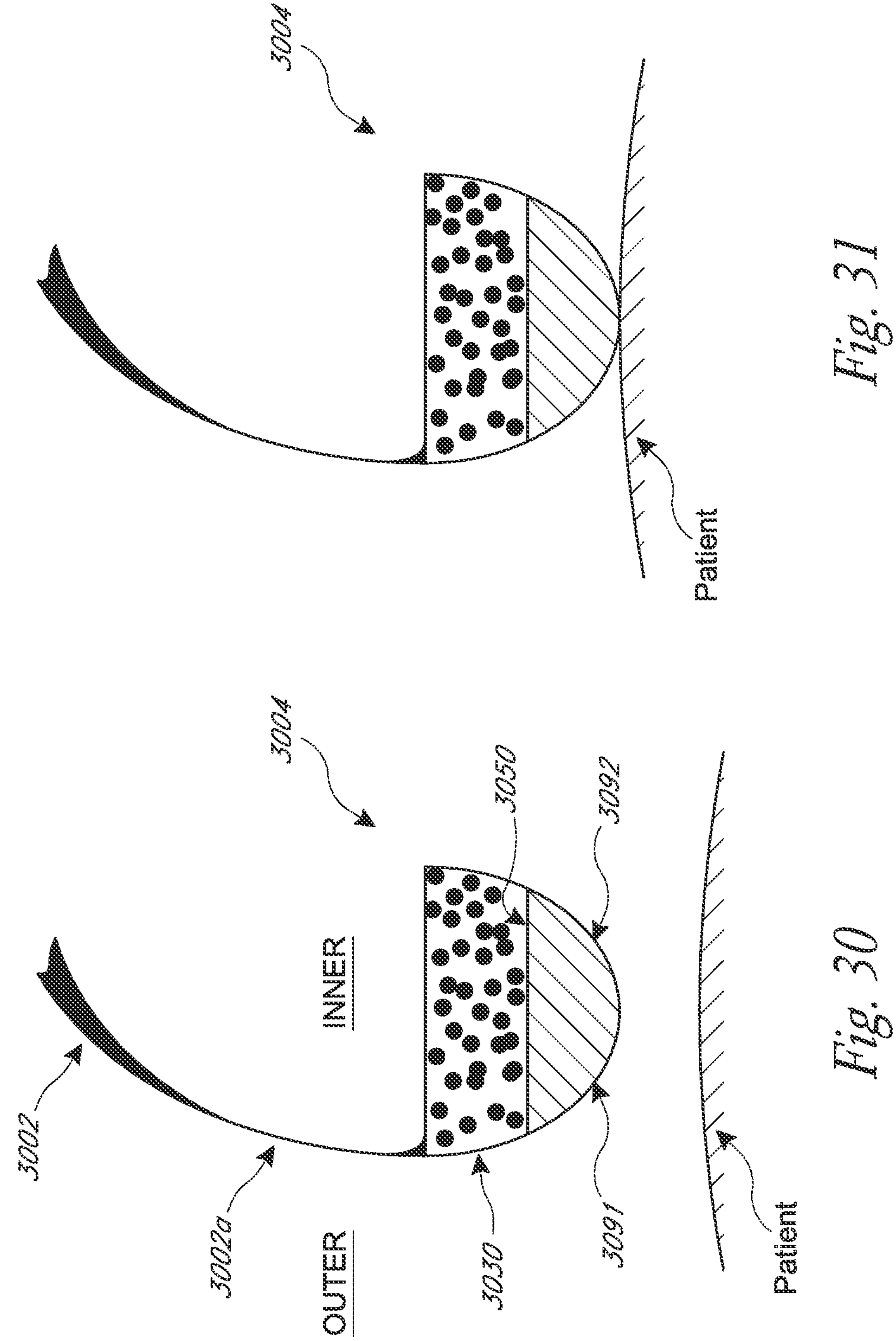
FIG. 30 is a schematic sectional view of yet another modification of the mask including the seals of FIG. 26*a*, in a relaxed state.
FIG. 31 is a schematic sectional view of the mask of FIG. 30, in a state in which an outer surface of the seal is touching a surface of a patient.

FIG. 30 illustrates a mask having a frame 3002 which can be a generally stiff portion of an associated mask. For example, in some embodiments, the frame 3002 is made of polycarbonate or other generally stiff materials. Optionally, as shown in FIG. 30, the frame 3002 can include a skirt portion 3002*a* which can be generally less stiff or more flexible than the frame 3002. For example, in some embodiments, the skirt 3002*a* can be formed of silicone. The skirt 3102*a* is connected to the seal 3004. In the illustrated embodiment, the skirt 3002*a* is connected to an outer edge of the seal 3004.

In the orientation illustrated in FIG. 30, the seal 3004 is spaced away from the patient. During the process of fitting the mask to a patient, the seal 3004 can be brought into contact with a patient, as shown in FIG. 31.

Figure 32:
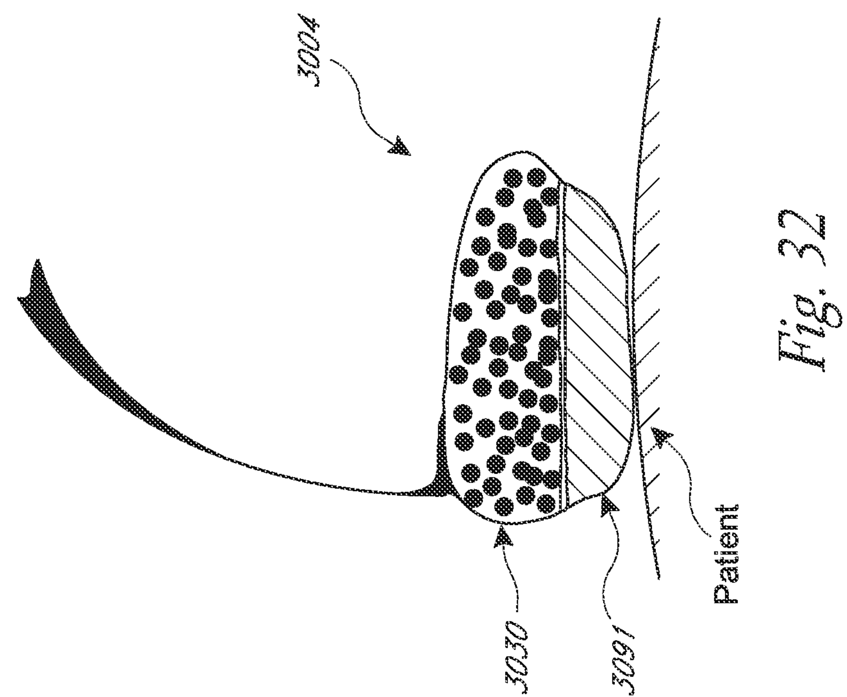
FIG. 32 is a schematic sectional view of the mask of FIG. 30, in a state in which the seal is pressed against a surface of a patient such that portions of the seal are deformed from the relaxed state of FIG. 30.

With reference to FIG. 32, the mask can be pushed against the patient so as to cause some deformation of the outer surface of the seal 3004 for example, including the outer surface of the comfort layer 3091, and in some uses, deformation of the portion 3030. In embodiments where the portion 3030 is a variable stiffness portion, operating under the principle of granular jamming for example, the portion 3030 can deform to better follow contours of a patient when in its neutral or a reduced-stiffness state. Further, in some embodiments, the comfort layer 3091 can be configured to be less stiff than the stiffness of the portion 3030. For example, in some embodiments, the comfort layer 3091 can be configured to be less stiff than the stiffness of the portion 3030 when the portion 3030 is in a neutral state, or optionally, when the portion 3030 is in an intermediate stiffness state that is less stiff than the stiffness of the portion 3030 when in a maximum stiffness state. As such, the portion 3030 can conform to the geometry of the target portion of the patient, such as the patient's face, without the comfort layer 3091 deforming to an extent that would reduce conformance of the comfort layer 3091 to the target portion of the patient. Additionally, in an embodiment the comfort layer 3091 does not restrict the ability of the portion 3030 to conform to the target portion of the patient when the portion 3030 is in its neutral or a reduced-stiffness state.

Figure 33:
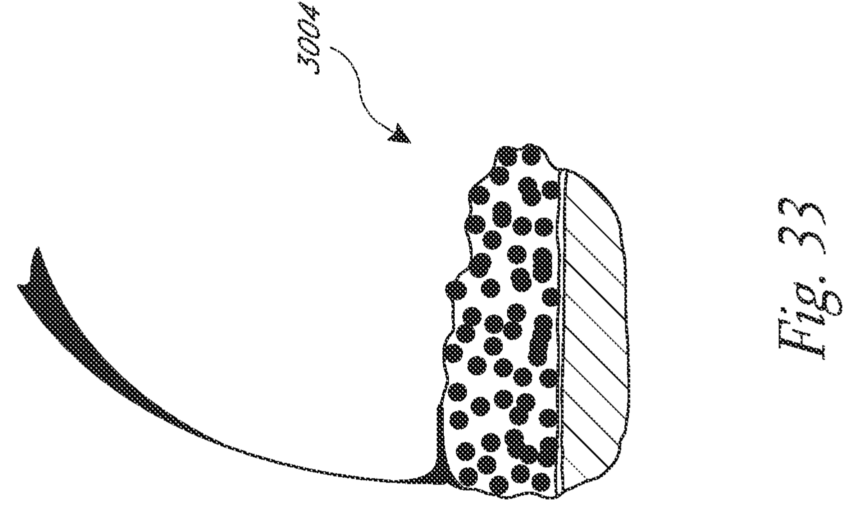
FIG. 33 is a sectional view of the mask of FIG. 30, illustrating a transition of a portion of the seal to a state of greater stiffness.

With reference to FIG. 33, with the portion 3030 deformed from its relaxed shape, the portion 3030 can be transitioned to a higher state of greater stiffness, for example, by subjecting the portion 3030 to a vacuum so as to achieve a state of higher stiffness through granular jamming. This transition is illustrated in FIG. 33 by the deformation of the outer casing of the portion 3030 into a tighter fitting engagement of the granules within the portion 3030. At this point, the portion 3030 is now relatively stiffer and deformed from its relaxed state illustrated in FIG. 30.

Figures 34, 35:
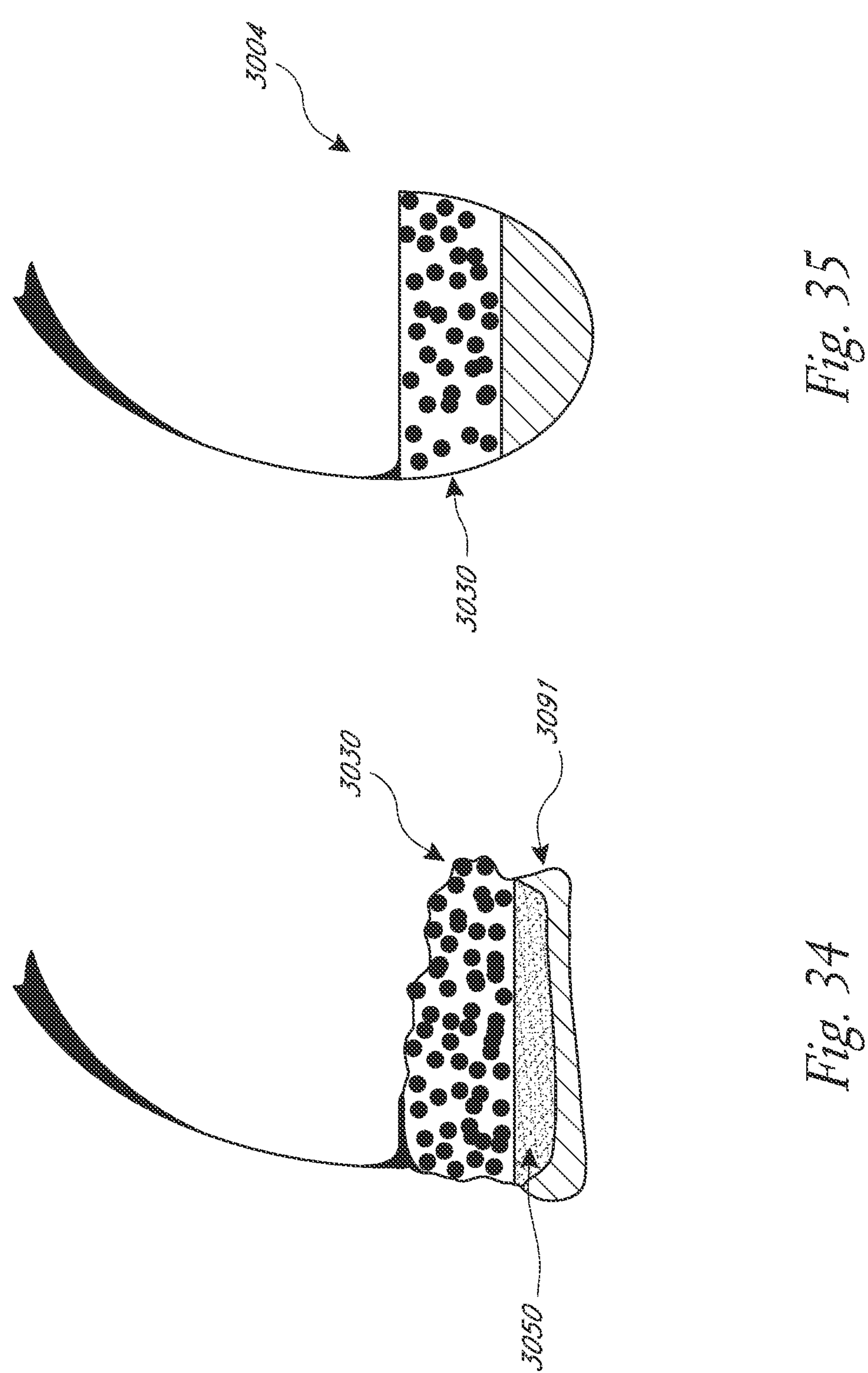
FIG. 34 is a schematic sectional view of the mask of FIG. 30, with an inflatable bladder shown in an inflated state.
FIG. 35 is a sectional view of the mask of FIG. 34, with the bladder returned to a deflated state, and returned to a neutral state after the state illustrated in FIG. 34.

With reference to FIG. 34, with the portion 3030 still in a state of heightened stiffness, the inflatable portion 3050 can be inflated. For example, but without limitation, a fluid such as a gas or a liquid, including but without limitation, air. As such, the outer surface of the comfort layer 3091 is urged away from the relatively stiffer portion 3030 into greater contact with the patient. As such, the comfort layer 3091 can further expand into small creases, folds, or recesses of the user's face and thereby achieve a better seal using lower tensions and straps for attaching the mask to a patient. The additional forces provided by the inflatable portion 3050 can also apply small forces to a user's face resulting in some creases being smoothed. Finally, the expansion of the inflatable portion 3050 can increase the surface area of the comfort layer 3091 in contact with the user's face thereby increasing the likelihood that a seal can be generated around a crease, fold, or recess which may have caused a leak or leak zone.

Figure 2B:
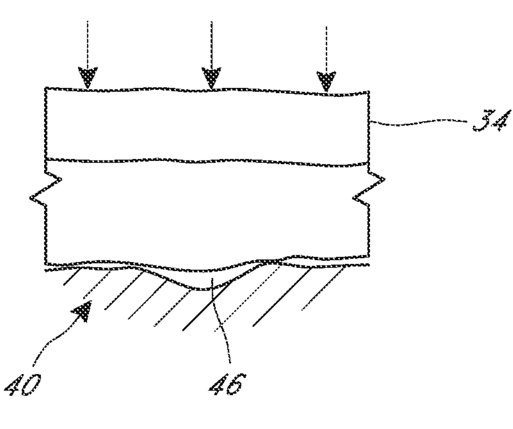
FIG. 2*b* is an enlarged side view of a portion of the seal of the mask of FIG. 2*a* illustrating a point at which the leak occurs, identified by the area 2*b* of FIG. 2*a*.
Figure 2C:
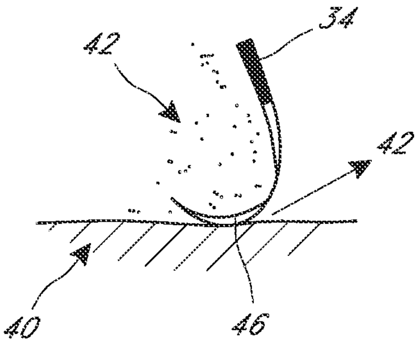
FIG. 2*c* is a sectional view of the portion of the seal illustrated in FIG. 2*b*.
Figure 36:
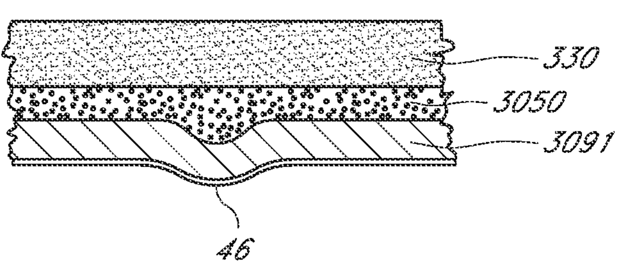
FIG. 36 is an enlarged sectional view of the mask of FIG. 30, illustrating a contour of an outer surface of the seal during use.

Generally, a fluid filled inflatable portion 3050 will expand along the path of least resistance when expanding under positive pressure. This can result in the inflatable portion 3050 expanding away from the relatively stiffer portion 3030 and into any gaps between the patient's skin and the sealing surface of the comfort layer 3091. By expanding in this way, the comfort layer 3091 can be pushed into and at least partially fill gaps between the comfort layer and the patient's face. For example, as shown in FIG. 36, the outer surface of the comfort layer 3091 can expand into the recess 46 (also described above with reference to FIG. 2*b*).

With reference to FIG. 35, in some embodiments, the fluid from within the inflatable portion 350 can be released, allowing the seal 3004 to return to its neutral state.

The granular jamming chambers of the embodiments of the masks disclosed above can be connected to any type of vacuum device for the purpose of transitioning to the jammed state. For example, such a vacuum device can be used to initiate the jamming phase within the masks disclosed herein by reducing the pressure within the conforming seal and/or frame. A vacuum can be supplied to the mask in a number of ways, including but not limited to a dedicated vacuum pump, hospital suction lines, or a syringe.

A vacuum supply may not always be readily accessible in the environment in which the mask of the present disclosure is to be used. It is, however, more likely that there will be a positive pressure source available, since it is required to provide therapy via the mask. It may therefore be advantageous to be able to generate a vacuum supply from a positive pressure source.

Figure 38:
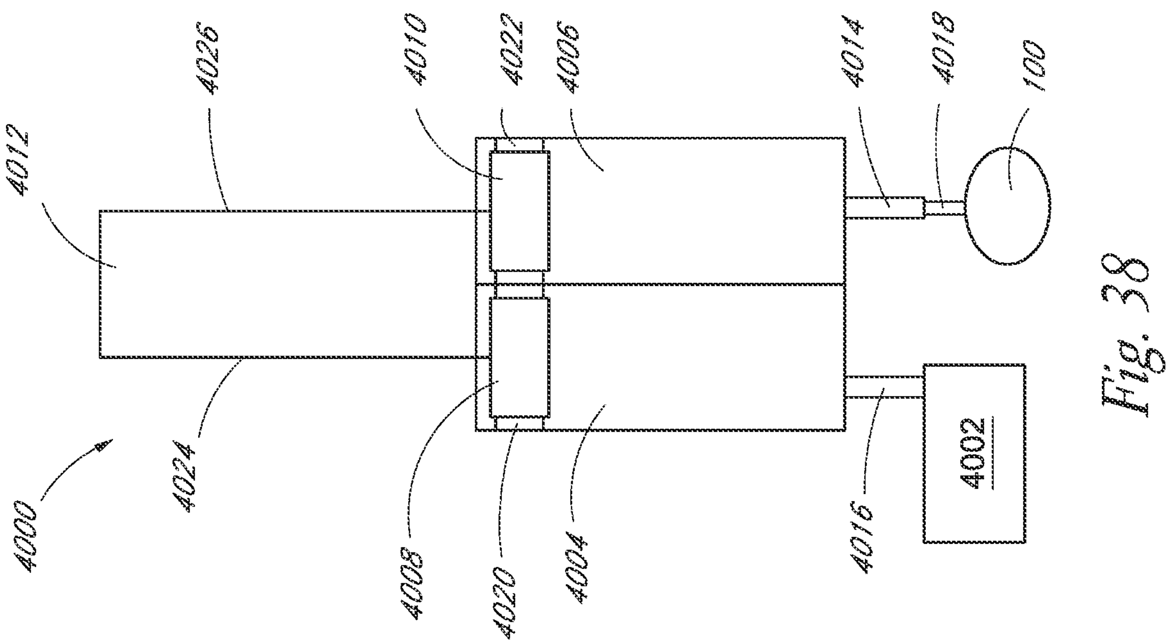
FIGS. 37 and 38 are schematic views of a vacuum supply device, in two different states.
Figure 37:
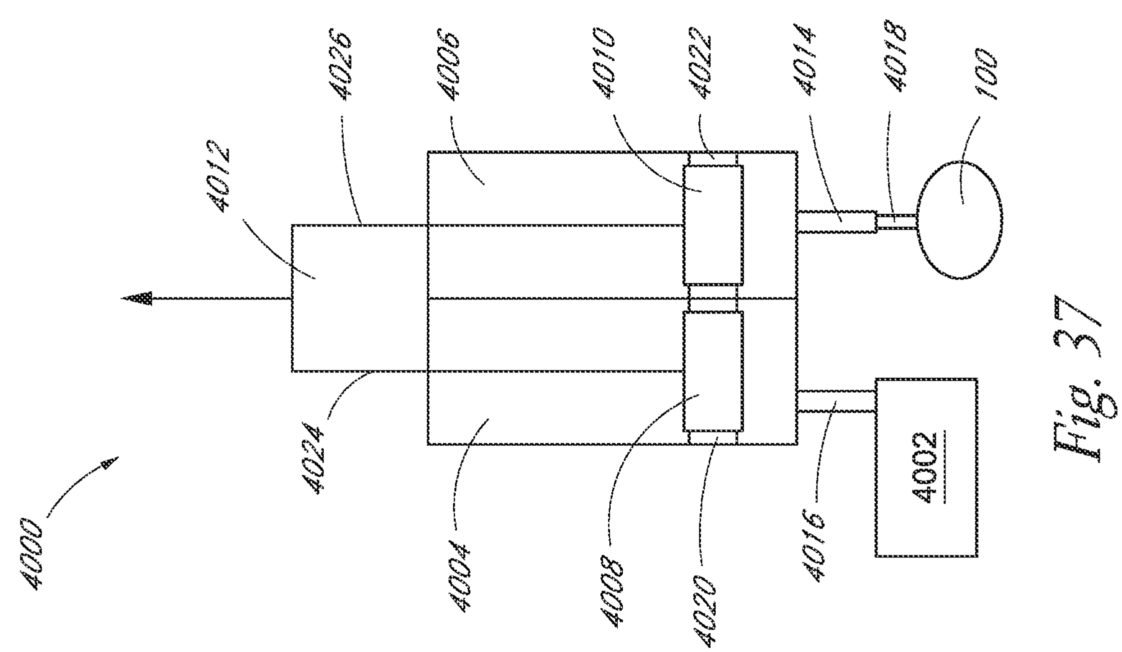

With reference to FIGS. 37 and 38, one non-limiting exemplary embodiment of a vacuum supply 4000, which can convert positive pressure to negative pressure, is shown in FIGS. 37 and 38. FIG. 37 shows the device 4000 comprising a pressure source 4002, first and second chambers 4004, 4006, first and second plungers 4008, 4010, a coupler 4012, and a vacuum connection 4014. The pressure source 4002 may be any suitable supply of pressurized fluid, such as but not limited to flow generator, ventilators or pressurized gas lines. In FIG. 37, the device 4000 is shown in a substantially neutral state without a pressure being applied by the pressure source.

The first chamber 4004 can comprise a high pressure connection 4016, which is configured to connect to the pressure source 4002. The second chamber 4006 comprises a low pressure/vacuum connection 4014, configured to connect to a mask connection 4018; wherein the mask connection 4018 is configured to connect to a mask, such as the mask 100 or any of the masks described above. The first and second chambers 4004, 4006 may be configured to house the first and second plungers, 4008, 4010, respectively.

The first and second plungers 4008, 4010 can comprise seals 4020, 4022, respectively, and first and second plunger columns 4024, 4026. The first and second plunger columns 4024, 4026 are configured to be connected by the coupler 4012, such that the movement of one plunger (e.g., 4008) will result in movement of the other plunger (e.g., 4010).

The configuration of the device 4000, as described herein, allows the application of a positive pressure in the first chamber 4004 to be converted to a negative pressure, or vacuum, in the second chamber 4006.

FIG. 38 shows the device 4000, of the present description, with a positive pressure applied to the first chamber 4004. The positive pressure provided by the pressure source 4002 applies a force to the first plunger 4008 causing it to translate along the chamber 4004. The movement of the first plunger 4008 causes the first and second plunger columns 4024, 4026, linked by the coupler 4012, to move the second plunger 4010, inducing a negative pressure or vacuum within the second chamber 4006. The vacuum can be applied to the mask 100 via the low pressure/vacuum connection 4014 and mask connection 4018, such that a jamming transition phase is induced in the variable stiffness portion included in a seal and/or frame of the mask 100.

Figure 39:
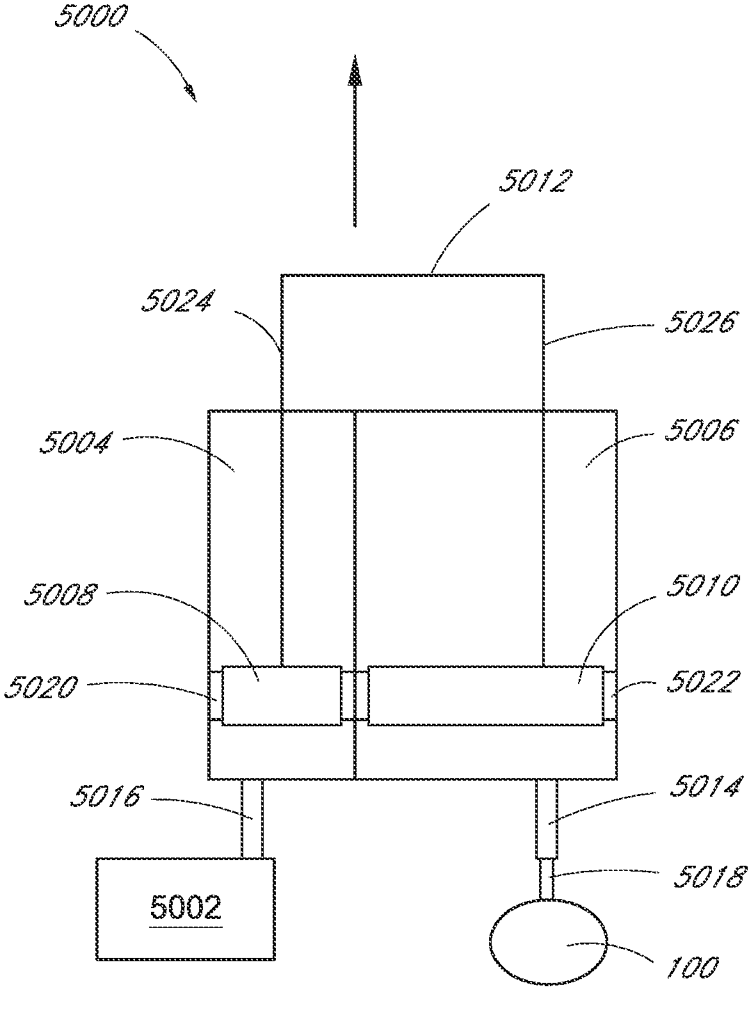
FIG. 39 is a schematic illustration of a modification of the vacuum supply device of FIGS. 37 and 38.
Figure 40:
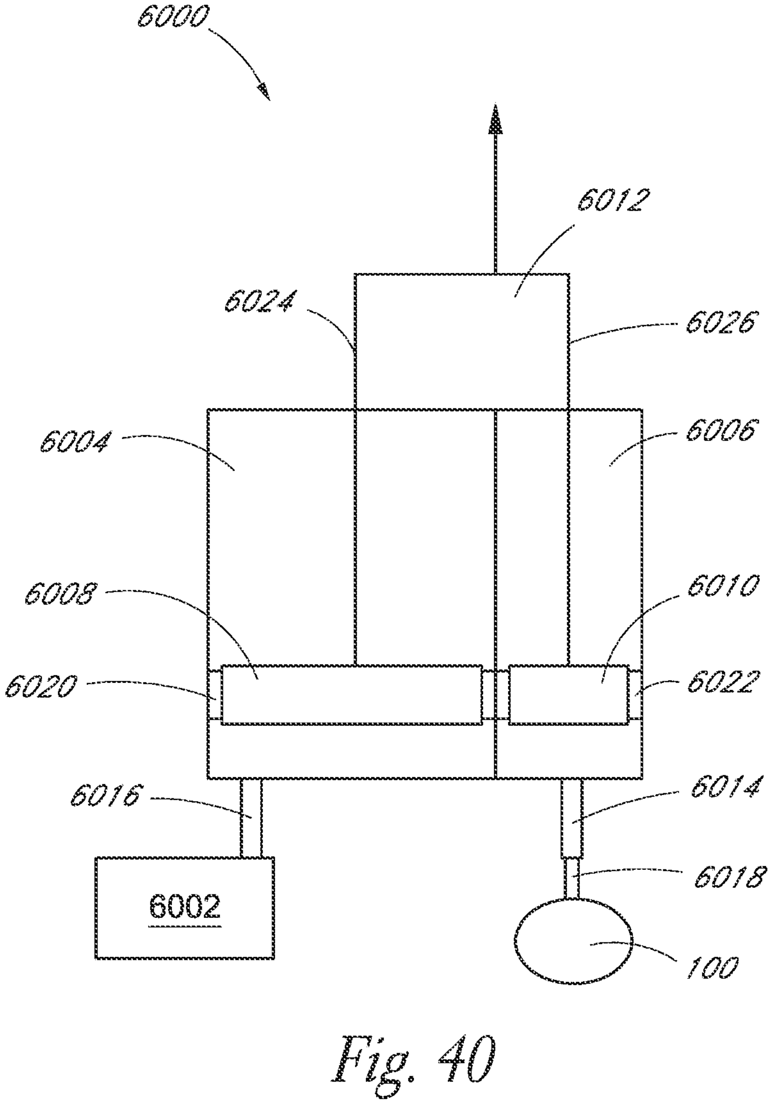
FIG. 40 is a schematic illustration of yet another modification of the vacuum supply device.

FIGS. 39 and 40 illustrate a modification of the mask 4000, identified generally by the reference numeral 5000. Parts, components, and features of the device 5000 that are the same, or can be substantially the same as the components of the device 4000 are identified with the same reference numeral, except that 1000 has been added thereto.

In the device 5000, the first and second chambers 5004, 5006 are of different sizes in order to provide a step up or step down in the pressure ratio between the chambers 5004, 5006. Correspondingly, the first and second plungers 5008, 5010 and respective seals 5020, 5022 are sized to match the size of the respective chamber 5004, 5006. As shown in FIG. 39, the first chamber 5004 is smaller than the second chamber 5006. This may result in a large positive pressure being converted into a smaller negative pressure in the second chamber 5006. Alternatively, as depicted in the modification of FIG. 40, identified by the reference numeral 6000, the first chamber 6004 can be larger than the second chamber 6006. Such a differential sizing of the chamber 6004, 6006 can result in the application of a small positive pressure in chamber 6004 being converted into a larger negative pressure in chamber 6006.

Figure 41:
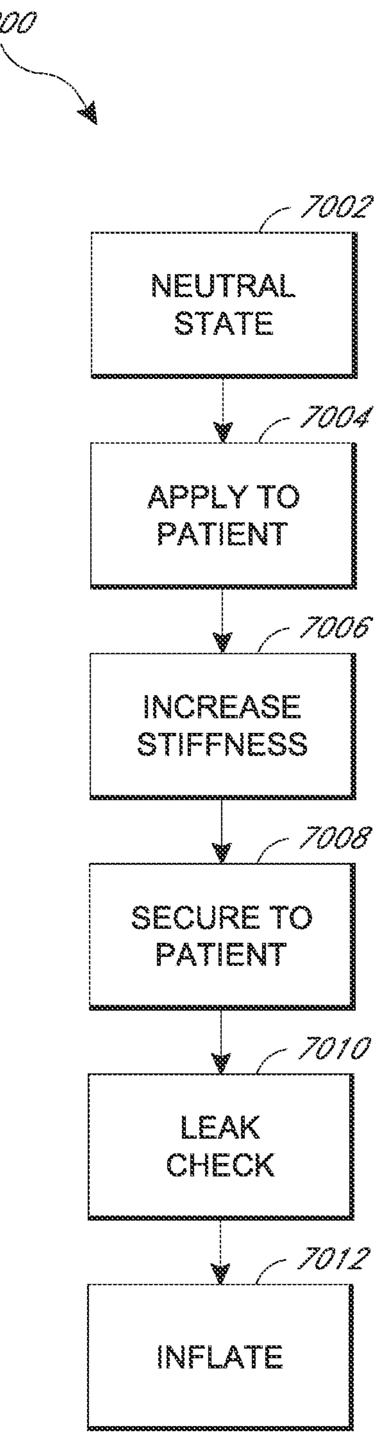
FIG. 41 is a flow chart illustrating a method that can be used for fitting a mask onto a patient.

FIG. 41 includes a flow chart illustrating a method that can be used for fitting any of the above-described masks to a patient, including masks having inflatable portions. With reference to the flow chart 7000 of FIG. 41, the method can begin with operation block 7002.

In operation block 7002, the method 7000 can begin, with the mask 100 in a neutral state. For example, the mask 100 can be considered to be in a neutral state if the mask includes a variable stiffness portion, and the variable stiffness portion is in a state of lower stiffness. If the variable stiffness portion is in the form of a granular jamming portion, then the granular jamming portion would be considered to be in a neutral state if the granules are not compressed into a jammed state, and thus can flow, for example, viscously, within the chamber. Additionally, if the mask includes an inflatable portion, then the inflatable portion would be considered to be in a neutral state if the inflatable portion is deflated, collapsed, at atmospheric pressure or under a vacuum. After the operation block 7002, the method 7000 can move onto operation block 7004.

In the operation block 7004, the mask can be applied to a patient's face. For example, the mask 100 can be pushed against a patient's face by the patient or healthcare worker. Additionally, the mask, such as the seal portion 104 and/or the frame portion 102 can be deformed to better conform to a patient's face. Additionally, the deformation of the seal portion can include deformation of a variable stiffness portion, such as a granular jamming portion, an inflatable portion, a gel or comfort layer, etc. After the operation block 7004, the method 7000 can move on to the operation block 7006.

In the operation block 7006, the deformed state of the mask can be preserved. For example, if the mask includes a variable stiffness portion, the variable stiffness portion can be transitioned to a higher stiffness state. If the variable stiffness portion is a granular jamming enabled portion, then the granular jamming enabled portion can be subject to a vacuum to cause the granular jamming enabled portion to increase in viscosity and/or to be otherwise transitioned to a higher stiffness state, which in some embodiments, can be a "jammed" state. In some embodiments, such transitioned state of a variable stiffness portion or a granular jamming enabled portion can be considered as forming a relatively stiffer portion of a seal or mask. After the operation block 7006, the method 7000 can move onto operation block 7008.

In operation block 7008, the mask can optionally be secured to a patient's head with headgear, such as straps. Additionally, air under a positive pressure, can be supplied to a patient's airways through the mask. After the operation block 7008, the method 7000 can move on to operation block 7010.

In operation block 7010, leaks of the mask can be detected. For example, the patient or healthcare worker can probe the areas around the vicinity of a seal of the mask to determine if a positive pressure flow of air can be detected. After the operation block 7010, the method 7000 can move on to operation block 7012.

In the operation block 7012, a portion of the seal can be expanded. For example, if the mask includes an inflatable portion, the inflatable portion can be expanded. In some embodiments, the inflatable portion can be disposed between a relatively stiffer portion, such as a variable stiffness portion in a state of heightened stiffness, or a granular jamming portion which has been transitioned toward a jamming state. In some embodiments, the inflatable portion can be provided with positive fluid pressure, such as positive pressure of gas, to thereby inflate the inflatable portion. Optionally, the inflatable portion can be inflated until any detected leaks have been reduced to an acceptable amount or eliminated. Other techniques can also be used.

A number of examples of therapeutic fluid delivery device aspects of the interfaces, and variations on each aspect, have been discussed with reference to other Figures. The present application contemplates that a therapeutic fluid delivery device may incorporate some aspects but not other aspects. For example, a therapeutic fluid delivery device might incorporate aspects of a mask while using a different arrangement for securing the mask to the user. All of these variations are considered within the scope of this application.

Although the inventions disclosed herein are described in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments can be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above.

What is claimed is:

1. A respiratory mask able to fit a plurality of differently-shaped human faces, the respiratory mask comprising:

a frame portion comprising a perimeter portion and a conduit connection portion;

a seal portion connected to the perimeter portion of the frame portion, the seal portion comprising a sealing surface and a connecting surface, the connecting surface being connected to the perimeter portion, the sealing surface able to form a seal with a portion of a human face;

a granular chamber located in the seal portion and containing a granular material, the granular chamber configured to be transitioned between a conforming state and a fixed state;

a vacuum connection port in the seal portion;

a vacuum connection conduit connected to the vacuum connection portion and configured to allow a vacuum to be applied to the granular chamber through the vacuum connection port to transition the granular chamber from the conforming state to the fixed state;

at least one internal structure within the granular chamber that is separate from and surrounded by the granular material, and is separate from and spaced apart from the vacuum connection port and the vacuum connection conduit, wherein the granular material is positioned between the vacuum connection port and the at least one internal structure, the at least one internal structure having a first surface and a second surface opposite the first surface, wherein the granular material acts on a surface area of each of the first surface and the second surface of the at least one internal structure to provide a reaction force that is able to provide controlled deformation to the respiratory mask in response to the granular chamber transitioning from the conforming state to the fixed state.

2. The respiratory mask of claim 1, whereby compressing the seal portion results in the at least one internal structure pulling sides of the seal portion inwards towards a nose of the human face.

3. The respiratory mask of claim 1, whereby in the conforming state, the seal portion is able to deform and conform to facial geometry of the human face.

4. The respiratory mask of claim 1, wherein in the fixed state, the seal portion retains a geometry that was established in the conforming state.

5. The respiratory mask of claim 1, wherein the at least one internal structure is configured such that at least a portion of the granular material moves around and past the at least one internal structure when the seal portion is deformed.

6. The respiratory mask of claim 1, wherein the at least one internal structure is suspended in a central position within the granular chamber of the seal portion.

7. The respiratory mask of claim 1, wherein the at least one internal structure resists contacting a membrane of the seal portion.

8. The respiratory mask of claim 1, wherein the at least one internal structure is flexible and inelastic.

9. The respiratory mask of claim 1, wherein the at least one internal structure has a length and defines a cross-sectional shape that extends along the length, wherein the length of the at least one internal structure extends along a longitudinal length of the seal portion, and wherein the first surface and the second surface are separated from one another by a thickness of the cross-sectional shape.

10. The respiratory mask of claim 9, wherein the first surface faces toward the frame portion and the second surface faces away from the frame portion.

11. The respiratory mask of claim 1, wherein the at least one internal structure is an internal skeleton.

12. The respiratory mask of claim 11, wherein the internal skeleton comprises a pitchfork shaped cross-section.

13. The respiratory mask of claim 11, wherein the internal skeleton extends longitudinally within the seal portion.

14. The respiratory mask of claim 11, wherein the granular chamber forms an annular loop, wherein the internal skeleton extends around and along an entire length of the annular loop within the granular chamber.

15. The respiratory mask of claim 11, wherein the internal skeleton is able to constrict movement of the granular material within the seal portion.

16. The respiratory mask of claim 1, wherein the at least one internal structure is of a non-granular material.

17. The respiratory mask of claim 1, wherein the sealing surface extends along an entire length of the seal portion and is configured to encircle one or both nostrils and/or a mouth of the human face, wherein the at least one internal structure forms an annular loop around and along the entire length of the seal portion.

18. The respiratory mask of claim 1, wherein the controlled deformation comprises an inducement of a clamshelling movement.

19. A respiratory mask able to fit a plurality of differently-shaped human faces, the respiratory mask comprising:

a frame portion comprising a perimeter portion and a conduit connection portion;

a seal portion connected to the perimeter portion of the frame portion, the seal portion formed of a seal material and comprising a sealing surface and a connecting surface, the connecting surface being connected to the perimeter portion, the sealing surface forming a loop to encircle an interior space that is configured to receive one or both nostrils and/or a mouth of the human face and able to form a seal with a portion of a human face, the seal portion further comprising an inner wall defining a portion of the interior space and an outer wall on an opposite side of the sealing surface from the inner wall, the outer wall is configured to face an outside of the respiratory mask when the respiratory mask is being worn by the user;

a granular chamber located in the seal portion and containing a granular material, the granular chamber configured to be transitioned between a conforming state and a fixed state;

at least one structural layer within the granular chamber that is separate from and surrounded by the granular material, wherein the at least one structural layer extends from the inner wall of the seal portion to the outer wall of the seal portion, the at least one structural layer having a thickness defined between a first surface and a second surface opposite the first surface;

wherein the at least one structural layer is more rigid than the inner wall and the outer wall of the seal portion;

wherein the granular material acts on a surface area of each of the first surface and the second surface of the at least one structural layer to provide a reaction force that is able to provide controlled deformation to the respiratory mask in response to the granular chamber transitioning from the conforming state to the fixed state.

20. The respiratory mask of claim 19, wherein the at least one structural layer is formed of the seal material, wherein the thickness of the at least one structural layer is greater than each of a thickness of the inner wall and a thickness of the outer wall.

21. A respiratory mask able to fit a plurality of differently-shaped human faces, the respiratory mask comprising:

a frame portion comprising a perimeter portion and a conduit connection portion;

a seal portion connected to the perimeter portion of the frame portion, the seal portion comprising a sealing surface and a connecting surface, the connecting surface being connected to the perimeter portion, the sealing surface able to form a seal with a portion of a human face;

a granular chamber located in the seal portion and containing a granular material, the granular chamber configured to be transitioned between a conforming state and a fixed state;

at least one internal structure within the granular chamber that is separate from and surrounded by the granular material, the at least one internal structure having a first surface and a second surface opposite the first surface, wherein the granular material acts on a surface area of each of the first surface and the second surface of the at least one internal structure in response to deformation of the frame portion, and generates a reactionary force that is able to provide controlled deformation to the seal portion of the respiratory mask;

wherein the controlled deformation comprises translation of deformation in a height dimension of the seal portion to movement or deformation in a width dimension of the seal portion, or vice-versa, as a result of the reactionary force generated by the at least one internal structure acting on the granular material, wherein the at least one internal structure is an internal skeleton, and the granular chamber forms an annular loop, wherein the internal skeleton extends around and along an entire length of the annular loop within the granular chamber.

* * * * *